United States Patent [19]
Ueda et al.

[11] Patent Number: 5,591,744
[45] Date of Patent: *Jan. 7, 1997

[54] BENZOHETEROCYCLIC COMPOUNDS

[75] Inventors: Hiraki Ueda, Mishima; Hisashi Miyamoto; Hiroshi Yamashita, both of Tokushima; Hitoshi Tone, Itano, all of Japan

[73] Assignee: Otsuka Pharmaceutical Company, Limited, Tokyo-to, Japan

[*] Notice: The portion of the term of this patent subsequent to Apr. 8, 2008, has been disclaimed.

[21] Appl. No.: 179,300

[22] Filed: Apr. 8, 1988

[30] Foreign Application Priority Data

| | | | |
|---|---|---|---|
| Apr. 16, 1987 | [JP] | Japan | 62-94198 |
| Apr. 24, 1987 | [JP] | Japan | 62-102351 |
| Apr. 30, 1987 | [JP] | Japan | 62-108361 |
| May 22, 1987 | [JP] | Japan | 62-126598 |
| Jun. 16, 1987 | [JP] | Japan | 62-149544 |
| Jul. 14, 1987 | [JP] | Japan | 62-176126 |
| Nov. 9, 1987 | [JP] | Japan | 62-283776 |
| Nov. 12, 1987 | [JP] | Japan | 62-287108 |

[51] Int. Cl.⁶ .................. A61K 31/47; C07D 401/04
[52] U.S. Cl. .................. 514/252; 514/231.5; 514/249; 514/312; 544/128; 544/349; 544/363; 546/156
[58] Field of Search .................. 544/363, 349, 544/128; 514/252, 231.5, 249, 312; 546/156

[56] References Cited

U.S. PATENT DOCUMENTS

| | | | |
|---|---|---|---|
| 4,544,747 | 10/1985 | Ishikawa et al. | 544/363 |
| 4,578,473 | 3/1986 | Domagala et al. | 546/14 |
| 4,699,992 | 10/1987 | Grohe | 544/363 |
| 4,762,844 | 4/1988 | Grohe et al. | 546/156 |
| 4,920,120 | 4/1990 | Domagala et al. | 546/156 |
| 4,940,794 | 9/1990 | Hermecz et al. | 546/13 |
| 4,945,160 | 7/1990 | Kiely et al. | 546/156 |
| 4,980,470 | 12/1990 | Masuzawa et al. | 544/363 |

FOREIGN PATENT DOCUMENTS

| | | |
|---|---|---|
| 899399 | 7/1984 | Belgium . |
| 0126355 | 11/1984 | European Pat. Off. . |
| 0178388 | 4/1986 | European Pat. Off. . |
| 0202763 | 11/1986 | European Pat. Off. . |
| 0206101 | 12/1986 | European Pat. Off. . |
| 0221463 | 5/1987 | European Pat. Off. . |
| 0230053 | 7/1987 | European Pat. Off. . |
| 0237955 | 9/1987 | European Pat. Off. . |
| 0242789 | 10/1987 | European Pat. Off. . |
| 0247464 | 12/1987 | European Pat. Off. . |
| 2057440 | 4/1981 | United Kingdom ........ 544/363 |

OTHER PUBLICATIONS

Ueda, et al., "Chemical Abstracts", vol. 110, 1989, col. 110:173109k.
Domagala, et al., "Chemical Abstracts", vol. 112, 1990, Col. 112:98508a.
Matsumoto, et al., "Chemical Abstracts", vol. 112, 1990, Col. 112:192308d.
Patent Abstracts of Japan, vol. 11, No. 167, May 28, 1987, 62-469.

*Primary Examiner*—Bernard Dentz
*Attorney, Agent, or Firm*—Finnegan, Henderson, Farabow, Garrett & Dunner, L.L.P.

[57] ABSTRACT

Novel 4-oxoquinoline-3-carboxylic acid compounds of the formula:

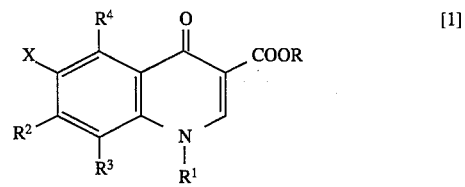

[1]

wherein $R^1$ is cyclopropyl which may have 1 to 3 substituents of alkyl and halogen; phenyl which may be substituted by 1 to 3 substituents of alkoxy, halogen and OH; alkyl which may be substituted by halogen, alkanoyloxy or OH; alkenyl; or thienyl, $R^2$ is 5- to 9-membered saturated or unsaturated heterocyclic ring which may be sustituted, $R^3$ is alkyl or halogen, $R^4$ is alkyl or halogen, R is H or alkyl, $R^1$ and $R^3$ may be taken together to form

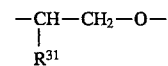

wherein $R^{31}$ is H or alkyl, and X is halogen, provided that $R^3$ and $R^4$ are not simultaneously halogen, and salts thereof, said compounds having excellent antimicrobial activity and hence being useful as an antimicrobial agent, and a pharmaceutical composition containing said compound as an active ingredient.

37 Claims, No Drawings

BENZOHETEROCYCLIC COMPOUNDS

The present invention relates to novel antimicrobial benzoheterocyclic compounds of the formula [1]:

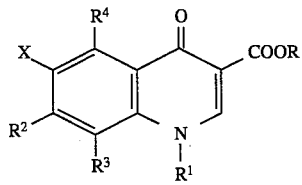

wherein $R^1$ is a cyclopropyl which may be substituted by 1 to 3 of substituents selected from the group consisting of a (lower) alkyl and a halogen atom, a phenyl which may be substituted by 1 to 3 of substituents selected from the group consisting of a (lower) alkoxy, a halogen atom and hydroxy on phenyl ring, a (lower) alkyl which may be substituted by a halogen atom, a (lower) alkanoyloxy or hydroxy, a (lower) alkenyl or thienyl, $R^2$ is a 5- to 9-membered saturated or unsaturated heterocyclic ring which may be sustituted, $R^3$ is a (lower) alkyl, or a halogen atom, $R^4$ is a (lower) alkyl or a halogen atom, R is hydrogen atom or a (lower) alkyl, $R^1$ and $R^3$ may be combined to form the group:

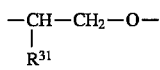

wherein $R^{31}$ is hydrogen atom or a (lower) alkyl, and X is a halogen atom, provided that $R^3$ and $R^4$ are not simultaneously halogen atom, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

Prior art

There are many references which disclose 4-oxoquinoline-3-carboxylic acid derivatives useful as anti-bacterial agents. Among these references, European Patent Publication No. 178388 discloses 1-cyclopropyl-7-piperazino-dihydroquinoline carboxylic acid derivatives of the formula:

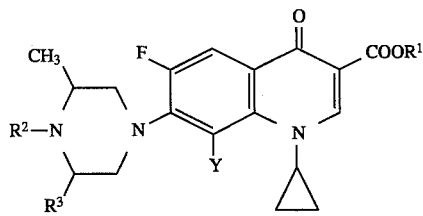

wherein $R^1$ is H or lower alkyl, $R^2$ is H, methyl, p-nitro(or amino)-benzyl, is H, methyl, or aminomethyl, and Y is Cl or F.

Japanese Patent First Publication (Kokai) No. 69/1987 discloses 1-cyclopropyl-dihydroquinoline carboxylic acid derivatives of the formula:

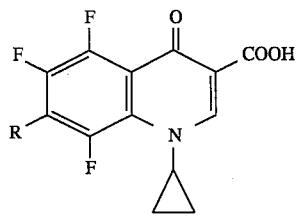

wherein R is substituted or unsubstituted pyrrolidinyl or piperazinyl.

WO 8606630 discloses 1-cycloalkyl-1,4-dihydro-4-oxo-quinoline-3-carboxylic acid derivatives of the formula:

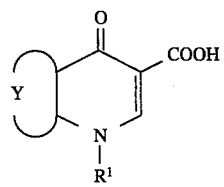

wherein $R^1$ is $C_3$–$C_6$ cycloalkyl, Y is optionally substituted 6-membered aromatic group.

U.S. Pat. No. 4,556,658 discloses 7-amino-1-cyclo-propyl-3-quinoline carboxylic acid derivatives of the formula:

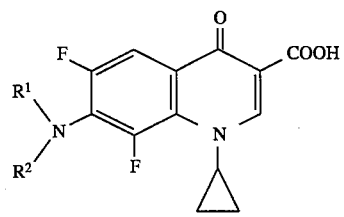

wherein $R^1$ and $R^2$ are each substituted or unsubstituted alkyl, or both may combine together with N atom to form a 5- or 6-membered heterocyclic ring.

Belgian Patent 899399 discloses 1-cyclopropyl-7-piperazinyl-dihydroquinoline carboxylic acid derivatives of the formula:

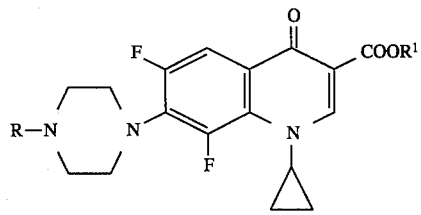

wherein R is H, methyl, or p-nitro(or amino)-benzyl, $R^1$ is H or lower alkyl, and Y is Cl, F, methyl.

Similar 1-substituted-7-heterocyclic group-substituted dihydroquinoline carboxylic acid derivatives are also disclosed in other many references.

However, these known references do not disclose any compound having an alkyl substituent at 5-position.

BRIEF DESCRIPTION OF THE INVENTION

The object of the present invention is to provide novel benzoheterocyclic compounds of the formula [1] and salts

3 thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the specification, the term "a halogen atom" includes fluorine, chlorine, bromine or iodine atom.

The term "a cyclopropyl which may be substituted by 1 to 3 of substituents selected from the group consisting of a (lower) alkyl and a halogen atom" includes cyclopropyl which may be substituted by 1 to 3 of substituents selected from the group consisting of a straight chain or branched chain $C_1$–$C_6$ alkyl and a halogen atom, such as cyclopropyl, 2-fluoro-1-cyclopropyl, 2-chloro-1-cyclopropyl, 2-bromo-1-cyclopropyl, 2-iodo-1-cyclopropyl, 2,2-dichloro-1-cyclopropyl, 2,2-dibromo-1-cyclopropyl, 2,2,3-trichloro-1-cyclopropyl, 2-methyl-1-cyclopropyl, 2-ethyl-1-cyclopropyl, 2-propyl-l-cyclopropyl, 2-butyl-1-cyclopropyl, 2-pentyl-1-cyclopropyl, 2-hexyl-1-cyclopropyl, 2,2-dimethyl-1-cyclopropyl, 2,3-dimethyl-1-cyclopropyl, 2,2,3-trimethyl-1-cyclopropyl, 2-fluoro-3-methyl-1-cyclopropyl, 2,2-diethyl-1-cyclopropyl, 2-methyl-3-propyl-1-cyclopropyl, and the like.

The term "a (lower) alkyl" includes straight chain or branched chain $C_1$–$C_6$ alkyl, such as methyl, ethyl, propyl, isopropyl, butyl, tert-butyl, pentyl, hexyl, etc.

The term "a 5- to 9-membered saturated or unsaturated heterocyclic ring which may be substituted" denotes a 5- to 9-membered saturated or unsaturated heterocyclic ring which may be substituted by a (lower) alkyl; a cycloalkyl; a phenyl (lower) alkyl in which phenyl ring may be substituted by a lower alkoxy, nitro or amino; a phenyl which may be substituted by a halogen atom or a (lower) alkyl optionally substituted by 1 to 3 of halogen atoms; a pyridyl; a (lower) alkyl having 1 to 3 substituents selected from the group consisting of hydroxy, an amino which may be substituted by a (lower) alkyl, a (lower) alkanoyl, a cycloalkyl or a (lower) alkoxycarbonyl, a (lower) alkoxy and a halogen atom; a (lower) alkynyl; a (lower) alkanoyl which may be substituted by 1 to 7 of halogen atoms; a (lower) alkenylcarbonyl having 1 to 3 substituents selected from the group consisting of a halogen atom and a carboxy; a (lower) alkoxycarbonyl; an aminocarbonyl which may be substituted by a (lower) alkyl; a phenyl(lower)alkoxycarbonyl; an amino(lower)alkanoyl which may be substituted by a phenyl(lower)alkoxycarbonyl; a (lower) alkoxycarbonyl(lower)alkyl; a carboxy(lower)alkyl; an anilinocarbonyl(lower)alkyl; an amino which may be substituted by a (lower) alkyl, a phenyl(lower)alkyl, a (lower) alkoxycarbonyl or a (lower) alkanoyl; hydroxy; a (lower) alkylsulfonyl which may be substituted by 1 to 3 of halogen atoms; phthalide; a 2(5H)-furanone which may be substituted by 1 or 2 of halogen atoms; a sulfo(lower)alkyl; oxo; a (lower) alkoxy; a (lower) alkenyl; a halogen atom; a (lower) alkanoyloxy; a 2-oxo-1,3-dioxolenemethyl which may be substituted by phenyl or a (lower) alkyl; a cycloalkylamino; a 2-oxo-1,3-dioxolenemethylamino which may be substituted by phenyl

4 or a (lower) alkyl; a (lower) alkylthio; or thio, and includes more specifically 5- to 9-membered saturated or unsaturated heterocyclic rings which may be substituted by 1 to 3 of substituents selected from the group consisting of a straight chain or branched chain $C_1$–$C_6$ alkyl; a $C_3$–$C_8$ cycloalkyl; a phenylalkyl in which phenyl ring may be substituted by a straight chain or branched chain $C_1$–$C_6$ alkoxy, nitro or amino and the alkyl moiety is a straight chain or branched chain $C_1$–$C_6$ alkyl; a phenyl in which phenyl ring may be substituted by a halogen atom or by a straight chain or branched chain $C_1$–$C_6$ alkyl which may be substituted by 1 to 3 of halogen atoms; a pyridyl; an amino which may be substituted by 1 or 2 substituents selected from the group consisting of hydroxy, a straight chain or branched chain $C_1$–$C_6$ alkyl, a straight or branched chain $C_1$–$C_6$ alkanoyl, a $C_3$–$C_8$ cycloalkyl and a straight chain or branched chain ($C_1$–$C_6$)alkoxy-carbonyl; a straight chain or branched chain $C_1$–$C_6$ alkyl having 1 to 3 of substituents selected from the group consisting of a straight chain or branched chain $C_1$–$C_6$ alkoxy group and a halogen atom; a straight chain or branched chain $C_2$–$C_6$ alkynyl; a straight chain or branched chain $C_1$–$C_6$ alkanoyl which may be substituted by 1 to 7 of halogen atoms; a straight chain or branched chain ($C_2$–$C_6$)alkenyl-carbonyl substituted by 1 to 3 of halogen atoms or carboxy; a straight chain or branched chain ($C_1$–$C_6$)alkoxy-carbonyl; an aminocarbonyl which may be substituted by 1 or 2 of a straight chain or branched chain $C_1$–$C_6$ alkyl group; a phenylalkoxycarbonyl in which the alkoxy moiety is a straight chain or branched chain $C_1$–$C_6$ alkoxy; a straight chain or branched chain $C_2$–$C_6$ aminoalkanoyl which may be substituted by a phenylalkoxycarbonyl in which the alkoxy moiety is a straight chain or branched chain $C_1$–$C_6$ alkoxy; an alkoxycarbonylalkyl in which the alkoxy and alkyl moieties are straight chain or branched chain $C_1$–$C_6$ alkoxy and alkyl, respectively; a carboxyalkyl in which the alkyl moiety is a straight chain or branched chain $C_1$–$C_6$ alkyl; an anilino-carbonylalkyl in which the alkyl moiety is a straight chain or branched chain $C_1$–$C_6$ alkyl; an amino which may be substituted by 1 or 2 of a straight chain or branched chain $C_1$–$C_6$-alkyl, a phenylalkyl in which the alkyl moiety is a straight chain or branched chain $C_1$–$C_6$ alkyl, a straight chain or branched chain ($C_1$–$C_6$)alkoxy-carbonyl, or a straight chain or branched chain $C_1$–$C_6$ alkanoyl; hydroxy; a straight chain or branched chain $C_1$–$C_6$ alkylsulfonyl which may be substituted by 1 to 3 of halogen atoms; phthalide; a 2(5H)-furanone which may be substituted by 1 or 2 of halogen atoms; a sulfoalkyl in which the alkyl moiety is a straight chain or branched chain $C_1$–$C_6$ alkyl; oxo; a straight chain or branched chain $C_1$–$C_6$ alkoxy; a straight chain or branched chain $C_2$–$C_6$ alkenyl; a halogen atom; a straight chain or branched chain $C_2$–$C_6$ alkanoyloxy; a $C_3$–$C_8$ cycloalkylamino; a straight chain or branched chain $C_1$–$C_6$ alkylthio; thio; a 2-oxo-1,3-dioxolenemethyl which may be substituted by phenyl or a straight chain or branched chain $C_1$–$C_6$alkyl; and a 2-oxo-1,3-dioxolenemethylamino which may be substituted by phenyl or a straight chain or branched chain $C_1$–$C_6$ alkyl, such as, for example, piperazinyl, piperidinyl, pyrrolidinyl, homopiperazinyl, morpholino, thiomorpholino, 1,2,5,6-tetrahydropyridyl, imidazolyl, 1,4-diazabicyclo-[4.3.0]nonan-4-yl, thiomorpholino-4-oxide, thiomorpholino-4,4-dioxide, pyrazolidinyl, hexahydropyridazinyl, pyridyl, thiazolidinyl, 2-thio-1-imidazolidinyl, 2-oxo-1-imidazol-idinyl, 3,7-diazabicyclo[4.3.0]nonan-3-yl, 4-methyl-1-piperazinyl, 4-ethyl-1-piperazinyl, 4-propyl-1-piperazinyl, 4-t-butyl-1-piperazinyl, 4-pentyl-1-piperazinyl, 4-hexyl-1-piperazinyl, 3-methyl-1-piperazinyl, 3,4-dimethyl-1-piperazinyl, 2,5- dimethyl-1-piperazinyl, 2,4,5-trimethyl-1-piperazinyl, 3,4,5-trimethyl-1-piperazinyl, 3-ethyl-1-piperazinyl, 3-propyl-4-methyl-1-piperazinyl, 2-n-butyl-5-methyl-1-piperazinyl, 2-pentyl-5-hexyl-1-piperazinyl, 4-formyl-1-piperazinyl, 4-acetyl-1-piperazinyl, 4-propionyl-1-piperazinyl, 4-butyryl-1-piperazinyl, 4-pentanoyl-1-piperazinyl, 4-hexanoyl-1-piperazinyl, 4-(α,α,α-trifluoroacetyl)-1-piperazinyl, 4-(β,β,β-trifluoro-α,α-difluoropropionyl)-1-piperazinyl, 4-(γ,γ,γ-trifluoro-β,β-difluoro-α,α-difluoro-butyryl)-1-piperazinyl, 4-(α,α-dichloroacetyl)-1-piperazinyl, 4-(α-bromoacetyl)-1-piperazinyl, 4-(α-iodoacetyl)-1-piperazinyl, 4-(β-fluoropropionyl)-1-piperazinyl, 4-(β-fluoro-α-fluoropropionyl)-1-piperazinyl, 4-(6-fluorohexanoyl)-1-piperazinyl, 4-(4-chloropentanoyl)-1-piperazinyl, 4-benzyl-1-piperazinyl, 4-(2-phenylethyl)-1-piperazinyl, 4-(1-phenylethyl)-1-piperazinyl, 4-(3-phenylpropyl)-1-piperazinyl, 4-(4-phenylbutyl)-1-piperazinyl, 4-(1,1-dimethyl-2-phenylethyl)-1-piperazinyl, 4-(5-phenylpentyl)-1-piperazinyl, 4-(6-phenylhexyl)-1-piperazinyl, 4-(2-methyl-3-phenylpropyl)-1-piperazinyl, 4-amino-1-piperazinyl, 3-amino-1-piperazinyl, 2-amino-1-piperazinyl, 4-methylamino-1-piperazinyl, 3-dimethylamino-1-piperazinyl, 2-ethylamino-1-piperazinyl, 4-propylamino-1-piperazinyl, 4-t-butylamino-1-piperazinyl, 3-pentylamino-1-piperazinyl, 2-hexylamino-1-piperazinyl, 4-diethylamino-1-piperazinyl, 4-(N-methyl-N-n-butylamino)-1-piperazinyl, 3-(N-methyl-N-pentylamino)-1-piperazinyl, 2-(N-ethyl-N-hexylamino)-1-piperazinyl, 4-acetylamino-1-piperazinyl, 3-formylamino-1-piperazinyl, 2-propionylamino-1-piperazinyl, 4-butyrylamino-1-piperazinyl, 3-pentanoylamino-1-piperazinyl, 2-hexanoylamino-1-piperazinyl, 4-(N-methyl-N-acetylamino)-1-piperazinyl, 3-(N-ethyl-N-propionylamino)-1-piperazinyl, 4-hydroxy-1-piperazinyl, 3-hydroxy-1-piperazinyl, 2-hydroxy-1-piperazinyl, 4-methylsulfonyl-1-piperazinyl, 4-ethylsulfonyl-1-piperazinyl, 4-propylsulfonyl-1-piperazinyl, 4-n-butylsulfonyl-1-piperazinyl, 4-pentylsulfonyl-1-piperazinyl, 4-hexylsulfonyl-1-piperazinyl, 4-trifluoromethylsulfonyl-1-piperazinyl, 4-(2-fluoroethylsulfonyl)-1-piperazinyl, 4-(3-fluoropropylsulfonyl)-1-piperazinyl, 4-(4,4,4-trifluorobutylsulfonyl)-1-piperazinyl, 4-sulfonyl-1-piperazinyl, 4-(phthalid-3-yl)-1-piperazinyl, 4-(3,4-dibromo-2(5H)-furanon-5-yl)-1-piperazinyl, 4-(3,4-dichloro-2(5H)-furanon-5-yl)-1-piperazinyl, 4-(2(5H)-furanon-5-yl)-1-piperazinyl, 4-(3-chloro-2(5H)-furanon-5-yl)-1-piperazinyl, 4-formyl-3-methyl-1-piperazinyl, 4-acetyl-3-ethyl-1-piperazinyl, 4-acetyl-2-methyl-1-piperazinyl, 4-methyl-3-hydroxymethyl-1-piperazinyl, 3-hydroxymethyl-1-piperazinyl, 4-ethyl-3-(2-hydroxyethyl)-1-piperazinyl, 3-(3-hydroxypropyl)-1-piperazinyl, 4-methyl-2-(4-hydroxybutyl)-1-piperazinyl, 4-ethyl-3-(5-hydroxypentyl)-1-piperazinyl, 3-(6-hydroxyhexyl)-1-piperazinyl, 4-(4-methoxybenzyl)-1-piperazinyl, 4-(3-ethoxybenzyl)-1-piperazinyl, 4-(2-propoxybenzyl)-1-piperazinyl, 4-(4-n-butoxybenzyl)-1-piperazinyl, 4-(3-pentyloxybenzyl)-1-piperazinyl, 4-(2-hexyloxybenzyl)-1-piperazinyl, 4-(4-nitrobenzyl)-1-piperazinyl, 4-(3-nitrobenzyl)-1-piperazinyl, 4-(4-aminobenzyl)-1-piperazinyl, 4-(2-aminobenzyl)-1-piperazinyl, 4-cyclopropyl-1-piperazinyl, 4-cyclobutyl-1-piperazinyl, 4-cyclopentyl-1-piperazinyl, 4-cyclohexyl-1-piperazinyl, 4-cycloheptyl-1-piperazinyl, 4-cyclooctyl-1-piperazinyl, 4-phenyl-1-piperazinyl, 4-(4-fluorophenyl)-1-piperazinyl, 4-(3-bromophenyl)-1-piperazinyl, 4-(2-chlorophenyl)-1-piperazinyl, 4-(4-iodophenyl)-1-piperazinyl, 4-(4-methylphenyl)-1-piperazinyl, 4-(3-ethylphenyl)-1-piperazinyl, 4-(2-propylphenyl)-1-piperazinyl, 4-(4-n-butylphenyl)-1-piperazinyl, 4-(3-pentylphenyl)-1-piperazinyl, 4-(2-hexylphenyl)-1-piperazinyl, 4-(4-trifluoromethylphenyl)-1-piperazinyl, 4-[3-(2-chloroethyl)phenyl]-1-piperazinyl, 4-[2-(3,3-dibromopropyl)phenyl]-1-piperazinyl, 4-[4-(4-chlorobutyl)phenyl]-1-piperazinyl, 4-hydroxymethyl-1-piperazinyl, 4-(2-hydroxyethyl)-1-piperazinyl, 4-(3-hydroxypropyl)-1-piperazinyl, 4-(3-chloropropyl)-1-piperazinyl, 4-(bromomethyl)-1-piperazinyl, 4-(2-fluoroethyl)-1-piperazinyl, 4-(4-chlorobutyl)-1-piperazinyl 4-(3-fluoropentyl)-1-piperazinyl, 4-(2,3-dichlorohexyl)-1-piperazinyl, 4-(2,2,2-trifluoroethyl)-1-piperazinyl, 4-(trifluoromethyl)-1-piperazinyl, 4-aminomethyl-1-piperazinyl, 4-(3-dimethylaminopropyl)-1-piperazinyl, 4-(2-ethylaminoethyl)-1-piperazinyl, 4-(4-propylaminobutyl)-1-piperazinyl, 4-(5-n-butylaminopentyl)-1-piperazinyl, 4-(6-pentylaminohexyl)-1-piperazinyl, 4-(N-methyl-N-ethylaminomethyl)-1-piperazinyl, 4-(N-methyl-N-propylaminomethyl)-1-piperazinyl, 4-(2-diethylaminoethyl)-1-piperazinyl, 4-(methoxymethyl)-1-piperazinyl, 4-(ethoxymethyl)-1-piperazinyl, 4-(2-propoxyethyl)-1-piperazinyl, 4-(3-butoxypropyl)-1-piperazinyl, 4-(4-pentyloxybutyl)-1-piperazinyl, 4-(5-hexyloxypentyl)-1-piperazinyl, 4-(6-methoxyhexyl)-1-piperazinyl, 4-propargyl-piperazinyl, 4-(2-butynyl)-1-piperazinyl, 4-(3-butynyl)-1-piperazinyl, 4-(1-methyl-2-propynyl)-1-piperazinyl, 4-(2-pentynyl)-1-piperazinyl, 4-(2-hexynyl)-1-piperazinyl, 4-ethynyl-1-piperazinyl, 4-vinyl-1-piperazinyl, 4-allyl-1-piperazinyl, 4-(2-butenyl)-1-piperazinyl, 4-(3-butenyl)-1-piperazinyl, 4-(1-methylallyl)-1-piperazinyl, 4-(2-pentenyl)-1-piperazinyl, 4-(2-hexenyl)-1-piperazinyl, 2-oxo-1-piperazinyl, 3-oxo-1-piperazinyl, 4-oxo-3-methyl-1-piperazinyl, 4,4-dimethyl-1-piperazinyl, 4-(2-pyridyl)-1-piperazinyl, 4-(3-pyridyl)-1-piperazinyl, 4-(4-pyridyl)-1-piperazinyl, 4-carbamoyl-1-piperazinyl, 4-dimethylaminocarbonyl-1-piperazinyl, 4-ethylaminocarbonyl-1-piperazinyl, 4-propylaminocarbonyl-1-piperazinyl, 4-butylaminocarbonyl-1-piperazinyl, 4-pentylaminocarbonyl-1-piperazinyl, 4-hexylaminocarbonyl-1-piperazinyl, 4-diethylaminocarbonyl-1-piperazinyl, 4-(N-methyl-N-propylaminocarbonyl)-1-piperazinyl, 4-methoxycarbonyl-1-piperazinyl, 4-ethoxycarbonyl-1-piperazinyl, 4-propoxycarbonyl-1-piperazinyl, 4-tert-butoxycarbonyl-1-piperazinyl, 4-pentyloxycarbonyl-1-piperazinyl, 4-hexyloxycarbonyl-1-piperazinyl, 4-benzyloxycarbonyl-1-piperazinyl, 4-(2-phenylethoxycarbonyl)-1-piperazinyl, 4-(3-phenylpropoxycarbonyl)-1-piperazinyl, 4-(4-phenylbutoxycarbonyl)-1-piperazinyl, 4-(5-phenylpentyloxycarbonyl)-1-piperazinyl, 4-(6-phenylhexyloxycarbonyl)-1-piperazinyl, 4-(2-aminoacetyl)-1-piperazinyl, 4-(3-aminopropionyl)-1-piperazinyl, 4-(4-aminobutyryl)-1-piperazinyl, 4-(5-aminopentanoyl)-1-piperazinyl, 4-(6-aminohexanoyl)-1-piperazinyl, 4-(2-benzyloxycarbonylaminoacetyl)-1-piperazinyl, 4-[2-(2-phenylethoxycarbonylamino)acetyl]-1-piperazinyl, 4-[2-(3-phenylpropoxycarbonylamino)acetyl]-1-piperazinyl, 4-[2-(4-phenylbutoxycarbonylamino)acetyl]-1-piperazinyl, 4-methoxycarbonylmethyl-1-piperazinyl, 4-ethoxycarbonylmethyl-1-piperazinyl, 4-(2-ethoxycarbonylethyl)-1-piperazinyl, 4-(3-propoxycarbonylpropyl)-1-piperazinyl, 4-(4-butoxycarbonylbutyl)-1-piperazinyl, 4-(5-pentyloxycarbonylpentyl)-1-piperazinyl, 4-(6-hexyloxycarbonylhexyl)-1-piperazinyl, 4-carbonylmethyl-1-piperazinyl, 4-(2-carboxyethyl)-1-piperazinyl, 4-(3-carboxypropyl)-1-piperazinyl, 4-(4-carboxybutyl)-1-piperazinyl, 4-(5-carboxypentyl)-1-piperazinyl, 4-(6-carboxyhexyl)-1-piperazinyl, 4-(anilinocarbonylmethyl)-1-piperazinyl, 4-(2-anilinocarbonylethyl)-1-piperazinyl, 4-(3-anilinocarbonylpropyl)-1-piperazinyl, 4-(4-anilinocarbonylbutyl)-1-piperazinyl, 4-(5- anilinocarbonylpentyl)-1-piperazinyl, 4-(6-anilinocarbonylhexyl)-1-piperazinyl, 4-(3-carboxyacryloyl)-1-piperazinyl, 4-(3-carboxy-2,3-dichloroacryloyl)-1-piperazinyl, 4-methyl-1-piperidinyl, 4-ethyl-1-piperidinyl, 4-propyl-1-piperidinyl, 4-n-butyl-1-piperidinyl, 4-pentyl-1-piperidinyl, 4-hexyl-1-piperidinyl, 4-methoxy-1-piperidinyl, 4-ethoxy-1-piperidinyl, 4-propoxy-1-piperidinyl, 4-n-butoxy-1-piperidinyl, 4-pentyloxy-1-piperidinyl, 4-hexyloxy-1-piperidinyl, 4-acetyloxy-1-piperidinyl, 4-propionyloxy-1-piperidinyl, 4-butyryloxy-1-piperidinyl, 4-pentanoyloxy-1-piperidinyl, 4-hexanoyloxy-1-piperidinyl, 4-methoxycarbonyloxy-1-piperidinyl, 4-ethoxycarbonyl-1-piperidinyl, 4-propoxycarbonyl-1-piperidinyl, 4-n-butoxycarbonyl-1-piperidinyl, 4-pentyloxycarbonyl-1-piperidinyl, 4-hexyloxycarbonyl-1-piperidinyl, 4-benzyl-1-piperidinyl, 4-(2-phenylethyl)-1-piperidinyl, 4-(1-phenylethyl)-1-piperidinyl, 4-(3-phenylpropyl)-1-piperidinyl, 4-(4-phenylbutyl)-1-piperidinyl, 4-(5-phenylpentyl)-1-piperidinyl, 4(6-phenythexyl)-1-piperidinyl, 4-hydroxy-1-piperidinyl, 3-hydroxy-1-piperidinyl, 2-hydroxy-1-piperidinyl, 4-amino-1-piperidinyl, 3-amino-1-piperidinyl, 2-amino-1-piperidinyl, 4-dimethylamino-1-piperidinyl, 4-methylamino-1-piperidinyl, 3-ethylamino-1-piperidinyl, 2-propylamino-1-piperidinyl, 4-n-butylamino-1-piperidinyl, 3-pentylamino-1-piperidinyl, 4-hexylamino-1-piperidinyl, 3-diethylamino-1-piperidinyl, 4-(N-methyl-N-propylamino)-1-piperidinyl, 4-carbamoyl-1-piperidinyl, 3-carbamoyl-1-piperidinyl, 3,5-dimethyl-1-piperidinyl, 2,5-dimethyl-1-piperidinyl, 4-oxo-1-piperidinyl, 3-oxo-1-piperidinyl, 3-hydroxy-1-pyrrolidinyl, 3-amino-1-pyrrolidinyl, 2-hydroxy-1-pyrrolidinyl, 2-amino-1-pyrrolidinyl, 3-methylamino-1-pyrrolidinyl, 3-dimethylamino-1-pyrrolidinyl, 2-ethylamino-1-pyrrolidinyl, 3-propylamino-1-pyrrolidinyl, 2-n-butylamino-1-pyrrolidinyl, 3-pentylamino-1-pyrrolidinyl, 2-hexylamino-1-pyrrolidinyl, 3-diethylamino-1-pyrrolidinyl, 3-(N-methyl-N-propylamino)-1-pyrrolidinyl, 2-(N-ethyl-N-n-butylamino)-1-pyrrolidinyl, 3-acetylamino-1-pyrrolidinyl, 3-propionylamino-1-pyrrolidinyl, 2-butyrylamino-1-pyrrolidinyl, 3-pentanoylamino-1-pyrrolidinyl, 2-hexanoylamino-1-pyrrolidinyl, 3-hydroxymethyl-1-pyrrolidinyl, 2-(2-hydroxyethyl)-1-pyrrolidinyl, 3-(3-hydroxypropyl)-1-pyrrolidinyl, 2-(4-hydroxybutyl)-1-pyrrolidinyl, 3-(5-hydroxypentyl)-1-pyrrolidinyl, 3-(6-hydroxyhexyl)-1-pyrrolidinyl, 3-aminomethyl-1-pyrrolidinyl, 3-(2-aminoethyl)-1-pyrrolidinyl, 2-(3-aminopropyl)-1-pyrrolidinyl, 3-(4-aminobutyl)-1-pyrrolidinyl, 3-(5-aminopentyl)-1-pyrrolidinyl, 3-(6-aminohexyl)-1-pyrrolidinyl, 3-(methylaminomethyl)-1-pyrrolidinyl, 3-(2-ethylaminoethyl)-1-pyrrolidinyl, 3-(3-propylaminopropyl)-1-pyrrolidinyl, 2-(4-n-butylaminobutyl)-1-pyrrolidinyl, 3-(5-pentylaminopentyl)-1-pyrrolidinyl, 3-(6-hexylaminohexyl)-1-pyrrolidinyl, 3-(dimethylaminomethyl)-1-pyrrolidinyl, 2-(N-methyl-N-ethylaminomethyl)-1-pyrrolidinyl, 3-(N-ethyl-N-n-butylaminomethyl)-1-pyrrolidinyl, 3-methylaminomethyl-4-methyl-1-pyrrolidinyl, 3-methylaminomethyl-4-fluoro-1-pyrrolidinyl, 3-methylamino-4-methyl-1-pyrrolidinyl, 3-methylamino-4-chloro-1-pyrrolidinyl, 3-methylaminomethyl-4-chloro-1-pyrrolidinyl, 3-methylamino-4-fluoro-1-pyrrolidinyl, 3-ethylaminomethyl-4-ethyl-1-pyrrolidinyl, 4-propylaminomethyl-2-propyl-1-pyrrolidinyl, 4-n-butylaminomethyl-2-fluoro-1-pyrrolidinyl, 4-pentylaminomethyl-2-n-butyl-1-pyrrolidinyl, 4-hexylaminomethyl-2-chloro-1-pyrrolidinyl, 4-propylamino-2-chloro-1-pyrrolidinyl, 4-n-butylamino-2-hexyl-1-pyrrolidinyl, 3-pentylamino-4-ethyl-1-pyrrolidinyl, 3-hexylamino-4-fluoro-1-pyrrolidinyl, 4-methyl-1-homopiperazinyl, 4-ethyl-1-homopiperazinyl, 4-propyl-1-homopiperazinyl, 4-n-butyl-1-homopiperazinyl, 4-pentyl-1-homopiperazinyl, 4-hexyl-1-homopiperazinyl, 4-formyl-1-homopiperazinyl, 4-acetyl-1-homopiperazinyl, 4-propionyl-1-homopiperazinyl, 4-butyryl-1-homopiperazinyl, 4-pentanoyl-1-homopiperazinyl, 4-hexanoyl-1-homopiperazinyl, 2-methyl-1-hexahydropyridazyl, 2-ethyl-1-hexahydropyridazyl, 2-propyl-1-hexahydropyridazyl, 2-n-butyl-1-hexahydropyridazyl, 2-pentyl-1-hexahydropyridazyl, 2-hexyl-1-hexahydropyridazyl, 2-formyl-1-hexahydropyridazyl, 2-acetyl-1-hexahydropyridazyl, 2-propionyl-1-hexahydropyridazyl, 2-butyryl-1-hexahydropyridazyl, 2-pentanoyl-1-hexahydropyridazyl, 2-hexanoyl-1-hexahydropyridazyl, 2-methyl-1-pyrazolidinyl, 2-ethyl-1-pyrazolidinyl, 2-propyl-1-pyrazolidinyl, 2-n-butyl-1-pyrazolidinyl, 2-pentyl-1-pyrazolidinyl, 2-hexyl-1-pyrazolidinyl, 2-formyl-1-pyrazolidinyl, 2-acetyl-1-pyrazolidinyl, 2-propionyl-1-pyrazolidinyl, 2-butyryl-1-pyrazolidinyl, 2-pentanoyl-1-pyrazolidinyl, 2-hexanoyl-1-pyrazolidinyl, 3,5-dimethylmorpholino, 3-methylmorpholino, 3-ethylmorpholino, 2-propylmorpholino, 3-n-butylmorpholino, 3-pentyl-5-methylmorpholino, 3-hexyl-5-ethylmorpholino, 3-aminomethylmorpholino, 3-methylaminomethylmorpholino, 2-ethylaminomethylmorpholino, 3-propylaminomethylmorpholino, 3-n-butylaminomethylmorpholino, 2-pentylaminomethylmorpholino, 3-hexylaminomethylmorpholino, 3-(2-methylaminoethyl)-morpholino, 3-(3-methylaminopropyl)morpholino, 3-(4-methylaminobutyl)morpholino, 2-(5-methylaminopentyl)-morpholino, 3-(6-methylaminohexyl)morpholino, 4-(5-methyl-2-oxo-1,3-dioxolen-4-yl)methyl-1-piperazinyl, 4-(5-tert-butyl-2-oxo-1,3-dioxolen-4-yl)methyl-1-piperazinyl, 4-(5-phenyl-2-oxo-1,3-dioxolen-4-yl)methyl-1-piperazinyl, 4-(2-oxo-1,3-dioxolen-4-yl)methyl-1-piperazinyl, 3-(5-methyl-2-oxo-1,3-dioxolen-4-yl)methylamino-1-pyrrolidinyl, 4-(5-methyl-2-oxo-1,3-dioxolen-4-yl)methylamino-1-piperidinyl, 3-(5-phenyl-2-oxo-1,3-dioxolen-4-yl)methylaminomorpholino, 3,5-dimethyl-1-piperazinyl, 3,3-dimethyl-1-piperazinyl, 4-acetyl-3-methyl-1-piperazinyl, 3-ethyl-1-piperazinyl, 3-ethyl-4-methyl-1-piperazinyl, 3-trifluoromethyl-1-piperazinyl, 3-(fluoromethyl)-1-piperazinyl, 3-methylthio-1-piperazinyl, 4-methylthio-1-piperazinyl, 3-ethylthio-1-piperazinyl, 3-methylthiomorpholino, 4-fluoro-1-piperidinyl, 3-fluoro-1-piperidinyl, 3-chloro-1-piperazinyl, 3-amino-4-fluoro-1-pyrrolidinyl, 3-amino-4-hydroxy-1-pyrrolidinyl, 3-amino-4-methoxy-1-pyrrolidinyl, 3-amino-4-fluoro-1-piperidinyl, 3-amino-4-hydroxy-1-piperidinyl, 3-amino-4-methyl-1-pyrrolidinyl, 4-benzyl-3-methyl-1-piperazinyl, 3-fluoromethylmorpholino, 3-chloromethylmorpholino, 4-oxo-1-piperidinyl, 3-oxo-1-piperidinyl, 2-oxo-1-piperidinyl, 3-acetylaminomethyl-1-pyrrolidinyl, 3-(N-ethyl-N-acetylamino)-methyl-1-pyrrolidinyl, 3-t-butoxycarbonylaminomethyl-1-pyrrolidinyl, 3-ethylaminomethyl-1-pyrrolidinyl, 4-cyclopropylamino-1-piperazinyl, 3-cyclopropylamino-1-pyrrolidinyl, 4-cyclopentylamino-1-piperazinyl, 4-cyclohexylamino-1-piperazinyl, 3-cycloheptylamino-1-pyrrolidinyl, 4-cyclooctylamino-1-piperidinyl, 4-cyclopropylamino-1-piperidinyl, 3-cyclopropylaminomorpholino, 4-thio-1-piperidinyl, 3-thio-1-piperazinyl, 3-thiomorpholino, 4-cyclopropylaminomethyl-1-piperazinyl, 3-cyclopropylaminomethyl-1-pyrrolidinyl, 4-cyclopropylaminomethyl-1-piperidinyl, 3-cyclopropylaminomethylmorpholino, 4-(2-cyclopentylaminoethyl)-1-piperazinyl, 4-(3-cyclohexylaminopropyl)-1-piperazinyl, 3-(4-cyclobutyl-aminobutyl)-1-pyrrolidinyl, 4-(5-cyclooctylaminopentyl)-1-piperidinyl, 4-(6-cyclopropylaminohexyl)morpholino, 3-acetylaminomethyl-1-pyrrolidinyl, 4-(2- propionylaminoethyl)-1-piperazinyl, 4-(3-butyrylaminopropyl)-1-piperidinyl, 3-(4-pentanoylaminobutyl)morpholino, 4-(5-hexanoylaminopentyl)-1-piperazinyl, 3-(6-acetylaminohexyl)-1-pyrrolidinyl, 4-(N-acetyl-N-ethylamino)methyl-1-piperazinyl, 4-(N-cyclopropyl-N-acetylamino)methyl-1-pyrrolidinyl, 4-(methoxycarbonylaminomethyl)-1-piperazinyl, 4-(2-ethoxycarbonylaminoethyl)-1-piperidinyl, 3-(3-propoxycarbonylaminopropyl)morpholino, 3-(4-pentyloxycarbonylaminobutyl)-1-pyrrolidinyl, 3-(5-hexyloxycarbonylaminopentyl)-1-pyrrolidinyl, 4-(6-t-butoxy-carbonylaminohexyl)-1-piperazinyl, 3-(N-t-butoxycarbonyl-N-ethylaminomethyl)-1-pyrrolidinyl, 3-(N-t-butoxycarbonyl-N-methylaminomethyl)-1-pyrrolidinyl, 3-(N-t-butoxycarbonyl-N-cyclopropylaminomethyl)-1-pyrrolidinyl, 4-(N-methoxy-carbonyl-N-cyclopropylaminomethyl)-1-piperazinyl and 4-(N-propoxycarbonyl-N-cyclohexylaminomethyl)-1-piperidinyl. The term "a 5- to 9-membered saturated or unsaturated heterocyclic ring which may be substituted" also includes the group represented by the formula:

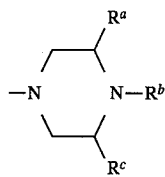

wherein $R^a$ is hydrogen atom or a (lower) alkyl, $R^b$ is hydrogen atom, a (lower) alkyl, a (lower) alkanoyl, a phenyl(lower)alkyl, or a 2-oxo-1,3-dioxolenemethyl which is substituted by a (lower) alkyl, and $R^c$ is hydrogen atom or a (lower) alkyl; the group represented by the formula:

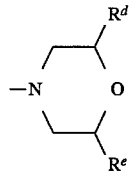

wherein $R^d$ is hydrogen atom or a (lower) alkyl, and $R^e$ is hydrogen atom or a (lower) alkyl; the group represented by the formula:

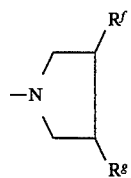

wherein $R^f$ is an amino which may be substituted by 1 or 2 substituents selected from the group consisting of a (lower) alkyl and a (lower) alkoxycarbonyl, or a amino(lower)alkyl which may be substituted by 1 or 2 substituents selected from the group consisting of a (lower) alkyl and a (lower) alkoxycarbonyl, $R^g$ is hydrogen atom or a (lower) alkyl; the group represented by the formula:

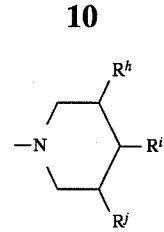

wherein $R^h$ is hydrogen atom or a (lower) alkyl, $R^i$ is hydrogen atom, hydroxy, a halogen atom or oxo, and $R^j$ is hydrogen atom or a (lower) alkyl; and the like.

The term "a cycloalkyl" includes $C_3$–$C_8$ cycloalkyl such as cyclopropyl, cyclobutyl, cyclopentyl, cyclohexyl, cycloheptyl or cyclooctyl.

The term "a phenyl (lower) alkyl in which phenyl ring may be substituted by a (lower) alkoxy, nitro or amino" includes phenylalkyl in which the phenyl ring may be substituted by a straight chain or branched chain $C_1$–$C_6$ alkoxy, nitro or amino and the alkyl moiety is a straight chain or branched chain $C_1$–$C_6$ alkyl, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 4-methoxybenzyl, 3-ethoxybenzyl, 2-propoxybenzyl, 4-n-butoxybenzyl, 3-pentyloxybenzyl, 2-hexyloxybenzyl, 4-nitrobenzyl, 3-nitrobenzyl, 4-aminobenzyl, 2-aminobenzyl, 2-(4-methoxyphenyl)ethyl, 1-(3-ethoxyphenyl)ethyl, 3-(2-propoxyphenyl)propyl, 4-(4-n-butoxyphenyl)butyl, 5-(2-nitrophenyl)pentyl or 6-(3-aminophenyl)hexyl.

The term "a phenyl which may be substituted by a halogen atom or a (lower).alkyl which may be substituted by 1 to 3 of halogen atoms" includes phenyl in which the phenyl ring may be substituted by a halogen atom or by a straight chain or branched chain $C_1$–$C_6$ alkyl which may be substituted by 1 to 3 of halogen atoms, such as phenyl, 4-fluorophenyl, 3-bromophenyl, 2-chlorophenyl, 4-iodophenyl, 4-methylphenyl, 3-ethylphenyl, 2-propylphenyl, 4-n-butylphenyl, 3-pentylphenyl, 2-hexylphenyl, 4-trifluoromethylphenyl, 3-(2-chloroethyl)phenyl, 2-(3,3-dibromopropyl)phenyl, 4-(4-chlorobutyl)phenyl, 3-(5-iodopentyl)phenyl, 4-(6-fluorohexyl)phenyl, 2-(1,2,2-trifluoroethyl)phenyl or 4-(2,2,2-trifluoroethyl)phenyl.

The term "a (lower) alkyl having 1 to 3 of substituents selected from the group consisting of hydroxy, an amino which may be substituted by a (lower) alkyl, a (lower) alkanoyl, a cycloalkyl or a (lower) alkoxycarbonyl, a (lower) alkoxy and a halogen atom" includes a straight chain or branched chain $C_1$–$C_6$ alkyl having 1 to 3 of substituents selected from the group consisting of hydroxy; an amino which may be substituted by 1 or 2 substituents selected from the group consisting of a straight chain or branched chain $C_1$–$C_6$ alkyl, a straight chain or branched chain $C_1$–$C_6$ alkanoyl, a $C_3$–$C_8$ cycloalkyl and a straight chain or branched chain ($C_1$–$C_6$)alkoxy-carbonyl; a straight chain or branched chain $C_1$–$C_6$ alkoxy and a halogen atom, such as hyroxymethyl, 2-hydroxyethyl, 1-hyroxyethyl, 3-hydroxypropyl, 4-hydroxybutyl, 5-hyroxypentyl, 6-hydroxyhexyl, 3-chloropropyl, bromomethyl, 2-fluoroethyl, 4-chlorobutyl, 3-fluoropentyl, 2,3-dichlorohexyl, 2,2,2-trifluoroethyl, trifluoromethyl, aminomethyl, 2-aminoethyl, 1-aminoethyl, 3-aminopropyl, 4-aminobutyl, 5-aminopentyl, 6-aminohexyl, 3-dimethylaminopropyl, 2-ethylaminoethyl, 4-propylaminobutyl, 5-n-butylaminopentyl, 6-pentylaminohexyl, methylaminomethyl, diethylaminomethyl, 2-dipropylaminoethyl, 1-di-n-butylaminoethyl, 3-dipentylaminopropyl, 4-dihexylaminobutyl, N-methyl-N-ethylaminomethyl, N-methyl-N-propylaminomethyl, methoxymethyl, ethoxymethyl, 2-propoxyethyl, 3-butoxypropyl, 4-pentyloxybutyl, 5-hexyloxypentyl, 6-methoxyhexyl, propoxymetyl, 1-ethoxyethyl, 2-hexyloxyethyl, formylaminomethyl, acetylaminomethyl, 2-propanoylaminoethyl, 3-butyrylaminopropyl, 4-pentanoylaminobutyl, 5-hexanoylaminopentyl, 6-acetylaminohexyl, propanoylaminomethyl, 1-acetylaminoethyl, 2-hexanoylaminoethyl, N-acetyl-N-methylaminomethyl, N-acetyl-N-ethylaminomethyl, N-acetyl-N-cyclopropylaminomethyl, N,N-dicyclopropylaminomethyl, cyclopropylaminomethyl, 2-cyclobutylaminoethyl, 3-cyclo-pentylaminopropyl, 1-cyclopropylaminoethyl, 2-cyclopropylaminoethyl, aminopropyl, 4-cyclohexylaminobutyl, 5-cycloheptylaminopentyl, 6-cyclooctylaminohexyl, N-methyl-N-cyclopropylaminomethyl, N-ethyl-N-cyclopropylaminomethyl, methoxycarbonylaminomethyl, 2-ethoxycarbonylaminoethyl, 3-propoxycarbonylaminopropyl, 4-t-butoxycarbonylaminobutyl, 5-pentyloxycarbonylaminopentyl, 6-hexyloxycarbonylaminohexyl, t-butoxycarbonylaminomethyl, 2-t-butoxycarbonylaminoethyl, 1-t-butoxycarbonylaminoethyl, N-t-butoxycarbonyl-N-methylaminomethyl, N-t-butoxycarbonyl-N-ethylaminomethyl or N-t-butoxycarbonyl-N-cyclopropylaminomethyl.

The term "a (lower) alkanoyl which may be substituted by 1 to 7 of halogen atoms" includes a straight chain or branched chain $C_1$–$C_6$ alkanoyl which may be substituted by 1 to 7 of halogen atoms, such as formyl, acetyl, propionyl, butyryl, pentanoyl, hexanoyl, α,α,α-trifluoroacetyl, ββ,β-difluoro-α,α-difluoropropionyl, γ,γ,γ-trifluoro-β,β-difluoro-α,α-difluorobutyryl, α,α-dichloroacetyl, α-bromoacetyl, α-iodoacetyl, β-fluoropropionyl, β-fluoro-α-fluoropropionyl, 6-fluorohexanoyl or 4-chloropentanoyl, 3,3,3-trifluoropropionyl.

The term "a (lower) alkenylcarbonyl having 1 to 3 substituents selected from the group consisting of a halogen atom and a carboxy" includes a straight chain or branched chain ($C_2$–$C_6$)alkenyl-carbonyl having 1 to 3 of substituents selected from the group consisting of a halogen atom and a carboxy, such as 3-carboxyacryloyl, 3-carboxy-2,3-dichloroacryloyl, 3-carboxy-2,3-dibromoacryloyl, 4-carboxycrotonoyl, 4-carboxyisocrotonoyl, 5-carboxy-3-pentenoyl, 6-carboxy-4-hexenoyl, 4-carboxy-3-fluorocrotonoyl or 5-carboxy-3,4-dichloro-3-hexenoyl.

The term "a (lower) alkoxycarbonyl" includes a straight chain or branched chain ($C_1$–$C_6$)alkoxy-carbonyl, such as methoxycarbonyl, ethoxycarbonyl, propoxycarbonyl, isopropoxycarbonyl, butoxycarbonyl, tert-butoxycarbonyl, pentyloxycarbonyl or hexyloxycarbonyl.

The term "an aminocarbonyl which may be substituted by a (lower) alkyl" includes aminocarbonyl which may be substituted by 1 or 2 of a straight chain or branched chain $C_1$–$C_6$ alkyl, such as carbamoyl, methylaminocarbonyl, ethylaminocarbonyl, propylaminocarbonyl, n-butylaminocarbonyl, pentylaminocarbonyl, hexylaminocarbonyl, dimethylaminocarbonyl, diethylaminocarbonyl, dipropylaminocarbonyl, dipentylaminocarbonyl, dihexylaminocarbonyl, N-methyl-N-propylaminocarbonyl, N-methyl-N-tert-butylaminocarbonyl or N-ethyl-N-pentylaminocarbonyl.

The term "a phenyl(lower)alkoxycarbonyl" includes phenylalkoxycarbonyl in which alkoxy moiety is a straight chain or branched chain $C_1$–$C_6$ alkoxy, such as benzyloxycarbonyl, 2-phenylethoxycarbonyl, 1-phenylethoxycarbonyl, 3-phenylpropoxycarbonyl, 4-phenylbutoxycarbonyl, 1,1-dimethyl-2-phenylethoxycarbonyl, 5-phenylpentyloxycarbonyl, 6-phenylhexyloxycarbonyl or 2-methyl-3-phenylpropoxycarbonyl.

The term "an amino(lower)alkanoyl which may be substituted by a phenyl(lower)alkoxycarbonyl" includes a straight chain or branched chain $C_2$–$C_6$ aminoalkanoyl which may be substituted by a phenylalkoxycarbonyl in which alkoxy moiety is a straight chain or branched chain $C_1$–$C_6$ alkoxy, such as 2-aminoacetyl, 3-aminopropionyl, 4-aminobutyryl, 5-aminopentanoyl, 6-aminohexanoyl, 2-benzyloxycarbonylaminoacetyl, 2-(2-phenylethoxycarbonylamino)acetyl, 2-(3-phenylpropoxycarbonylamino)acetyl, 3-(4-phenylbutoxycarbonylamino)propionyl, 4-(1,1-dimethyl-2-phenylethoxycarbonylamino)butyryl, 5-(5-phenylpentyloxycarbonylamino)pentanoyl, 6-(6-phenylhexyloxycarbonylamino)hexanoyl or 2-(2-methyl-3-phenylpropoxycarbonylamino)acetyl.

The term "a (lower) alkoxycarbonyl(lower)alkyl" includes alkoxycarbonylalkyl in which alkoxy and alkyl moieties are a straight chain or branched chain $C_1$–$C_6$ alkoxy and alkyl, respectively, such as methoxycarbonylmethyl, ethoxycarbonylmethyl, 2-ethoxycarbonylethyl, 3-propoxycarbonylpropyl, 4-butoxycarbonylbutyl, 5-pentyloxycarbonylpentyl, 6-hexyloxycarbonylhexyl, 2-methoxycarbonylmethyl, 3-methoxycarbonylpropyl, 3-ethoxycarbonylpropyl or 4-ethoxycarbonybutyl.

The term "a carboxy(lower)alkyl" includes carboxyalkyl in which the alkyl moiety is a straight chain or branched chain $C_1$–$C_6$-alkyl, such as carboxymethyl, 2-carboxyethyl, 3-carboxypropyl, 4-carboxybutyl, 5-carboxypentyl, 6-carboxyhexyl, 1-carboxyethyl, 1,1-dimethyl-2-carboxyethyl or 2-methyl-3-carboxypropyl.

The term "an anilinocarbonyl (lower)alkyl" includes anilinocarbonylalkyl in which the alkyl moiety is a straight chain or branched chain $C_1$–$C_6$ alkyl, such as anilinocarbonylmethyl, 2-anilinocaronylethyl, 1-anilinocarbonylethyl, 3-anilinocarbonylpropyl, 4-anilinocarbonylbutyl, 5-anilinocarbonylpentyl, 6-anilinocarbonylhexyl, 1,1-dimethyl-2-anilinocarbonylethyl or 2-methyl-3-anilinocarbonylpropyl.

The term "an amino which may be substituted by a (lower) alkyl, a (lower) alkanoyl, a (lower) alkoxycarbonyl or a phenyl(lower)alkyl" includes amino which may be substituted by 1 or 2 of a straight chain or branched chain $C_1$–$C_6$ alkyl, a straight chain or branched chain $C_1$–$C_6$-alkanoyl, a straight chain or branched chain ($C_1$–$C6$)alkoxycarbonyl or a phenylalkyl in which the alkyl moiety is a straight chain or branched chain $C_1$–$C_6$ alkyl, such as amino, methylamino, ethylamino, propylamino, t-butylamino, pentylamino, hexylamino, dimethylamino, diethylamino, di-n-propylamino, di-n-butylamino, dipentylamino, dihexylamino, N-methyl-N-n-butylamino, N-methyl-N-pentylamino, N-ethyl-N-hexylamino, acetylamino, formylamino, propionylamino, butyrylamino, pentanoylamino, hexanoylamino, N-methyl-N-acetylamino, N-ethyl-N-propionylamino, N-methyl-N-butyryl-amino, N-n-propyl-N-pentanoylamino, N-ethyl-N-hexanoylamino, methoxycrbonylamino, ethoxycarbonylamino, propoxycarbonylamino, t-butoxycarbonylamino, pentyloxycarbonylamino, hexyloxycarbonylamino, butoxycarbonylamino, N-t-butoxycarbonyl-N-methylamino, N-t-butoxycarbonyl-N-ethylamino, N-t-butoxycarbonyl-N-benzylamino, benzylamino, (2-phenylethyl)amino, (1-phenylethyl)amino, (3-phenylpropyl)amino, (4-phenylbutyl)amino, (5-phenylpentyl)amino or (6-phenylhexyl)amino.

The term "a 2(5H)-furanone which may be substituted by 1 or 2 of halogen atoms" includes 2(5H)-furanone which may be substituted by 1 or 2 of halogen atoms, such as 2(5H)-furanon-5-yl, 3,4-dibromo-2(5H)-furanon-5-yl, 3,4-dichloro-2(5H)-furanon-5-yl, 3-chloro-2(5H)-furanon-5-yl, 4-fluoro-2(5H)-furanon-5-yl or 3-iodo-2(5H)-furanon-5-yl.

The term "a sulfo(lower)alkyl" includes sulfoalkyl in which the alkyl moiety is a straight chain or branched chain $C_1$–$C_6$alkyl, such as sulfomethyl, 2-sulfoethyl, 1-sulfoethyl, 3-sulfopropyl, 4-sulfobutyl, 5-sulfopentyl, 6-sulfo-hexyl, 1,1-dimethyl-2-sulfoethyl or 2-methyl-3-sulfopropyl.

The term "a (lower) alkylsulfonyl which may be substituted by 1 to 3 of halogen atoms" includes a straight chain or branched chain $C_1$–$C_6$ alkylsulfonyl which may be substituted by 1 to 3 of halogen atoms, such as methylsulfonyl, ethylsulfonyl, isopropylsulfonyl, n-butylsulfonyl, pentylsulfonyl, hexylsulfonyl, trifluoromethylsufonyl, 2-fluoroethylsulfonyl, 3-fluoropropylsulfonyl, 4,4,4-trifluorobutylsulfonyl, 5-chloropentylsulfonyl, 6-bromohexylsulfonyl, 6-iodohexylsulfonyl, 2,2-difluoroethylsulfonyl or 2,3-dibromopropylsulfonyl.

The term "a (lower) alkoxy" includes a straight chain or branched chain $C_1$–$C_6$ alkoxy, such as methoxy, ethoxy, propoxy, isopropoxy, butoxy, tert-butoxy, pentyloxy or hexyloxy.

The term "a (lower) alkanoyloxy" includes a straight chain or branched chain $C_2$–$C_6$ alkanoyloxy, such as acetyloxy, propionyloxy, butyryloxy, isobutyryloxy, pentanoyloxy or hexanoyloxy.

The term "a (lower) alkenyl" includes a straight chain or branched chain $C_2$–$C_6$ alkenyl, such as vinyl, allyl, 2-butenyl, 3-butenyl, 1-methylallyl, 2-pentenyl or 2-hexenyl.

The term "a (lower) alkynyl" includes a straight chain or branched chain $C_2$–$C_6$ alkynyl, such as ethynyl, 2-propynyl, 2-butynyl, 3-butynyl, 1-methyl-2-propynyl, 2-pentynyl or 2-hexynyl.

The term "a 2-oxo-1,3-dioxolenemethyl which may be substituted by phenyl or a (lower) alkyl" includes 2-oxo-1,3-dioxolenemethyl which may be substituted by phenyl or a straight chain or branched chain $C_1$–$C_6$ alkyl, such as (5-methyl-2-oxo-1,3-dioxolen-4-yl)methyl, (5-tert-butyl-2-oxo-1,3-dioxolen-4-yl)methyl, (5-phenyl-2-oxo-1,3-dioxolen-4-yl)methyl, (2-oxo-1,3-dioxolen-4-yl)methyl, (5-pentyl-2-oxo-1,3-dioxolen-4-yl)methyl, (5-hexyl-2-oxo-1,3-dioxolen-4-yl)-methyl, (5-ethyl-2-oxo-1,3-dioxolen-4-yl)methyl or (5-propyl-2-oxo-1,3-dioxolen-4-yl)methyl.

The term "a 2-oxo-1,3-dioxolenemethylamino which may be substituted by phenyl or a (lower) alkyl" includes 2-oxo-1,3-dioxolenemethylamino which may be substituted by phenyl or a straight chain or branched chain $C_1$–$C_6$ alkyl, such as (5-methyl-2-oxo-1,3-dioxolen-4-yl)methylamino, (5-tert-butyl-2-oxo-1,3-dioxolen-4-yl)methylamino, (5-phenyl-2-oxo-1,3-dioxolen-4-yl)methylamino, (2-oxo-1,3-dioxolen-4-yl)methylamino, (5-pentyl-2-oxo-1,3-dioxolen-4-yl)methylamino, (5-hexyl-2-oxo-1,3-dioxolen-4-yl)methylamino, (5-ethyl-2-oxo-1,3-dioxolen-4-yl)methylamino, or (5-propyl-2-oxo-1,3-dioxolen-4-yl)methylamino.

The term "a cycloalkylamino" includes $C_3$–$C_8$ cycloalkylamino, such as cyclopropylamino, cyclobutylamino, cyclopentylamino, cyclohexylamino, cycloheptylamino or cyclooctylamino.

The term "a (lower) alkylthio" includes a straight chain or branched chain $C_1$–$C_6$alkylthio, such as methylthio, ethylthio, propylthio, isopropylthio, butylthio, tertbutylthio, penthylthio or hexylthio.

The term "a phenyl which may be substituted by 1 to 3 of substituents selected from the group consisting of a (lower) alkoxy, a halogen atom and hydroxy on phenyl ring" includes phenyl which may be substituted by 1 to 3 of substituents selected from the group consisting of a straight chain or branched chain $C_1$–$C_6$ alkoxy, a halogen atom and hydroxy on phenyl ring, such as phenyl, 4-methoxyphenyl, 3-ethoxyphenyl, 2-propoxyphenyl, 4-n-butoxyphenyl, 3-pentyloxyphenyl, 2-hexyloxyphenyl, 3,4-dimethoxyphenyl, 2,4,6-trimethoxyphenyl, 2-fluorophenyl, 4-fluorophenyl, 3-chlorophenyl, 4-chlorophenyl, 4-bromophenyl, 2-iodophenyl, 2,4-difluorophenyl, 2,6-difluorophenyl, 3,4-difluorophenyl, 2,5-difluorophenyl, 2,4-dichlorophenyl, 2,6-dibromophenyl, 2,4,6-trifluorophenyl, 3,4,6-trichlorophenyl, 4-fluoro-2-methoxyphenyl, 2-fluoro-4-hydroxyphenyl, 2-hydroxyphenyl, 3-hydroxyphenyl, 4-hydroxyphenyl, 2,3-dihydroxyphenyl, 2,4-dihydroxyphenyl or 2,4,6-trihydroxyphenyl.

The term "a (lower) alkyl which may be substituted by a halogen atom, a (lower) alkanoyloxy or hydroxy" includes, in addition to the above-mentioned (lower) alkyl, a straight chain or branched chain $C_1$–$C_6$ alkyl which is substituted by 1 to 3 of substituents selected from the group consisting of a halogen atom, a straight chain or branched chain $C_2$–$C_6$ alkanoyloxy or hydroxy, such as hydroxymethyl, 2-hydroxyethyl, 1-hydroxyethyl, 3-hydroxypropyl, 4-hydroxybutyl, 5-hydroxypentyl, 6-hydroxyhexyl, 3-chloropropyl, bromomethyl, 2-fluoroethyl, 4-chlorobutyl, 3-fluoropentyl, difluoromethyl, 2,3-dichlorohexyl, 2,2,2-trifluoroethyl, trifluoromethyl, acetyloxymethyl, 2-propionyloxyethyl, 3-butyryloxypropyl, 4-pentanoyloxybutyl, 5-hexanoyloxypentyl, 6-acetyloxyhexyl, propanoyloxymethyl, 1-acetyloxyethyl, 2-acetyloxyethyl or 2-hexanoyloxyethyl.

The compounds of the present invention of the above general formula [1] can be prepared by various processes and preferably prepared, for example, by the processes as shown in the following reaction schemes.

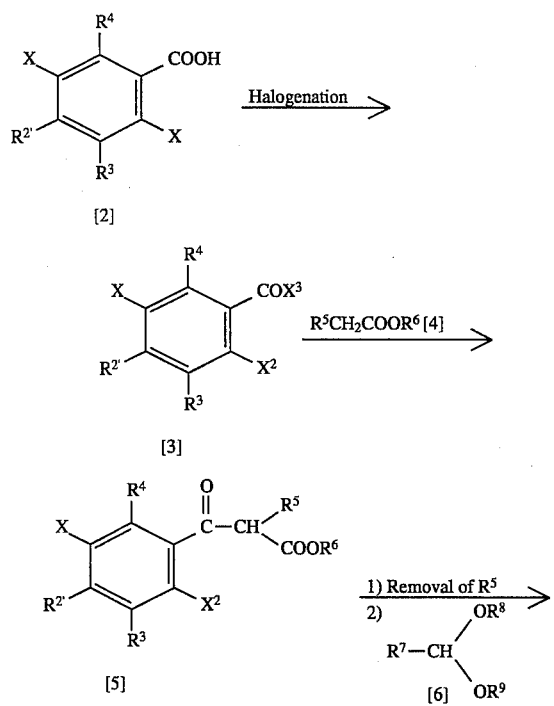

-continued
[Reaction scheme-I]

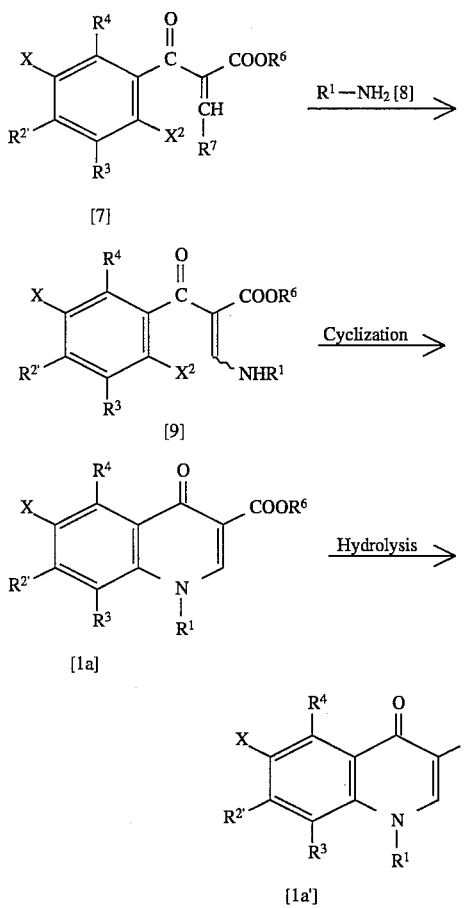

wherein $R^1$, $R^2$, $R^3$, $R^4$ and X are as defined above, $R^{2'}$ is a halogen atom or the $R^2$ group ($R^2$ is as defined above), $R^5$ is a group of the formula: $—COR^{10}$ (wherein $R^{10}$ is a (lower) alkyl) or a group of the formula: $—COOR^{11}$ (wherein $R^{11}$ is a (lower) alkyl), $R^6$ is a (lower) alkyl, $R^7$ is a group of the formula:

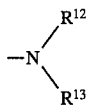

(wherein $R^{12}$ and $R^{13}$ are each a (lower) alkyl) or a (lower) alkoxy, $X^2$ and $X^3$ are each a halogen atom, $R^8$ and $R^9$ are each a (lower) alkyl.

The halogenation of the compound [2] is carried out by reacting with a halogenating agent in the presence or absence of a solvent. The solvent includes aromatic hydrocarbons such as benzene, toluene and xylene, halogenated hydrocarbons such as dichloromethane, chloroform and carbon tetrachloride, ethers such as dioxane, tetrahydrofuran and diethyl ether, dimethylformamide (DMF), dimethyl sulfoxide (DMSO), and the like. The halogenating agent may be any conventional halogenating agents which can convert hydroxy in a carboxy group into a halogen atom, and includes, for example, thionyl chloride, phosphorus oxychloride, phosphorus oxybromide, phosphorus pentachloride, phosphorus pentabromide, and the like. The amounts of the compound [2] and the halogenating agent are not particularly limited, but, in case of using no solvent, the halogenating agent is usually used in a large excess amount, and in case of using a solvent, the halogenating agent is usually used in an amount of at least 1 mole, preferably 2 to 4 moles, per 1 mole of the compound [2]. The reaction temperature and the reaction period of time are not particularly limited either, but the reaction is usually carried out at a temperature of from room temperature to around 100° C. for about 30 minutes to about 6 hours.

The reaction between the compound [3] and the compound [4] is carried out in a suitable solvent in the presence of a basic compound. The solvent used in the reaction may be any conventional solvents unless they give any undesirable effect on the reaction, and includes, for example, water, ethers such as diethyl ether, dioxane, tetrahydrofuran, monoglyme and diglyme, alcohols such as methanol, ethanol and isopropanol, aromatic hydrocarbons such as benzene, toluene and xylene, aliphatic hydrocarbons such as n-hexane, heptane, cyclohexane and ligroin, amines such as pyridine and N,N-dimethylaniline, halogenated hydrocarbons such as chloroform, dichloromethane and carbon tetrachloride, aprotic polar solvents such as DMF, DMSO and hexamethylphosphoramide (HMPA), and a mixture of these solvents. The basic compound employed in the reaction includes inorganic bases such as metallic sodium, metallic potassium, metallic magnesium, sodium hydride, sodium amide, sodium hydroxide, potassium hydroxide, sodium carbonate, potassium carbonate and sodium hydrogen carbonate, metal alcoholates such as sodium methylate and sodium ethylate, and organic bases such as pyridine, piperidine, quinoline, triethylamine and N,N-dimethylaniline. The reaction is usually carried out at a temperature of from around 0° C. to around 150° C., preferably from around 0° C. to around 120° C., for about 0.5 to about 20 hours. The compound [4] is usually used in an amount of at least 1 mole, preferably 1 to 2 moles, per 1 mole of the compound [3]. The basic compound is usually used in an amount of at least 1 mole, preferably 1 to 2 moles, per 1 mole of the compound [3].

The compound [5] wherein $R^5$ is the group of the formula: $—COR^{10}$ is subjected to the reaction for removal of the group: $—COR^{10}$ in a suitable solvent in the presence of a basic compound. The solvent used in the reaction includes, for example, ethers such as diethyl ether, dioxane, tetrahydrofuran, monoglyme and diglyme, aromatic hydrocarbons such as benzene, toluene and xylene, aliphatic hydrocarbons such as n-hexane, heptane and cyclohexane, aprotic polar solvents such as DMF, DMSO and HMPA, and the like. The basic compound includes ammonia gas, aqueous ammonia, ammonium salts such as ammonium chloride, primary or secondary amines such as ethylamine, diethylamine and piperidine, and the like. The reaction is usually carried out at a temperature of from around 0° C. to around 150° C., preferably from room temperature to around 100° C., for about 1 to about 20 hours.

The compound [5] wherein $R^5$ is a group of the formula: $—COOR^{11}$ is subjected to the reaction for removal of the group: $—COOR^{11}$ in an aqueous solution in the presence of an acid catalyst. The acid catalyst used in the reaction includes mineral acids such as hydrochloric acid and sulfuric acid, and organic acids such as p-toluenesulfonic acid. The reaction is usually carried out at a temperature of from around 0° C. to around 150° C., preferably from room temperature to around 100° C., for about 1 to about 20 hours.

The reaction between the obtained $R^5$ group-removed compound and the compound [6] is carried out in a suitable solvent. The solvent employed in the reaction may be any solvents which are used in the above reaction for the removal of the $R^4$ group in addition to anhydrous (lower) alkanoic acid such as acetic anhydride. The reaction is usually carried out at a temperature of from around 0° C. to around 200° C., preferably from around 0° C. to around 150° C., for about 0.5 to about 10 hours. The compound [6] is usually used in an equimolar to large excess amount, preferably in an equimolar to 2 times molar amount based on the compound [5]. In case of using a compound [6] wherein $R^7$ is a (lower) alkoxy group, the reaction may also be carried out by using acid anhydrides such as acetic anhydride as a solvent as well as the above-mentioned solvents at a temperature of from around 0° C. to around 200° C., preferably from around 0° C. to around 170° C.

The reaction between the compound [7] and the compound [8] is carried out in a suitable solvent. The solvent employed in the reaction may be any conventional solvents unless they give any undesirable effect on the reaction, and includes, for example, alcohols such as methanol, ethanol and propanol, ethers such as diethyl ether, dioxane, tetrahydrofuran, monoglyme and diglyme, aromatic hydrocarbons such as benzene, toluene and xylene, aliphatic hydrocarbons such as n-hexane, heptane, cyclohexane and ligroin, halogenated hydrocarbons such as chloroform, methylene chloride and carbon tetrachloride, aprotic polar solvents such as DMF, DMSO and HMPA, and the like. The reaction is usually carried out at a temperature of from around 0° C. to around 150° C., preferably from room temperature to around 100° C., for about 0.1 to about 15 hours. The compound [8] is usually used in an amount of at least 1 mole, preferably 1 to 2 moles, per 1 mole of the compound [7]. In the reaction, a basic compound may optionally be added. Such basic compound may be any basic compounds which are used in the above reaction between the compound [3] and the compound [4].

The cyclization of the compound [9] is carried out in a suitable solvent in the presence of a basic compound. The solvent employed in the reaction may be any conventional solvents unless they give any undesirable effect on the reaction, and includes, for example, ethers such as diethyl ether, dioxane, tetrahydrofuran, monoglyme and diglyme, aliphatic hydrocarbons such as n-hexane, heptane and ligroin, halogenated hydrocarbons such as chloroform, methylene chloride and carbon tetrachloride, aprotic polar solvents such as DMF, DMSO and HMPA, and the like. The basic compound employed in the reaction includes inorganic bases such as metallic sodium, metallic potassium, sodium hydride, sodium amide, sodium hydroxide, potassium hydroxide, sodium carbonate and potassium carbonate, metal alcoholates such as sodium methylate and sodium ethylate, organic bases such as 1,8-diazabicyclo[5.4.0]-undecene-7 (DBU), N-benzyltrimethylammonium hydroxide and tetrabutylammonium hydroxide, and the like. The reaction is usually carried out at a temperature of from around 0° C. to around 200° C., preferably from room temperature to around 150° C., for about 0.5 to about 15 hours. The basic compound is usually used in an amount of at least 1 mole, preferably 1 to 2 moles, per 1 mole of the compound [9].

The hydrolysis of the compound [1a] can be carried out under the conditions of conventional hydrolysis, for instance, in the presence of a basic compound such as sodium hydroxide, potassium hydroxide, barium hydroxide or potassium carbonate, a mineral acid such as sulfuric acid, hydrochloric acid or nitric acid, or an organic acid such as acetic acid or aromatic sulfonic acids, in a solvent including water, alcohols such as methanol, ethanol and isopropanol, ketones such as acetone and methyl ethyl ketone, ethers such as dioxane and ethylene glycol diethyl ether, acetic acid, or a mixture thereof. The reaction is usually carried out at a temperature of from room temperature to around 200° C., preferably from room temperature to around 150° C., for about 0.1 to about 30 hours. By the reaction, there is produced the compound [1a'].

[Reaction Scheme-II]

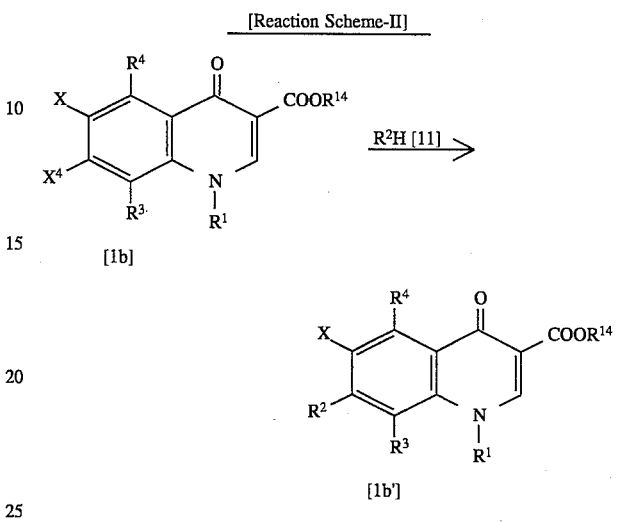

wherein $R^1$ $R^2$ $R^3$ $R^4$ and X are as defined above, $X^4$ is a halogen atom, and $R^{14}$ is hydrogen atom or a group of the formula:

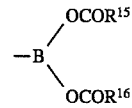

(wherein $R^{15}$ and $R^{16}$ are each an alkyl).

For conducting the reaction between the compound [1b] and the compound [11], both compounds are used in a wide range of ratio, and the compound [11] is usually used in an amount of at least 1 mole, preferably about 1 to about 5 moles, per 1 mole of the compound [1b]. The reaction is carried out in an inert solvent, which includes, for example, water, alcohols such as methanol, ethanol, isopropanol, butanol, amyl alcohol and isoamyl alcohol, aromatic hydrocarbons such as benzene, toluene and xylene, ethers such as tetrahydrofuran, dioxane and diglyme, dimethylacetamide, DMF, DMSO, HMPA, N-methylpyrrolidone, and the like and a mixture thereof. Among these solvents, the preferred one is DMF, DMSO, HMPA, and N-methylpyrrolidone. The reaction may also be carried out in the presence of an acid-removing agent, including inorganic carbonates such as sodium carbonate, potassium carbonate, sodium hydrogen carbonate and potassium hydrogen carbonate and organic bases such as pyridine, quinoline and triethylamine. An alkaline methal halide such as potassium fluoride may also be added to the reaction mixture. The reaction is usually carried out under a pressure of from 1 to 20 atm., preferably from 1 to 10 atm., at a temperature of from room temperature to around 250° C., preferably from room temperature to around 200° C., for about 10 minutes to about 30 hours.

The compound [1b'] wherein $R^{14}$ is a group of the formula:

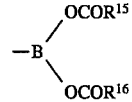

can be converted into the corresponding compound [Ib'] wherein $R^{14}$ is hydrogen atom by treating the former compound with an acid or a base to decompose the chelate compound. The acid employed in the reaction includes mineral acids such as hydrochloric acid and sulfuric acid, and organic acids such as acetic acid and p-toluenesulfonic acid. The base employed in the reaction includes mineral bases such as sodium hydroxide, potassium hydroxide, sodium hydrogen carbonate, potassium hydrogen carbonate and potassium carbonate, and organic bases such as triethylamine. The reaction favorably proceeds at a temperature of from around 0° C. to around 150° C., preferably from around 0° C. to around 100° C. The acid or the base may be used in an amount of at least 1 mole, preferably 1 to 10 moles, per 1 mole of the starting compound.

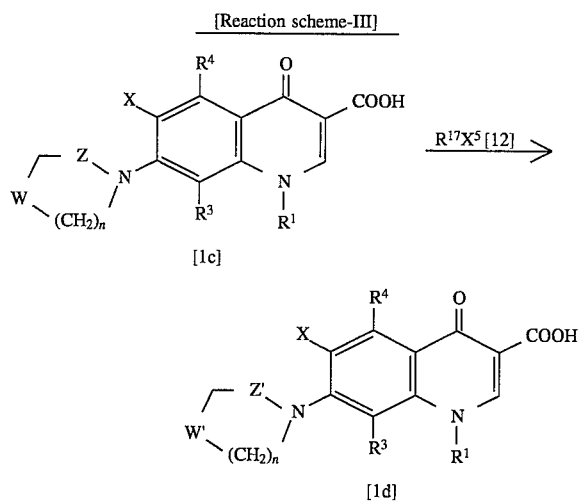

wherein X, $R^1$, $R^3$ and $R^4$ are as defined above, either Z or W is —CH$_2$— and the other is —NH, n is an integer of 1 to 3, $R^{17}$ is a (lower) alkyl; a cycloalkyl; a phenyl(lower)alkyl in which phenyl ring may be substituted by a (lower) alkoxy, nitro or amino; a phenyl which may be substituted by a halogen atom or a (lower) alkyl which may be substituted by 1 to 3 of halogen atoms; a pyridyl; a (lower) alkyl having 1 to 3 of substituents selected from the group consisting of hydroxy, an amino which may be substituted by 1 or 2 substituents of a (lower) alkyl, a (lower) alkanoyl, a cycloalkyl or a (lower) alkoxycarbonyl, a (lower) alkoxy and a halogen atom; a (lower) alkanoyl which may be substituted by 1 to 7 of halogen atoms; a (lower) alkenylcarbonyl having 1 to 3 of substituents selected from the group consisting of a halogen atom and a carboxy; a (lower) alkoxycarbonyl; an aminocarbonyl which may be substituted by a (lower) alkyl; a phenyl(lower)alkoxycarbonyl; an amino(lower)alkanoyl which may be substituted by a phenyl(lower)alkoxycarbonyl; a (lower) alkoxycarbonyl-(lower)alkyl; a carboxy(lower)alkyl; an anilinocarbonyl-(lower)alkyl; a (lower) alkylsulfonyl which may be substituted by 1 to 3 of halogen atoms; a sulfo(lower)alkyl; a (lower) alkenyl or a (lower) alkynyl, $X^5$ is a halogen atom, and either Z' or W' is —CH$_2$— and the other is —NR$^{17}$.

The reaction between the compound [Ic] and the compound [12] is carried out in a suitable solvent in the presence of a hydrogen halide-removing agent. The solvent includes water, alcohols such as methanol, ethanol and isopropanol, ketones such as acetone and methyl ethyl ketone, ethers such as diethyl ether and dioxane, aromatic hydrocarbons such as benzene, toluene and xylene, and the like. The hydrogen halide-removing agent includes inorganic bases such as sodium hydroxide, potassium hydroxide, sodium carbonate and potassium carbonate, alkaline metals such as sodium and potassium, and organic bases such as pyridine and piperidine. If necessary, copper powders, copper halides such as copper iodide or alkaline metal halides such as sodium iodide and potassium iodide may also be employed. The compound [12] is usually used in an equimolar to large excess amount, preferably 1 to 3 moles, per 1 mole of the compound [Ic]. The reaction is usually carried out at a temperature of from room temperature to around 150° C., preferably from around 50° C. to around 120° C., for about 1 to about 12 hours.

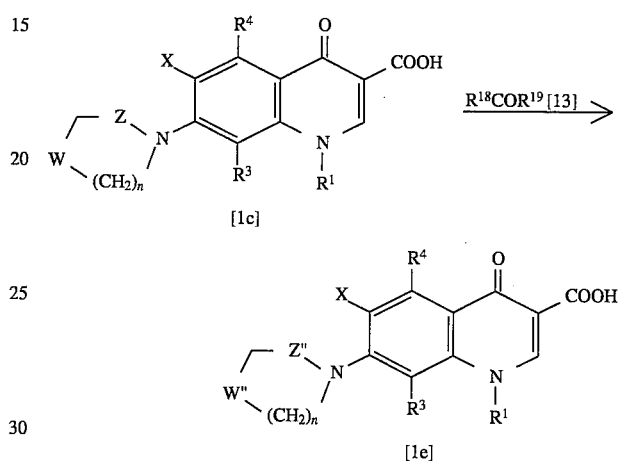

wherein $R^1$, $R^3$, $R^4$, Z, W, n and X are as defined above, $R^{18}$ and $R^{19}$ are each hydrogen atom or a lower alkyl, and either Z" or W" is —CH$_2$—and the other is

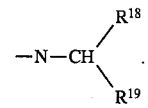

The reaction between the compound [Ic] and the compound [13] is carried out in the presence or absence of a solvent in the presence of a reducing agent. The solvent employed in the reaction includes, for example, water, alcohols such as methanol, ethanol and isopropanol, lower alkanoic acids such as formic acid and acetic acid, ethers such as dioxane, diethyl ether, diglyme and tetrahydrofuran, aromatic hydrocarbons such as benzen, xylene and toluene, and the like. The reducing agent includes formic acid, alkaline metal or alkaline earth metal salts of formic acid such as sodium formate, reducing agents for hydrogenation such as sodium borohydride, sodium cyanoborohydride and lithium aluminum hydride, catalysts for catalytic reduction such as palladium black, palladium carbon, platinum oxide, platinum black and Raney nickel, and the like. In case of using formic acid as the reducing agent, the reaction is usually carried out at a temperature of from room temperature to around 200° C., preferably from around 50° C. to around 150° C., for about 1 to about 10 hours. Formic acid is preferably used in a large excess amount to the compound [Ic]. Besides, in case of using a reducing agent for hydrogenation, the reaction is usually carried out at a temperature of from around −30° C. to around 100° C., preferably from around 0° C. to around 70° C., for about 30 minutes to about 12 hours. The reducing agent is usually used in an amount of from 1 to 20 moles, preferably from 1 to 6 moles, per 1 mole of the compound [lc]. In case of using lithium aluminum hydride as the reducing agent, a preferable solvent includes ethers such as diethyl ether, dioxane, tetrahydrofuran and diglyme, aromatic hydrocarbons such as benzene, toluene and xylene, and the like. In case of using a catalyst for catalytic reduction, the reaction is usually carried out under a hydrogen pressure of from ordinary pressure to 20 atm., preferably from ordinary pressure to 10 atm., at a temperature of from −30° C. to 100° C., preferably from 0° C. to 60° C., for 1 to 12 hours. The catalyst is usually used in an amount of from 0.1 to 40% by weight, preferably from 0.1 to 20% by weight, of the compound [lc]. The compound [13] is usually used in an amount of at least 1 mole, preferably 1 mole to a large excess amount, per 1 mole of the compound [lc].

In the reaction scheme-I, the starting compounds of the formula [2] are novel or known compounds, which can be prepared, for example, by the process as shown in the following reaction scheme-V.

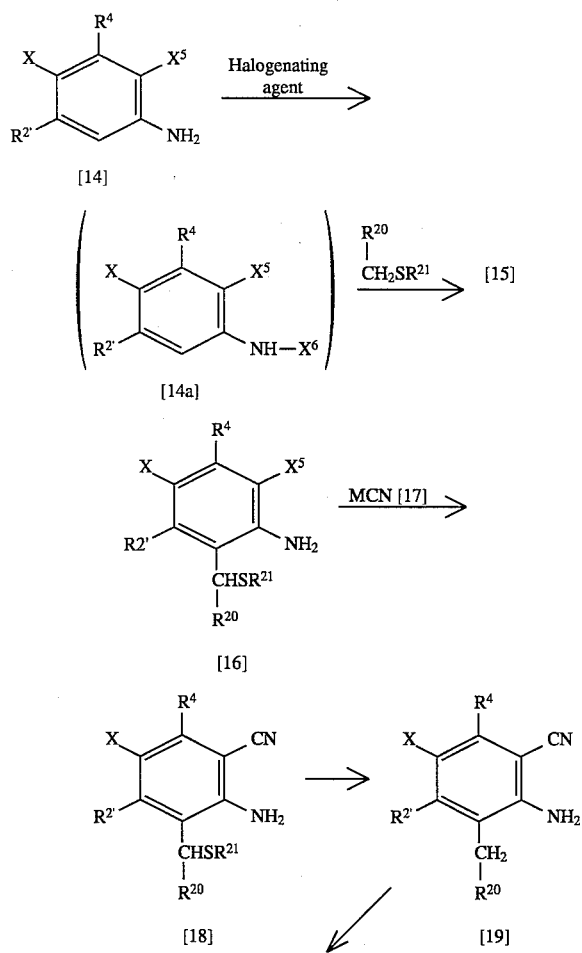

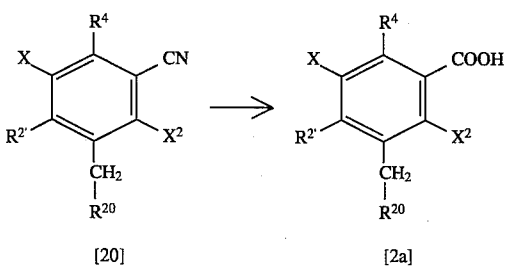

wherein X, $R^{2'}$, $R^4$ and $X^2$ are as defined above, $X^5$ and $X^6$ are each a halogen atom, $R^{20}$ is hydrogen atom or a (lower) alkyl and $R^{21}$ is a (lower) alkyl, in which $R^{20}$ and $R^{21}$ may be taken together to form a 5- to 7-membered ring, and M is an alkaline metal such as sodium or potassium, or a metal such as silver, calcium or copper.

In case that $R^{20}$ and $R^{21}$ of the compound [16] are taken together to form a 5- to 7-membered ring, $R^{20}$ of the compound [20] is —$R^{20}$—$R^{21}$—H.

The compound [16] can be prepared by reacting the starting aniline derivative of the formula [14] with a halogenating agent and then reacting the resultant compound of the formula [14a] with the thio compound of the formula [15].

The reaction between the aniline derivative [14] and the halogenating agent is usually carried out in a suitable solvent. The solvent may be any conventional solvents unless they give any undesirable effect on the reaction. Such solvent includes, for example, halogenated hydrocarbons such as chloroform and dichloromethane, ethers such as dioxane, diethyl ether and tetrahydrofuran, aromatic hydrocarbons such as benzene, toluene and xylene, lower alcohols such as methanol, ethanol and isopropanol, polar solvents such as DMSO, HMPA and acetonitrile, and the like. The halogenating agent employed in the above reaction may be any conventional halogenating agents and includes, for example, N-bromosuccinimide, N-chlorosuccinimide, sodium hypobromite, sodium hypochlorite, bleaching powder, thionyl chloride, tert-butyl hypochloride, and the like. The halogenating agent is usually used in an amount of at least 1 mole, preferably 1 to 6 moles, per 1 mole of the starting compound. The reaction is usually carried out at a temperature of from around −78° C. to room temperature, preferably from around −60° C. to around 15° C., and usually completes in a moment or within a few minutes.

By the reaction, there is produced the intermediate of the formula [14a]. While the resultant compound [14a] may be separated from the reaction mixture to provide it for a subsequent reaction, the reaction mixture is usually subjected to the reaction with the thio compound of the formula [15] without separating it from the reaction mixture.

The reaction between the intermediate compound [14a] and the compound [15] is carried out in the same solvent and at the same temperature as mentioned above in the presence of a suitable basic compound. The preferable basic compound which can be employed in the reaction includes inorganic bases such as potassium carbonate, sodium carbonate, sodium hydroxide, sodium hydrogen carbonate, sodium amide and sodium hydride, and organic bases including tertiary amines such as triethylamine, tripropylamine, pyridine and quinoline. The compound [15] is usually used in an amount of at least 1 mole, preferably 1 to 1.5 moles, per 1 mole of the intermediate compound [14a]. The reaction is usually carried out at a temperature of from room temperature to around 150° C., preferably from room temperature to around 100° C., for about 1 to about 50 hours.

The reaction between the compound [16] and the compound [17] is carried out in a suitable solvent in the presence or absence of a basic compound. The solvent employed in the reaction includes water, alcohols such as methanol, ethanol and isopropanol, aromatic hydrocarbons such as benzene, toluene and xylene, ethers such as dioxane, tetrahydrofuran and diglyme, polar solvents such as DMF, DMSO, HMPA and N-methylpyrrolidone, or a mixture thereof. The basic compound includes, for example, inorganic carbonates such as sodium carbonate, potassium carbonate, sodium hydrogen carbonate and potassium hydrogen carbonate, organic bases such as pyridine, quinoline and triethylamine, phase transfer catalysts such as phenyltriethylammonium chloride and tetramethylammonium chloride, and the like. The compound [17] is usually used in an amount of at least 1 mole, preferably 1 to 2 moles, per 1 mole of the compound [16]. The reaction is usually carried out at a temperature of from room temperature to around 200° C., preferably from room temperature to around 180° C., for about 0.5 to about 10 hours.

The desulfurization of the compound [18] for preparing the compound [19] is usually carried out in a solvent in the presence of a suitable catalyst. The catalyst includes, for example, aluminum-amalgam, lithium-(lower) alkylamine, Raney nickel, Raney cobalt, triethyl phosphite, triphenyl phosphine, and the like, and preferably Raney nickel. The solvent includes alcohols such as methanol, ethanol and isopropanol, ethers such as diethyl ether, dioxane and tetrahydrofuran, and the like. The reaction is usually carried out at a temperature of from around 0° C. to around 200° C., preferably from room temperature to around 100° C., for about 10 minutes to about 5 hours. The catalyst is usually used in an amount of from 1 to 10-fold by weight of the compound [18].

The reaction of converting the compound [19] into the compound [20] is carried out by reacting the compound [19] with a metallic salt of nitrous acid such as sodium nitrite or potassium nitrite in a suitable solvent in the presence of an acid, and then reacting the resultant product, without separation from the reaction mixture, with a metal halide such as potassium iodide, copper (I) chloride or copper (I) bromide. The acid employed in the reaction includes mineral acids such as hydrochloric acid, sulfuric acid and hydrobromic acid. The solvent includes water, alkanoic acids such as acetic acid, aromatic hydrocarbons such as benzen, toluene and xylene, alcohols such as methanol, ethanol and isopropanol, halogenated hydrocarbons such as chloroform, dichloromethane and dichloroethane, ethers such as dioxane and tetrahydrofuran, aprotic polar solvents such as DMF, DMSO and HMPA, and a mixture thereof. The metallic salt of nitrous acid and the metal halide each is usually used in an amount of at least 1 mole, preferably 1 to 1.5 moles, per 1 mole of the compound [19]. The reaction is usually carried out at a temperature of from around 0° C. to around 150° C., preferably from around 0° C. to around 100° C., for about 10 minutes to about 5 hours.

The hydrolysis of the compound [20] can be carried out in the presence of a suitable hydrolysis catalyst, including a mineral alkaline compound, e.g., a hydrohalogenic acid such as hydrochloric acid or hydrobromic acid, a mineral acid such as sulfuric acid or phosphoric acid, an alkaline metal hydroxide such as sodium hydroxide, potassium hydroxide, an alkaline metal carbonate or hydrogencarbonate such as sodium carbonate, potassium carbonate or sodium hydrogen carbonate, in the presence or absence of a suitable solvent, such as, for example, water or a mixture of-water and a lower alcohol such as methanol or ethanol. The reaction is usually carried out at a temperature of from 50° C. to 200° C., preferably from 70° C. to 180° C., for about 1 to about 10 hours.

In the reaction scheme-II, the compounds of the formula [Ib] wherein $R^{14}$ is a group:

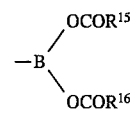

be prepared, for example, by the process as shown in the following reaction scheme-VI.

[Reaction scheme-VI]

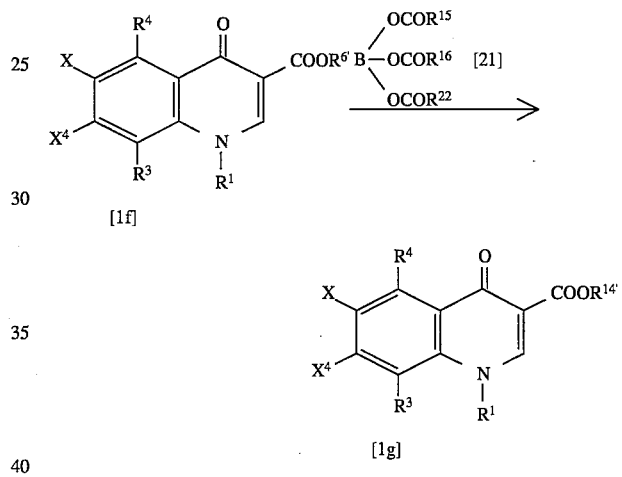

wherein $R^1$, $R^3$, $R^4$, $X$, $X^4$, $R^{15}$ and $R^{16}$ are as defined above, $R^{6'}$. $R^{14'}$ is a (lower) alkyl or hydrogen atom, is a group:

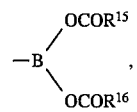

and $R^{22}$ is a (lower) alkyl.

The reaction between the compound [1f] and the compound [21] is carried out in a suitable solvent. The solvent employed in the reaction includes, for example, the solvents employed in the reaction between the $R^5$ group-removed compound and the compound [6] in the above reaction scheme-I. The reaction is usually carried out at a temperature of from room temperature to around 200° C., preferably from room temperature to around 150° C., for about minutes to about 5 hours. The compound [21] is usually used in an amount of at least 1 mole, preferably 1 to 10 moles, per 1 mole of the compound [1f].

The compounds [8] employed in the reaction scheme-I are novel or known compounds, which can be prepared, for example, by the process as shown in the following reaction scheme-VII.

[Reaction scheme-VII]

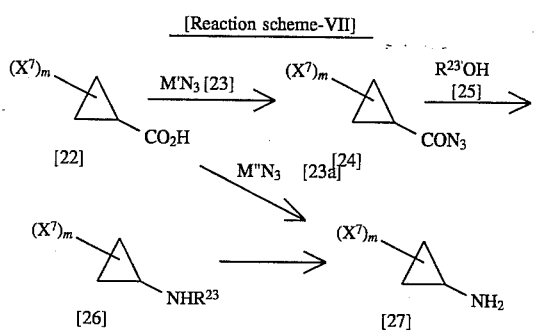

wherein $X^7$ is a halogen atom, $R^{23}$ is a phenyl(lower) alkoxycarbonyl, $R^{23'}$ is a phenyl(lower)alkyl, m is an integer of 1 to 3, M' is an alkaline metal such as sodium or potassium, and M" is hydrogen atom or M'.

The reaction between the compound [22] and the compound [23] can be carried out under reaction conditions usually employed in a reaction for forming an amide bond. For forming an amide bond, known reaction conditions for the amide bond formation can be employed, for example, (a) a mixed acid anhydride process: a process which comprises reacting the carboxylic acid [22] with an alkyl halocarboxylate to give a mixed acid anhydride, which is then reacted with the azide [23]; (b) an active ester process: a process which comprises converting the carboxylic acid [22] into an active ester such as p-nitrophenyl ester, N-hydroxysuccinimide ester or 1-hydroxybenzotriazole ester, and then reacting the resultant ester with the azide [23]; (c) a carbodiimide process: a process which comprises condensing the carboxylic acid [22] with the azide [23] in the presence of an activating agent such as dicyclohexylcarbodiimide or carbonyldiimidazole; and (d) other processes: a process which comprises converting the carboxylic acid [22] into the carboxylic anhydride using a dehydration agent such as acetic anhydride, and then reacting the resultant anhydride with the azide [23], a process which comprises reacting an ester from the carboxylic acid [22] and a lower alcohol with the azide [23] under a high pressure at a high temperature, or a process which comprises reacting an acid halide of the carboxylic acid [22], i.e. acyl halide with the azide [23].

The mixed acid anhydride used in the above mixed acid anhydride process can be obtained by a conventional Schotten-Baumann reaction, and the resultant anhydride is reacted with the azide [23], usually without separating it from the reaction mixture, to prepare the compound [24]. The Schotten-Baumann reaction is carried out in the presence of a basic compound. The basic compound which can be employed in the reaction includes those usually employed in the Schotten-Baumann reaction, for example, organic bases such as triethylamine, trimethylamine, pyridine, dimethylaniline, N-methylmorpholine, 1,5-diazabicyclo [4,3,0] nonene-5 (DBN), 1,8-diazabicyclo [5,4,0] undecene-7 (DBU) and 1,4-diazabicyclo[2,2,2] octane (DABCO), and inorganic bases such as potassium carbonate, sodium carbonate, potassium hydrogen carbonate and sodium hydrogen carbonate. The reaction is usually carried out at a temperature of from around −20° C. to around 100° C., preferably from around 0° C. to around 50° C., for 5 minutes to 10 hours, preferably 5 minutes to 2 hours. The reaction between the obtained mixed acid anhydride and the azide [23] is usually carried out at a temperature of from around −20° C. to around 150°C., preferably from around 0° C. to around 50° C., for 5 minutes to 10 hours, preferably for 5 minutes to 5 hours. The mixed acid anhydride process is usually carried out in a solvent. The solvent may be any which is usually employed in the mixed acid anhydride process, including water, halogenated hydrocarbons such as methylene chloride, chloroform and dichloroethane, aromatic hydrocarbons such as benzene, toluene and xylene, ethers such as diethyl ether, tetrahydrofuran and dimethoxyethane, esters such as methyl acetate and ethyl acetate, ketones such as acetone, aprotic polar solvents such as DMF, DMSO and HMPA, and a mixture thereof. The alkyl halocarboxylate used in the mixed acid anhydride process includes, for example, methyl chloroformate, methyl bromoformate, ethyl chloroformate, ethyl bromoformate, isobutyl chloroformate, and the like. The azide [23] is usually used in an amount of at least 1 mole, preferably 1 to 1.5 moles, per 1 mole of the carboxylic acid [22].

In case of using the process of reacting an acyl halide with the azide [23], the reaction is carried out in a suitable solvent in the presence of a basic compound. The basic compound used in the reaction may be any known basic compounds, including, for example, sodium hydroxide, potassium hydroxide, sodium hydride, potassium hydride, silver carbonate, and metal alcoholates such as sodium methylate and sodium ethylate, in addition to the basic compound employed in the above Schotten-Baumann reaction. The solvent used in the reaction includes, for example, alcohols such as methanol, ethanol, propanol, butanol, 3-methoxy-1-butanol, ethyl cellosolve and methyl cellosolve, pyridine, acetone, acetonitrile, the solvents employed in the above mixed acid anhydride process, and a mixture thereof. Although the ratio of the azide [23] and an acyl halide employed is not particularly limited, the acyl halide is usually used in an amount of at least 1 mole, preferably 1 to 5 moles, per 1 mole of the azide [23]. The reaction is usually carried out at a temperature of from around −30° to around 180° C., preferably from around 0° C. to around 150° C., for about 5 minutes to about 30 hours. The compound [24] thus prepared may be used in a subsequent reaction without separating it from the reaction mixture.

The reaction between the compound [24] and the compound [25] is usually carried out at a temperature of from around 0° C. to around 150° C., preferably from room temperature to around 100° C., for 1 to 15 hours, in a suitable solvent or in the absence of a solvent. The compound [25] is usually used in an amount of at least 1 mole, preferably 1 to 2 moles, per 1 mole of the compound [24].

The reaction of converting the compound [26] into the compound [27] can be carried out under the same reaction conditions as used in the reaction for removing a phenyl (lower) alkyl or a phenyl (lower) alkoxycarbonyl on the heterocyclic ring attached to the above compound [1].

The reaction of directly converting the compound [22] into the compound [27] is generally referred to as Schmidt reaction, and carried out in a suitable solvent in the presence of an acid. The acid employed in the reaction includes mineral acids such as sulfuric acid and hydrochloric acid, phosphorus compounds such as phosphorus oxychloride, phosphorus pentachloride, phosphorus trichloride and phosphorus pentoxide, thionyl chloride, iron [III] chloride, aluminum chloride, stannic chloride, sulfoacetic acid, phosphoric acid, and the like. The solvent includes aromatic hydrocarbons such as benzene, toluene and xylene, halogenated hydrocarbons such as chloroform, dichloromethane and carbon tetrachloride, and the like. The reaction is usually carried out at a temperature of from around 0° C. to around 150° C., preferably from around 0° C. to around 100° C., for about 0.5 to about 10 hours. The compound [23a] is usually used in an amount of at least 1 mole, preferably 1 to 2 moles, per 1 mole of the compound [22].

27

[Reaction scheme-VIII]

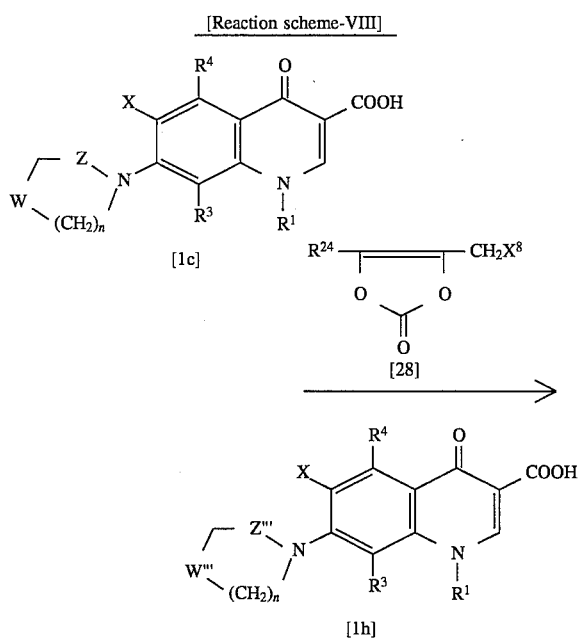

wherein $R^{24}$ is phenyl, a lower alkyl or hydrogen atom, $X^8$ is a halogen atom, either $Z'''$ or $W''''$ is —$CH_2$— and the other is a group:

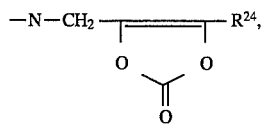

and $R^1$, $R^3$, $R^4$, W, X and n are as defined above.

The reaction between the compound [1c] and the compound [28] can be carried out under the same reaction conditions as employed in the reaction between the compound [1b] and the compound [11] in the above reaction scheme-II.

Among the compounds [1], the compound in which the heterocyclic ring is substituted by (a) a phenyl(lower)alkyl in which phenyl ring may be substituted by a (lower) alkoxy, nitro or amino; (b) a (lower) alkanoyl which may be substituted by 1 to 7 of halogen atoms, a (lower) alkenylcarbonyl having 1 to 3 of substituents selected from the group consisting of a halogen atom and a carboxy; (c) a (lower) alkoxycarbonyl; (d) an aminocarbonyl which may be substituted by a (lower) alkyl; (e) a phenyl(lower)alkoxycarbonyl; (f) an amino(lower)alkanoyl which may be substituted by a phenyl (lower)alkoxycarbonyl; (g) phthalide; (h) a

28

2(5H)-furanone which may be substituted by 1 or 2 of halogen atoms; or (i) a 2-oxo-1,3-dioxolenemethyl which may be substituted by phenyl or a (lower) alkyl can be converted into the compound [1] in which the heterocyclic ring is not substituted, for example, using the following methods.

The compound [1] in which the heterocyclic ring is substituted by (a) or (e) can be converted into the compound [1] in which the heterocyclic ring is not substituted, by treating the former compound in a suitable solvent such as, for example, water, a (lower) alcohol such as methanol, ethanol or isopropanol, an ether such as dioxane or tetrahydrofuran, acetic acid, or a mixture thereof, in the presence of a catalyst for catalytic reduction such as palladium carbon or palladium black, under a hydrogen pressure of from 1 to 10 atom., at a temperature of from around 0° C. to around 100° C., for about 0.5 to about 10 hours, wherein a mineral acid such as hydrochloric acid may be added to the reaction mixture, or by heating the former compound in an aqueous hydrobromic acid solution, to remove the phenyl(lower)alkyl such as benzyl or the phenyl(lower)-alkoxycarbonyl.

The compound [1] in which the heterocyclic ring is substituted by any of the substituents (b) to (i) can be converted into the compound [1] in which the heterocyclic ring is not substituted, by hydrolyzing the former compound under the same reaction conditions as employed in the hydrolysis of the above compound [1a].

The compound [1] in which the heterocyclic ring is substituted by amino can be converted into the compound [1] in which the heterocyclic ring is substituted by a group:

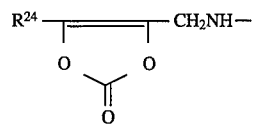

by using the same reaction conditions as employed in the reaction between the compound [1c] and the compound [28] in the above reaction scheme-VIII. The compound [1] in which the heterocyclic ring is substituted by group:

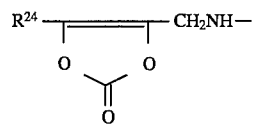

can also be converted into the compound [1] in which the heterocyclic ring is substituted by amino, by hydrolyzing the former compound under the same reaction conditions as employed in the hydrolysis of the above compound [1a].

[Reaction scheme-IX]

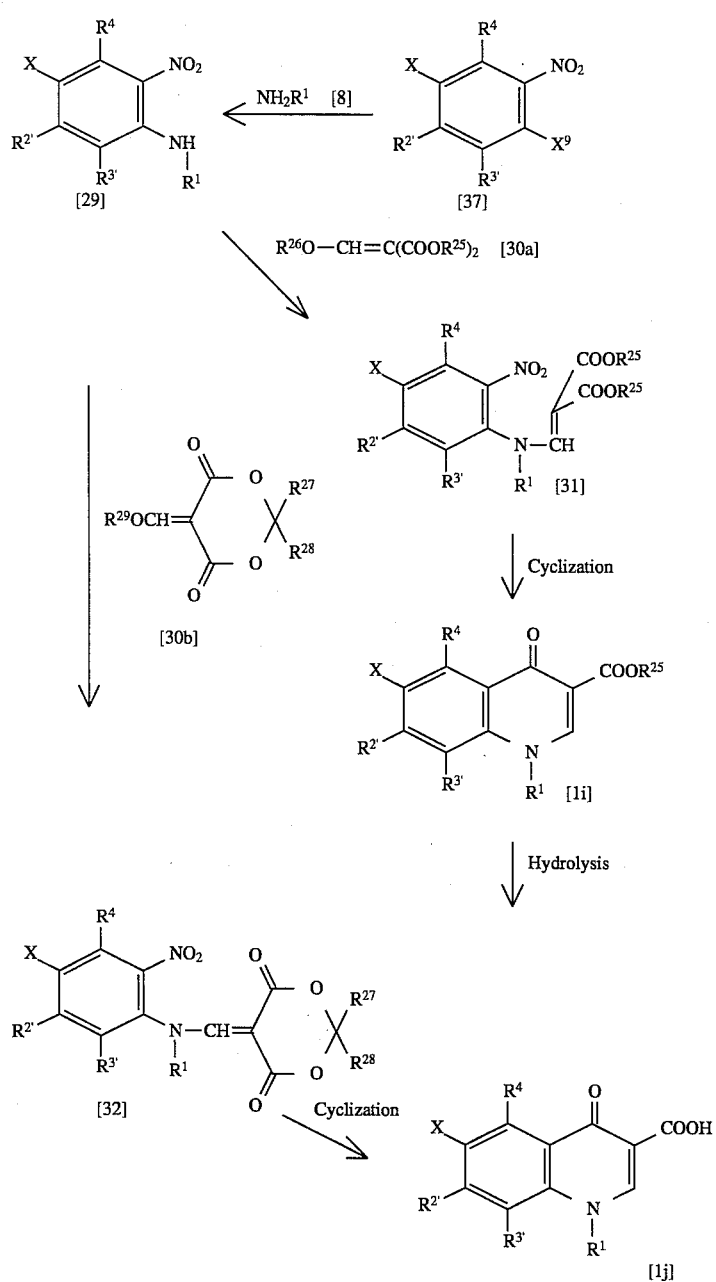

wherein $R^1$, $R^{2'}$, $R^3$, $R^4$, $X^9$ and X are as defined above, $R^{3'}$ is a group:

$$-CHSR^{21} \atop R^{20}$$

wherein $R^{20}$ and $R^{21}$ are as defined above or $R^3$, and $R^{25}$, $R^{26}$, $R^{27}$, $R^{28}$ and $R^{29}$ are each a (lower) alkyl.

The reaction between the compound [37] and the compound [8] can be carried out under the same reaction conditions as employed in the reaction between the compound [1b] and the compound [11] in the above reaction scheme-II.

The reaction between the compound [29] and the compound [30a] or [30b] is carried out in the presence or absence of a solvent, preferably in the absence of a solvent. The solvent used in the reaction includes, for example, alcohols such as methanol, ethanol and isopropanol, aromatic hydrocarbons such as benzene and toluene, polar solvents such as acetonitrile, DMF, DMSO and HMPA, and the like. The compound [30a] or [30b] is usually used in an amount of at least 1 mole, preferably 1 to 1.5 moles, per 1 mole of the compound [29]. The reaction is usually carried out at a temperature of from room temperature to around 200° C., preferably from around 60° C. to around 200° C., for about 0.5 to about 25 hours.

The cyclization of the compound [31] or [32] can be carried out according to various known methods for the cyclization, including a heating method, a method using an acidic compound such as phosphorus oxychloride, phosphorus pentachloride, phosphorus trichloride, thionyl chloride, conc. sulfuric acid or polyphosphoric acid, and the like. In case of using the heating method, the reaction is usually carried out in a high b.p. solvent such as a high b.p. hydrocarbon or a high b.p. ether such as tetralin, diphenyl ether or diethylene glycol dimethyl ether at a temperature of from 100° C. to 250° C., preferably from 150° C. to 200° C. In case of using the method with an acidic compound, the acidic compound is usually used in an equimolar to a large excess amount, preferably 10 to 20 moles, per 1 mole of the compound [31] or [32]. The reaction is usually carried out in the presence or absence of a suitable solvent at a temperature of from room temperature to 150° C. for about 0.1 to about 6 hours. The solvent includes acid anhydrides such as acetic anhydride in addition to the solvents employed in the cyclization-of the above compound [9].

The hydrolysis of the compound [1i] can be carried out under the same reaction conditions as employed in the hydrolysis of the compound [1a] in the above reaction scheme-I.

The compound [1j] in which $R^{3'}$ is a group:

can be coverted into the corresponding compound in which $R^{3'}$ is —$CH_2R^{20}$ by treating the former compound under the same reaction conditions as employed in the reaction wherein the compound [18] is converted into the compound [19] in the above reaction scheme-V.

The compound [1j] in which $R^{2'}$ is a 5- to 9-membered saturated or unsaturated heterocyclic ring having a (lower) alkoxycarbonyl on the secondary nitrogen atom can be converted into the corresponding compound in which $R^{2'}$ is a 5- to 9-membered saturated or unsaturated heterocyclic ring having no substituent on the secondary nitrogen atom by treating the former compound under the same reaction conditions as employed in the hydrolysis of the compound [1a] in the above reaction scheme-I.

The compound [29] employed as the starting material in the above reaction scheme-IX can be prepared, for example, by the processes as shown in the following reaction schemes-X to XIII.

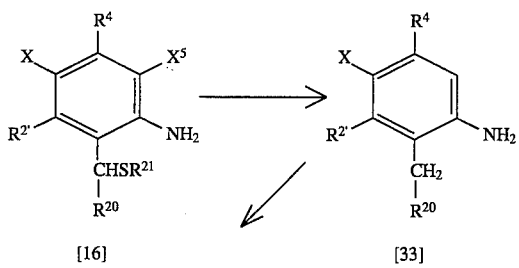

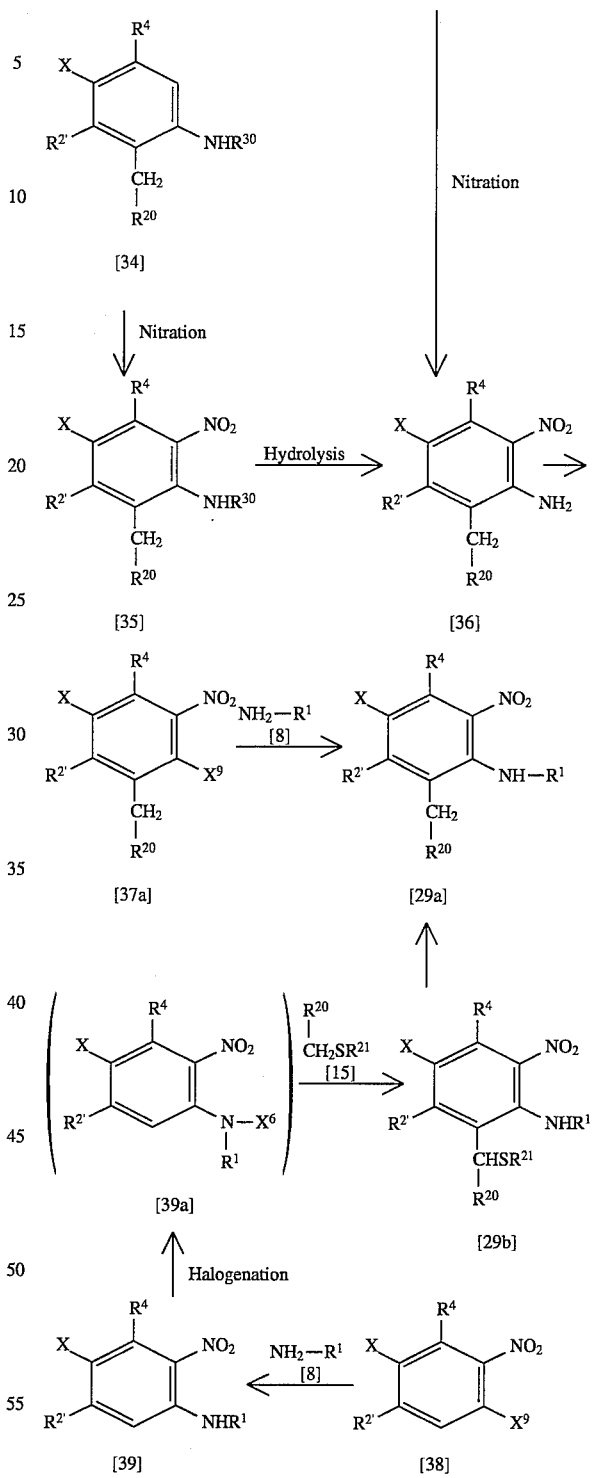

wherein $R^1$ $R^{2'}$, $R^{20}$, $R^{21}$, X $X^5$ and $X^6$ are as defined above, $R^{30}$ is a (lower) alkanoyl, and $X^9$ is a halogen atom.

The desulfurization of the compound [16] or [29b] can be carried out under the same reaction conditions as employed in the desulfurization of the above compound [18].

The reaction of converting the compound [33] into the compound [34] is carried out in the presence of a (lower) alkanoylating agent, which includes a (lower) alkanoic acid such as formic acid, acetic acid or propionic acid, a (lower) alkanoic acid anhydride such as acetic anhydride, a (lower) alkanoic acid halide such as acetyl chloride or propionyl bromide, or the like. In case of using an acid anhydride or an acid halide as the (lower) alkanoylating agent, a basic compound may also be employed. The basic compound includes, for example, alkali metals such as metallic sodium and metallic potassium; hydroxides, carbonates or hydrogen carbonates of these alkali metals; organic bases such as pyridine and piperidine, and the like. The reaction can be carried out in either the presence or the absence of a solvent, usually in the presence of a suitable solvent. The solvent includes, for example, ketones such as acetone and methyl ethyl ketone, ethers such as diethyl ether and dioxane, aromatic hydrocarbons such as benzene, toluene and xylene, acetic acid, acetic anhydride, water, pyridine, and the like. The (lower) alkanoylating agent is used in an amount of at least 1 mole per 1 mole of the compound [33], usually in an equimolar to a large excess amount. The reaction is usually carried out at a temperature of from around 0° C. to around 150° C., preferably from around 0° C. to around 100° C., for about 5 minutes to about 15 hours. In case of using a (lower) alkanoic acid as the (lower) alkanoylating agent, a dehydrating agent is preferably employed, which includes mineral acids such as sulfuric acid and hydrochloric acid, sulfonic acids such as p-toluenesulfonic acid, benzenesulfonic acid and ethanesulfonic acid and the like, and the reaction is preferably carried out at a temperature of from around 50° C. to around 120° C.

The nitration of the compound [33] or [34] is carried out by treating the said compound with a nitrating agent such as fuming nitric acid, concd. nitric acid, a mixed acid (e.g. nitric acid plus sulfuric acid, fuming sulfuric acid, phosphoric acid or acetic anhydride, etc.), an alkali metal nitrate plus sulfuric acid, an anhydride of nitric acid and an organic acid such as acetyl nitrate or benzoyl nitrate, nitrogen tetraoxide, nitric acid plus mercury nitrate, nitrate of acetone cyanohydrin, an alkyl nitrate plus sulfuric acid or a polyphosphoric acid, without a solvent or in the presence of a solvent such as acetic acid, acetic anhydride or sulfuric acid. The nitrating agent is preferably used in an amount of 1 to 5 moles per 1 mole of the compound [33] or [34]. The reaction is usually carried out at a temperature of from around —10° C. to around 70° C. for about 10 minutes to about 24 hours.

The hydrolysis of the compound [35] is carried out under the same reaction conditions as employed in the hydrolysis of the above compound [1a].

The reaction between the compound [37a] or [38] and the compound [8] can be carried out under the same reaction conditions as employed in the reaction between the compound [1b] and the compound [1] in the above reaction scheme-II.

The halogenation of the compound [39] can be carried out under the same reaction conditions as employed in the halogenation of the above compound [14].

The reaction of converting the compound [29b] into the compound [29a] can be carried out under the same reaction. conditions as employed in the above reaction of converting the compound [18] into the compound [19].

The reaction between the compound [39a] and the compound [15] can be carried out under the same reaction conditions as employed in the reaction between the compound [14a] and the compound [15].

The reaction of converting the compound [36] into the compound [37] can be carried out by converting the former compound into a diazonium salt thereof using sodium nitrite and an acid such as sulfuric acid, hydrochloric acid hydrobromic acid or boron fluoride in a solvent such as a (lower) alkanoic acid such as acetic acid or water, and then reacting the diazonium salt with a copper powder or a copper halide such as, for example, cuprous bromide, cuprous chloride or cupric chloride in the presence of a hydrohalogenic acid such as, for example, hydrobromic acid or hydrochloric acid, or reacting with potassium iodide in the presence or absence of a copper powder, preferably with a copper halide in the presence of a hydrohalogenic acid. The sodium nitrite is usually used in an amount of 1 to 2 moles, preferably 1 to 1.5 moles, per 1 mole of the compound [36], and the copper halide is usually used in an amount of 1 to 5 moles, preferably 1 to 4 moles, per 1 mole of the compound [36]. The reaction is usually carried out at a temperature of from around —20° C. to around 100° C., preferably from around —5° C. to around 100° C., for about 10 minutes to about 5 hours.

The halogen atoms of $R^{2'}$ and $X^9$ in the compound [37a], the compound [1a], the compound [1a'] and the compound [45] described below can be converted into each other.

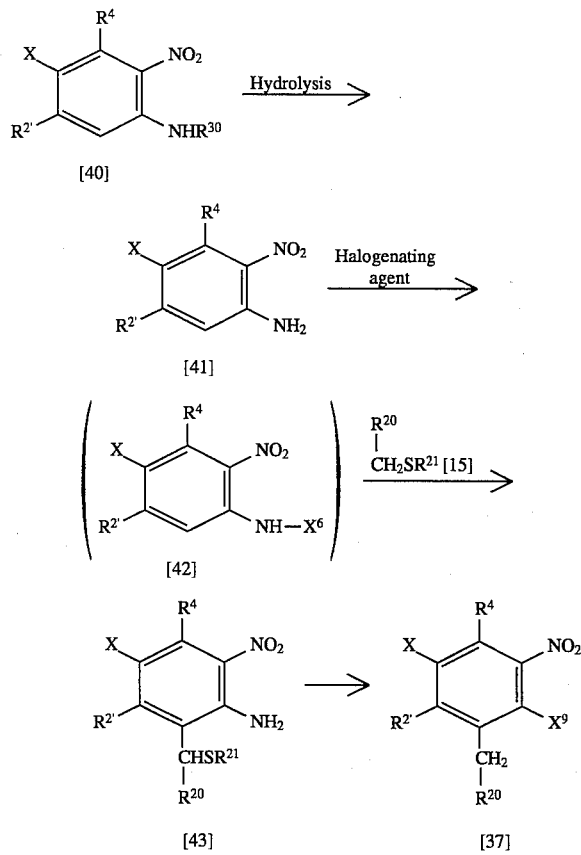

wherein $R^{2'}$, $R^{20}$, $R^{21}$, $R^{30}$, X $X^6$ $X^9$ and are as defined above.

The hydrolysis of the compound [40] can be carried out under the same reaction conditions as employed in the hydrolysis of the above compound [1a].

The halogenation of the compound [41] can be carried out under the same reaction conditions as employed in the halogenation of the compound [14] in the above reaction scheme-V.

The reaction between the compound [42] and the compound [15] can be carried out under the same reaction conditions as employed in the reaction between the compound [14a] and the compound [15].

The desulfurization of the compound [43] can be carried out under the same reaction conditions as employed in the desulfurization of the compound [18] in the above reaction scheme-V.

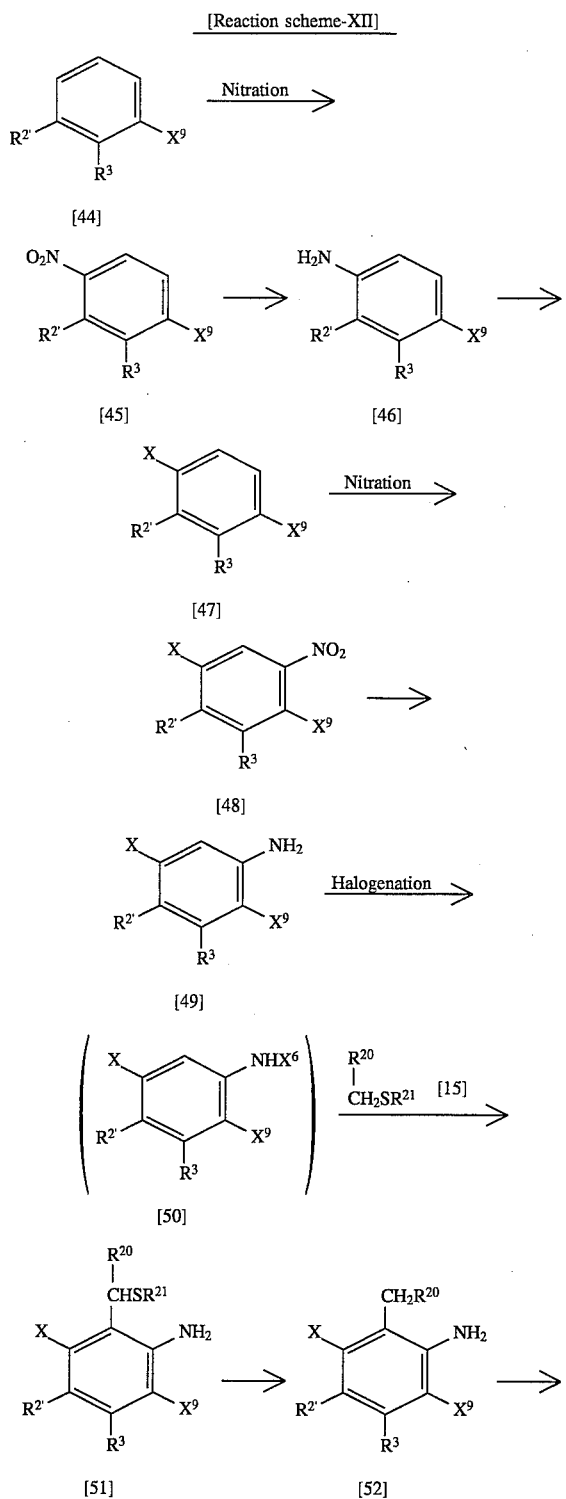

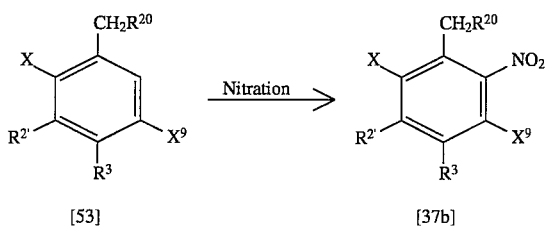

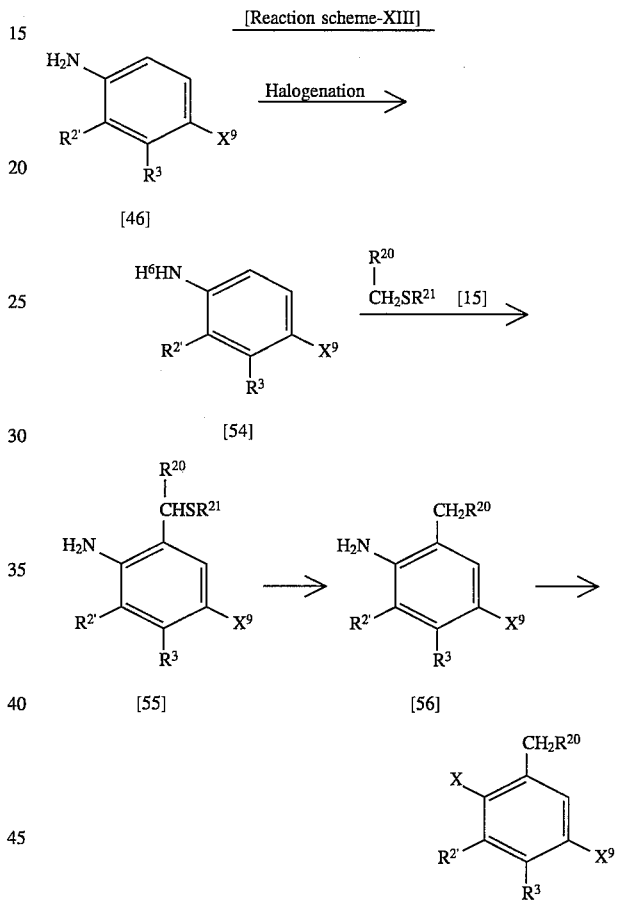

wherein $R^{2'}$, $R^3$, $X^6$, $X^9$, $R^{20}$ and $R^{21}$ are as defined above.

The nitration of each compound [44], [47] or [53] can be carried out under the same reaction conditions as employed in the nitration of the compound [33] or [34].

The reduction of the compound [45] or [48] is usually carried out by (i) reducing the compound with a catalyst for catalytic reduction in a suitable solvent, or by (ii) reducing the compound with a reducing agent such as a mixture of metal or metal salt with an acid or a mixture of metal or metal salt with hydroxide, sulfide or ammonium salt of alkali metal in a suitable inert solvent. In case of the process (i) of the catalytic reduction, the solvent employed in the reaction includes, for example, water, acetic acid, alcohols such as methanol, ethanol and isopropanol, hydrocarbons such as hexane and cyclohexane, ethers such as diethylene glycol dimethyl ether, dioxane, tetrahydrofuran and diethyl ether, esters such as ethyl acetate and methyl acetate, aprotic polar solvent such as N,N-dimethyl formamide, and the like. The catalyst for catalytic reduction employed in the reaction includes, for example, palladium, palladium black, palladium carbon, platinum, platinum oxide, copper chromite, Raney nickel, and the like. The catalyst is usually used in an amount of from 0.02 to 1.00 times weight based on the compound [45] or [48]. The reaction is usually carried out at a temperature of from around −20° C. to around 150° C., preferably from around 0° C. to room temperature at a hydrogen pressure of from 1 to 10 atm. for about 0.5 to about 10 hours. In case of using the process (ii), the employed reducing agent includes a mixture of iron, zinc, tin or tin (II) chloride with a mineral acid such as hydrochloric acid or sulfuric acid, a mixture of iron, iron (II) sulfate, zinc or tin with alkali metal hydroxide such as sodium hydroxide, sulfate such as ammonium sulfate, aqueous ammonia or ammonium chloride, and the like. The inert solvent includes, for example, water, acetic acid, methanol, ethanol, dioxane and the like. The reaction conditions of the above reduction may vary depending on a kind of the reducing agent employed. For example, the reaction is advantageously carried out at a temperature of from around 0° C. to room temperature for about 0.5 to about 10 hours when the reducing agent is a combination of tin (II) chloride and hydrochloric acid. The reducing agent is usually employed in an amount of at least 1 mole, preferably 1 to 5 moles per 1 mole of the starting compound.

The halogenation of the compound [46] or [49] and the subsequent reaction with the compound [15] can be carried out in the same reaction conditions as employed in the halogenation of the above compound [14] and the subsequent reaction with the compound [15].

The desulfurization of the compound [55] or [51] for preparing the compound [56] or [52] respectively can be carried out in the same reaction conditions as employed in the desulfurization of the above compound [18].

The reaction of converting the compound [46] or [56] into the compound [47] or [53] respectively is carried out by reacting the starting compound with nitrite of metal such as sodium nitrite or potassium nitrite in a solvent such as water in the presence of an acid to give a diazonium salt, which is then heated at from around 150° C. to around 200° C., or heated at from room temperature to around 150° C. in the presence of copper (I) bromide - hydrobromic acid, copper (I) chloride - hydrochloric acid, hydrobromic acid, potassium iodide, or an acid such as hydrochloric acid plus copper powder. The acid employed in the reaction includes, for example, hydrochloric acid, hydrobromic acid, sulfuric acid, tetrafluoroboric acid, hexafluorophosphoric acid, and the like. The acid and the nitrate of metal are usually used in an amount of from 1 to 5 moles, preferably from 1 to 3 moles, and of at least 1 mole, preferably from 1 to 1.5, moles, respectively, per 1 mole of the compound [46] or [56]. The amount of the acid employed in heating the obtained diazonium salt is usually at least 1 moles, preferably from 1 to 1.5 moles per 1 mole of the compound [56].

The deamination of the compound [52] to prepare the compound [53] is carried out by, for example, reacting the compound [52] with t-butylnitrite in the presence of a suitable solvent. The solvent employed in the reaction includes, for example, dimethyl formamide, dimethyl sulfoxide, hexamethylphosphoric acid triamide, and the like. The t-butyl nitrite is usually used in an amount of at least 1 mole, preferably from 1° to 2 moles per 1 mole of the compound [52]. The reaction is usually carried out at a temperature of from room temperature to around 150° C., preferably from room temperature to around 100° C. for about 0.1 to 5 hours.

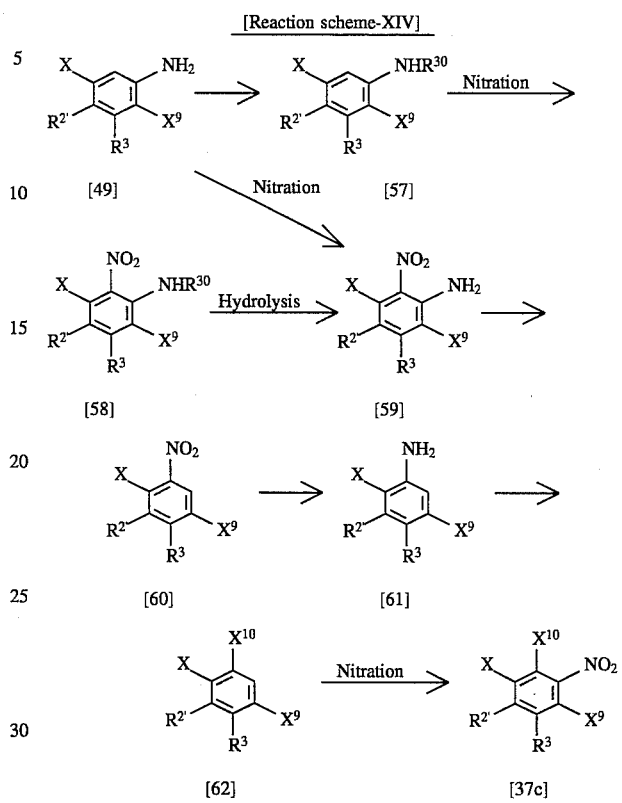

[Reaction scheme-XIV]

wherein $R^{2'}$, $R^3$, $X$, $X^9$, and $R^{30}$ are as defined above and $X^{10}$ is a halogen atom.

The reaction of converting the compound [49] into the compound [57] can be carried out under the same reaction conditions as employed in the above reaction of converting the compound [33] into the compound [34].

The nitration of the compound [49], [57] or [62] can be carried out under the same reaction conditions as employed in the above nitration of the compound [33] or [34].

The hydrolysis of the compound [58] can be carried out under the same reaction conditions as employed in the above hydrolysis of the compound [1a].

The deamination of the compound [59] to prepare the compound [60] can be carried out under the same reaction conditions as employed in the above deamination of the compound [52].

The reduction of the compound [60] can be carried out in the same reaction conditions as employed in the above reduction of the compound [45] or [48].

The reaction of converting the compound [61] into the compound [62] can be carried out in the same manner as in the above reaction of converting the compound [46] or [56] into the compound [47] or [53].

The compounds [3], [5], [7], [9], [1a], [1a'], [1b'], [29], [31] and [32], wherein $R^2$ is a saturated or unsaturated 5- to 9-membered heterocyclic ring having a substituent of oxo, can be reduced to the corresponding compounds, wherein $R^2$ is a saturated or unsaturated 5- to 9-membered heterocyclic ring having a substituent of hydroxy. The reduction can be carried out with a hydrogenating reducing agent in the presence of a suitable solvent. The reducing agent includes, for example, sodium borohydride, lithium aluminum hydride, diborane and the like. The reducing agent is usually used in an amount of at least 1 mole, preferably 1 to 5 moles per 1 mole of the starting material to be reduced. The solvent includes, for example, water, a (lower) alcohol such as methanol, ethanol or isopropanol, an ether such as tetrahydrofuran, diethyl ether or diglyme, and the like. The reaction is usually carried out at a temperature of from around −60° C. to 50° C., preferably from around −30° C. to room temperature for about 10 minutes to about 5 hours. In case of using lithium aluminum hydride or diborane as the reducing agent, nonaqueous solvent is preferably employed such as diethyl ether, tetrahydrofuran or diglyme.

In case of using sodium borohydride as the reducing agent, an inorganic base such as sodium hydroxide can also be added to the reaction system.

The compounds wherein $R^{2'}$ is a saturated or unsaturated 5- to 9-membered heterocyclic ring having a substituent selected from the group consisting of a (lower) alkyl having at least 1 of a (lower) alkanoylamino and a (lower) alkoxycarbonylamino, a (lower) alkanoylamino and a (lower) alkoxycarbonylamino can be hydrolized into the corresponding compounds wherein $R^2$ is a saturated or unsaturated 5- to 9-membered heterocyclic ring having a subsitituent selected from the group consisting of a (lower) alkyl having at least one amino and amino. The hydrolysis can be carried out under the same reaction conditions as employed in the hydrolysis of the compound [1a] in the above reaction scheme-I.

The compounds wherein $R^2$ is a saturated or unsaturated 5- to 9-membered heterocyclic ring having at least one —NH— in the ring can be converted into the compounds wherein $R^2$ is a saturated or unsaturated 5- to 9-membered heterocyclic ring substituted by at least one (lower) alkanoyl, by reacting the former compounds under the same reaction conditions as employed in the reaction of converting the compound [33] into the compound [34] in the above reaction scheme-X.

The compounds [3], [5], [7], [9], [1a], [1a'], [1b], [1b'], [29], [31] and [32] wherein $R^1$ is a phenyl having at least one (lower) alkoxy on the phenyl ring can be converted into the corresponding compounds wherein $R^1$ is a phenyl having at least one hydroxy on the phenyl ring, by heating the former compounds in an aqueous hydrobromic acid solution.

The compound [1] wherein $R^3$ and/or $R^4$ is a halogen atom can be converted into the corresponding compound [1] wherein $R^3$ and/or $R^4$ is hydroxy, by treating the former compound in water and a basic compound such as sodium hydroxide, potassium hydroxide or barium hydroxide at from room temperature to around 200° C., preferably from room temperature to around 150° C. for about 1 to 15 hours.

[Reaction scheme-XV]

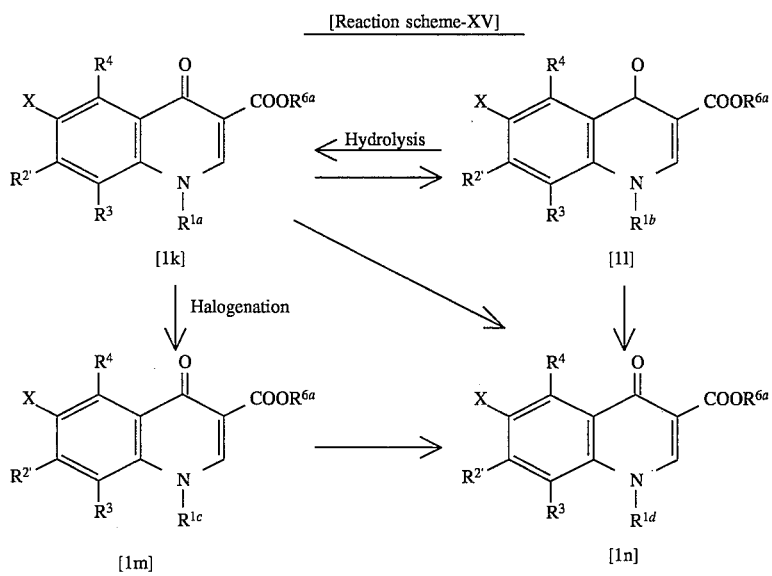

wherein $R^{2'}$, $R^3$, $R^4$, and X are as defined above, and $R^{6a}$ is hydrogen atom or a (lower) alkyl, $R^{1a}$ is a (lower) alkyl having 1 to 3 of hydroxy, $R^{1b}$ is a (lower) alkyl having 1 to 3 of a (lower) alkanoyloxy, $R^{1c}$ is a (lower) alkyl having 1 to 3 of halogen atoms and $R^{1d}$ is a (lower) alkenyl.

The reaction of converting the compound [1k] into the compound [1s] can be carried out under the same reaction conditions as employed in the above reaction of converting the compound [33] into the compound [34].

The hydrolysis of the compound [1i] can be carried out under the same reaction conditions as employed in the above hydrolysis of the compound [1a].

The halogenation of the compound [1k] can be carried out under the same reaction conditions as employed in the above halogenation of the compound [2].

The reaction of converting the compound [1k] into the compound [1n] is carried out in a suitable solvent or without a solvent in the presence of a hydrohalogenic acid such as hydochloric acid or hydrobromic acid, an inorganic acid such as sulfuric acid, boric acid or potassium hydrogensulfate, or an organic acid such as oxalic acid. The solvent employed in the reaction includes, for example, water, an ether such as dioxane, tetrahydrofuran or diethyl ether, a halogenated hydrocarbon such as dichloromethane, chloroform or carbon tetrachloride, an aromatic hydrocarbon such as benzene, toluene or xylene, or a mixture thereof. The reaction is usually carried out at a temperature of from around 50° C. to around 350° C., preferably from around 80° C. to around 300° C. for about 10 minutes to about 10 hours.

The reaction of converting the compound [1z] into the compound [1n] is carried out in a suitable solvent or without a solvent. The solvent employed in the reaction may be any which is exemplified in the above reaction of converting the compound [1k] into the compound [1n]. The reaction is usually carried out at a temperature of from room temperature to around 150° C., preferably from room temperature to around 100° C. for about 10 minutes to about 10 hours. The reaction may also be conducted in the presence of an inorganic base such as sodium carbonate, potassium carbonate, sodium hydrogen carbonate, potassium hydrogen carbonate, sodium hydroxide, potassium hydroxide, lithium salt such as lithium chloride or lithium carbonate, or an organic base such as DBU, pyridine, triethanol amine or triethyl amine.

The reaction of converting the compound [1m] into the compound [1n] is carried out in a suitable solvent in the presence of a basic compound. The solvent and the basic compound employed in the reaction may be any which is exemplified in the above reaction of converting the compound [1z] into the compound [1n]. The reaction is usually carried out at a temperature of from room temperature to around 200° C., preferably from room temperature to around 150° C. for about 1 to about 10 hours.

The compounds [1k], [1i], [1m] and [1n] wherein $R^{6a}$ is a (lower) alkyl can be converted into the corresponding compounds wherein $R^{6a}$ is hydrogen atom, by hydrolyzing the former compounds under the same reaction conditions as employed in the above hydrolysis of the compound [1a].

In the hydrolysis of the compound [1i] wherein $R^{6a}$ is a (lower) alkyl, $R^{6a}$ is also hydolyzed in some cases to give the compound [1z] wherein $R^{6a}$ is hydrogen atom, which can easily be separated from the reaction mixture.

In the halogenation of the compound [1k] wherein $R^{6a}$ is hydrogen atom, the carboxy in the compound is also halogenated in some cases but this one can be easily separated from the reaction mixture.

The compounds [1a] in the reaction scheme-I and the compounds [1b] and [1b] in the reaction scheme-II are useful not only as an intermediate for preparing the compound [1] of the present invention with antimicrobial activities, but also as an antimicrobial agent because they also have antimicrobial activities.

The compound [1] of the present invention can easily be converted into a salt thereof by treating with a pharmaceutically acceptable acid or base. The acid includes inorganic acids such as hydrochloric acid, sulfuric acid, phosphoric acid and hydrobromic acid and organic acids such as oxalic acid, maleic acid, fumaric acid, malic acid, tartaric acid, citric acid, benzoic acid, lactic acid, methanesulfonic acid and propionic acid. The base includes sodium hydroxide, potassium hydroxide, calcium hydroxide, sodium carbonate, potassium hydrogen carbonate, and the like.

The compound thus obtained can easily be isolated and purified by conventional methods, such as, for example, extraction with solvents, dilution method, recrystallization, column chromatography and preparative thin layer chromatography.

The compound [1] of the present invention or salts thereof show an excellent antimicrobial activity against mycoplasma, Pseudomonas aeruginosa, anaerobic bacteria, resistant cells against various antimicrobials, clinically isolated bacteria, and gram negative and gram positive bacteria such as Enterococcus faecalis and Staphylococcus pyogenes and hence are useful as an antimicrobial agent for the treatment of diseases induced by these microorganisms. These compounds also show low toxicity and less side effect and are characteristic in good absorbability and in sustained activity. Moreover, the compounds are highly excreted via urine and hence are useful for the treatment of urinary infectious diseases, and further because of easy excretion via bile, they are also useful for the treatment of intestinal infectious diseases.

Among the compounds [1] of the present invention, the preferable ones are the compounds wherein $R^1$ is unsubstituted cyclopropyl, X is chlorine or fluorine atom, most preferably fluorine atom, $R^4$ is a (lower) alkyl, preferably methyl or ethyl, most preferably methyl, and $R^3$ is a (lower) alkyl, preferably methyl or ethyl, most preferably methyl, or a halogen atom, preferably chlorine atom or fluorine atom, most preferably fluorine atom.

The absorbability of the compounds of the present invention in the living body can be increased by converting them into the corresponding salt such as, for example, lactate or hydrochloride.

The compounds of the present invention are usually used in the form of a usual pharmaceutical preparation. The pharmaceutical preparation can be prepared in admixture with conventional pharmaceutically acceptable diluents or carriers, such as fillers, bulking agents, binding agents, wetting agents, disintegrators, surfactants and lubricating agents. The pharmaceutical preparation includes various preparations suitable for treatment of the diseases, for example, tablets, pills, powders, solutions, suspensions, emulsions, granules, capsules, suppositories, injections such as solutions and suspensions, and the like. In the preparation of tablets, there may be used any conventional carriers, for example, excepients such as lactose, white sugar, sodium chloride, glucose, urea, starches, calcium carbonate, kaolin, crystalline cellulose and silicate, binding agents such as water, ethanol, propanol, simple syrup, glucose solution, starch solution, gelatin solution, carboxymethyl cellulose, shellac, methyl cellulose, potassium phosphate and polyvinylpyrrolidone, disintegrators such as dry starch, sodium alginate, agar powder, laminaran powder, sodium hydrogen carbonate, calcium carbonate, polyoxyethylene sorbitan fatty acid esters, sodium laurylsulfate, stearic monoglyceride, starches and lactose, disintegration inhibitors such as white sugar, stearin, cacao butter and hydrogenated oils, absorption promoters such as quaternary ammonium salts and sodium laurylsulfate, wetting agents such as glycerin and starches, adsorbents such as starches, lactose, kaolin, bentonite and colloidal silicates, rublicants such as purified talc, stearates, boric acid powder and polyethylene glycol, and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carries, including excipients such as glucose, lactose, starches, cacao butter, hydrogenated vegetable oils, kaolin and talc, binding agents such as gum arabic powder, tragacanth powder, gelatin and ethanol, disintegrators such as laminaran and agar, and the like. In the preparation of suppositories, there may be used conventional carriers, such as, for example, polyethylene glycol, cacao butter, higher alcohols, higher alcohol esters, gelatin and semi-synthetized glycerides. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, aqueous lactic acid solution, ethyl alcohol, propylene glycol, ethoxylated isostearyl alcohol, polyoxylated isostearyl alcohol or polyoxyethylene sorbitan fatty acid esters. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, preservatives, perfumes, flavors, sweetening agents, and other medicaments. The preparations in the form of a paste, cream or gel may be prepared by using as a diluent white vaseline, paraffin, glycerin, cellulose derivatives, polyethylene glycol, silicone, bentonite, or the like. When the compound of the active ingredient precipitates in the injection, an acid such as, for example, methanesulfonic acid, propionic acid, hydrochloric acid, succinic acid or lactic acid may be added to the injection as required to preserve the injection in a stable solution.

The pharmaceutical preparation of the present invention may also be in the form of an infusable or injectable solution containing the above compound [1] or a salt thereof such as lactate and an acid not producing a precipitate. The acid not producing a precipitate includes, for example, lactic acid, methanesulfonic acid, propionic acid, hydrochloric acid, succinic acid, and the like, preferably lactic acid. In case of using lactic acid, the acid is usually used in an amount of from around 0.1 to around 10% by weight, preferably from about 0.5 to around 2% by weight, based on the weight of the above infusable or injectable solution. In case of using an acid other than lactic acid, the acid is usually used in an amount of from around 0.05 to around 4% by weight, preferably from around 0.3 to around 2% by weight, based on the weight of the above solution. The above infusable or injectable solution may optionally be added with conventional additives, which includes, for example, a thickener, an absorption promoter or inhibitor, a crystallization inhibitor, a complex-forming agent, an antioxidant, an isotonicity-giving agent, or a hydrating agent, and the like. The pH of the solution can properly be adjusted by adding an alkali such as sodium hydroxide, and is usually adjusted within the range of from 2.5 to 7. The infusable or injectable solution thus prepared has an excellent stability, and can be stored and preserved for a long time with retaining the solution state.

The active compounds [1] or salts thereof may be contained in any amount in the preparations, and are usually contained in an amount of from 1 to 70% by weight based on the whole weight of the preparations.

The pharmaceutical preparations of the present invention can be administered in any methods. Suitable method for administration may be selected in accordance with the preparation form, age and sex of patients, severity of the diseases, and the like. For instance, tablets, pills, solutions, suspensions, emulsions, granules and capsules are administered in oral route. In case of injection, it is administered intravenously in a single form or together with an auxiliary liquid such as glucose or amino acid solution. The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of patients, severity of the diseases, and the like, usually in the range of about 0.2 to about 100 mg of the active compound [1] or a salt thereof per 1 kg body weight of the patient per day. The preparation is usually administered by dividing into 2 to 4 times per day.

The present invention is illustrated by the following Reference Examples, Examples, Experiments and Preparations. It is to be understood that the present invention is not limited to these Examples or Experiments and various changes and modifications can be made without departing from the scope and spirit of the present invention.

Reference Example 1

To 2,6-dichlorotoluene (200 g) is added dropwise fuming nitric acid (d=1.52, 206 ml) at 25° to 30° C. After stirring for 30 minutes at room temperature, the mixture is poured into ice-water, extracted with diethyl ether, and the extract is washed with an aqueous sodium hydrogen carbonate solution and then dried. The solvent is distilled off under reduced pressure to give 2,6-dichloro-3-nitrotoluene as yellow crystals (253.2 g).

$^1$H-NMR (CDCl$_3$) δppm: 2.57 (3H, s), 7.42 (1H, d, J=7 Hz), 7.58 (1H, d, J=7 Hz)

Reference Example 2

A mixture of 2,6-dichloro-3-nitrotoluene (253.2 g), anhydrous dimethyl sulfoxide (1.2 l), Kurocat F (KF) (357g) and 18-crown-6 (2.5 g) is stirred at 160° C. for 6 hours. After cooling, the mixture is poured into ice-water, extracted with diethyl ether, and the extract is washed with water and dried. The solvent is distilled off under reduced pressure and the residue is distilled under reduced pressure to give 2,6-difluoro-3-nitrotoluene (96.1 g), boiling point: 110°–112° C./18 mmHg.

$^1$H-NMR (CDC13) δ ppm: 2.30 (3H, t, J=2 Hz), 7.01 (1H, ddd, J=1.8 Hz, 7.7 Hz, 9.5 Hz), 7.97 (1H, dt, J=5.8 Hz, 8.7 Hz)

Reference Example 3

To acetic acid (1.2 l) are added 5% Pd-C (24 g) and 2,6-difluoro-3-nitrotoluene (238.7 g) and the mixture is subjected to catalytic reduction at room temperature under 4.5 atoms. The 5% Pd-C is filtered off and the acetic acid is distilled off under reduced pressure. The residue is poured into ice-water, neutralized, extracted with dichloromethane, and the extract is washed with water and dried. The solvent is distilled off under reduced pressure and the residue is distilled under reduced pressure to give 2,4-difluoro-3-methylaniline (138 g), colorless oils, b.p.: 75° C./11 mmHg.

$^1$H-NMR (CDCl$_3$) δ ppm: 2.17 (3H, t, J=2 Hz), 3.3–3.7 (2H, brs), 6.4–6.7 (2H, m)

Reference Example 4

To 2,4-difluoro-3-methylaniline (20 g) are added 42% tetrafluoroboric acid (56 ml) and water (28 ml) under ice cooling and thereto a solution of sodium nitrite (10 g) in water (20 ml) is added dropwise at below 10° C. After dropwise addition, the mixture is stirred at 0° C. for 15 minutes and the formed crystals are filtered, which is washed with a mixture of ethanol—diethyl ether (1:2), then with diethyl ether, followed by drying under reduced pressure to give 2,4-difluoro-3-methylbenzene diazonium tetrafluoroborate (28.95 g), m.p. 114–115° C.

Reference Example 5

2,4-Difluoro-3-methylbenzene diazonium tetrafluoroborate (28.95 g) is heated at 180° C., whereby the decomposition starts. The inner temperature is raised to 200° C. The product is taken out of the reaction system. After the reaction is completed, distillates (7.05 g) are obtained, which is distilled under normal pressure to give 2,3,6-trifluorotoluene (7.02 g), as colorless oil, b.p. 92° C.

$^1$H-NMR (CDCl$_3$) δ ppm: 2.22 (3H, t, J=1.8 Hz), 6.7–7.1 (2H, m)

Reference Example 6

To 2,3,6-trifluorotoluene (55 g) is added conc. sulfuric acid (366 ml) and the mixture is cooled to 0° C. Thereto a solution of potassium nitrate (44 g) in conc. sulfuric acid (120 ml) is added dropwise at below 10° C. and then the mixture is stirred for 15 minutes. The mixture is poured into ice-water, extracted with diethyl ether, and the extract is washed with water and dried. The solvent is distilled off to give 2,3,6-trifluoro-5-nitrotoluene (68.25 g), as yellow oil.

$^1$H-NMR (CDCl$_3$) δ ppm: 2.36 (3H, t, J=2 Hz), 7.83. (1H, q-like, J=8.2 Hz)

Reference Example 7

To acetic acid (350 ml) are added 5% Pd-C (3.5 g) and 2,3,6-trifluoro-5-nitrotoluene (35 g) and the mixture is subjected to catalytic reduction at room temperature under atomospheric pressure. 5% Pd-C is filtered off and the acetic acid is distilled off under reduced pressure. The residue is poured into ice-water, neutralized, extracted with dichloromethane, and the extract is washed with water and dried. The solvent is distilled off under reduced pressure and the obtained residue is distilled under reduced pressure to give 2,4,5-trifluoro-3-methylaniline (22.86 g), as yellow crystals, b.p. 85° C./20 mmHg.

$^1$H-NMR (CDCl$_3$) δ ppm: 2.19 (3H, t, J=2 Hz), 3.3–3.7 (2H, brs), 6.42 (1H, dt, J=8 Hz, 11 t Hz)

Reference Example 8

To anhydrous dichloromethane (170 ml) are added 2,4,5-trifluoro-3-methylaniline (16.89 g) and dimethyl sulfide (11 ml). Thereto N-chlorosuccinimide (17.2 g) is added gradually below 5° C. After stirring for 30 minutes, triethylamine (21 ml) is added dropwise and the mixture is refluxed over night. After the mixture is cooled and made alkaline with 5% aqueous sodium hydroxide solution, the resultant is extracted with dichloromethane, and the extract is washed with water and dried. The solvent is distilled off under reduced pressure and the residue is purified by silica-gel column-chromatography (dichloromethane: n-hexane =1:1) to give 2,4,5-trifluoro-3-methyl-6-methylthiomethylaniline (8.3 g).

$^1$H-NMR (CDCl$_3$) δ ppm: 2.02 (3H, s), 2.20 (3H, t, J=2 Hz), 3.79 (2H, d, J=1.9 Hz), 3.9–4.1 (2H, brs)

Reference Example 9

To 2,4,5-trifluoro-3-methyl-6-methylthiomethylaniline (10.67 g) are added ethanol (300 ml) and Raney nickel (100 g, wet) and the mixture is stirred at room temperature for 30 minutes. After Raney nickel is filtered off, the filtrate is concentrated, diluted with water, extracted with dichloromethane, and the extract is washed with water and dried. The solvent is distilled off under reduced pressure and the residue is purified by silica-gel column-chromatography (dichloromethane: n-hexane =1:1) to give 2,4,5-trifluoro-3,6-dimethylaniline (5.89 g), as yellow crystals.

$^1$H-NMR (CDCl$_3$) δ ppm: 2.10 (3H, d, J=1.7 Hz), 2.18 (3H, s-like), 3.4–3.7 (2H, brs)

Reference Example 10

A solution of t-butyl nitrite (4.56 g) in anhydrous dimethylformamide (26.5 ml) is stirred with heating at 50°–52° C. and thereto a solution of 2,4,5-trifluoro-3,6-dimethylaniline (4.24 g) in anhydrous dimethylformamide (40 ml) is added dropwise at 50°–52° C. over a period of 30 minutes. The mixture is further stirred at the same temperature for 30 minutes. After cooling, the mixture is poured into ice-water, extracted with diethyl ether, and the extract is washed with water, and then with diluted hydrochloric acid and dried. The diethyl ether is distilled off under atomospheric pressure and the residue is concentrated and distilled under atomospheric pressure to give 2,3,5-trifluoro-4-methyltoluene (1.9 g), as yellow oil, b.p. 120°–125° C.

$^1$H-NMR (CDC13) δ ppm: 2.17 (3H, s-like), 2.25 (3H, d, J=1.7 Hz), 6.62 (1H, ddd, J=2 Hz, 6.3 Hz, 8.3 Hz)

Reference Example 11

To 2,3,5-trifluoro-4-methyltoluene (1.9 g) is added conc. sulfuric acid (19 ml) and the mixture is cooled to 0° C., to which a solution of potassium nitrate (1.71 g) in conc. sulfuric acid (4.6 ml) is added dropwise below 10° C. and the mixture is stirred for 15 minutes. The mixture is poured into ice-water, extracted with diethyl ether, and the extract is washed with water and dried. The solvent is distilled off under reduced pressure and the residue is purified by silica-gel column-chromatography (dichloro-methane: n-hexane= 1:6) to give 2,3,6-trifluoro-4-methyl-5-nitrotoluene (1.9 g).

$^1$H-NMR (CDCl$_3$) δ ppm: 2.29 (3H, t, J=1.5 Hz), 2.32 (3H, d, J=2.4 Hz)

Reference Example 12

To 2,3,6-trifluoro-4-methyl-5-nitrotoluene (1.9 g) are added 2-methoxyethanol (9.9 ml), water (1.1 ml), N-methylpiperazine (4.1 ml) and triethylamine (5.2 ml) and the mixture is refluxed for 25 hours. After the reaction is completed, water is added and the resultant is extracted with diethyl ether, and the extract is washed with water and dried. The solvent is distilled off under reduced pressure and the residue is purified by silica-gel column-chromatography (dichloromethane: methanol=40:1) to give 2-(4-methyl-1-piperazinyl)-3,6-difluoro-4-methyl-5-nitrotoluene (1.73 g).

$^1$H-NMR (CDCl$_3$) δ ppm: 2.25 (6H, d, J=2.6 Hz), 2.36 (3H, s), 2.4–2.6 (4H, br), 3.0–3.3 (4H, br)

Reference Example 13

To 2-(4-methyl-1-piperazinyl)-3,6-difluoro-4-methyl-5-nitrotoluene (1.73 g) are added anhydrous dimethyl sulfoxide (18 ml), potassium fluoride (0.53 g) and cyclopropylamine (2.2 ml) and the mixture is stirred at 100° C. for 23 hours. After cooling, the mixture is poured into ice-water, extracted with dichloromethane and the extract is dried. The solvent is distilled off under reduced pressure and the residue is purified by silica-gel column-chromatography (dichloromethane: methanol=40:1) to give 3-(4-methyl-1-piperazinyl)-4-fluoro-2,5-dimethyl-6-nitro-N-cyclopropylaniline (1.65 g).

Reference Example 14

To 2,4-difluoro-3-methylaniline (5.0 g) are added anhydrous dichloromethane (100 ml) and dimethyl sulfide (3.5 ml). Thereto N-chlorosuccinimide (5.6 g) is added below 0° C. and the mixture is stirred for 15 minutes. Thereto triethylamine (4.8 ml) is added and the mixture is refluxed for 4 hours. After cooling, the mixture is poured into ice-water, made alkaline with 5% aqueous sodium hydroxide solution, extracted with dichloromethane and the extract is dried. The solvent is distilled off under reduced pressure and the residue is purified by silica-gel column-chromatography (dichloromethane: n-hexane =1:1) to give 2,4-difluoro-3-methyl-6-methylthiomethylaniline (4.9 g).

$^1$H-NMR (CDCl$_3$) δ ppm: 1.99 (3H, s), 2.17 (3H, t, J=1.8 Hz), 3.64 (2H, s), 3.93 (2H, brs), 6.56 (1H, dd, J=1.8 Hz, 9.4 Hz)

Reference Example 15

To a solution of Raney nickel (50 g) in ethanol (100 ml) is added a solution of 2,4-difluoro-3-methyl-6-methylthiomethylaniline (4.79 g) in ethanol (30 ml) at room temperature with stirring, followed by stirring at room temperature for 30 minutes. The Raney nickel is filtered off and the filtrate is diluted with water, extracted with dichloromethane, and the extract is washed with water and dried. The solvent is distilled off under reduced pressure to give 2,4-difluoro-3,6-dimethylaniline (3.14 g).

$^1$H-NMR (CDCl$_3$) δ ppm: 2.14 (6H, s-like), 3.3–3.6 (2H, br), 6.56 (1H, dd, J=1.5 Hz, 9.7 Hz)

Reference Example 16

To 2,4-difluoro-3,6-dimethylaniline (3.1 g) are added 42% tetrafluoroboric acid (9 ml) and water (4.5 ml) with stirring and under ice-cooling, followed by dropwise addition of a solution of sodium nitrite (1.6 g) in water (3.2 ml) below 10° C. After stirring the mixture at 0° C. for 15 minutes, the resulting crystals are filtered, washed with a mixture of ethanol-diethyl ether (1:2) and then with diethyl ether, followed by drying under reduced pressure to give 2,4-difluoro-3,6-dimethylbenzene diazonium tetrafluoroborate (1.78 g).

Reference Example 17

2,4-Difluoro-3,6-dimethylbenzene diazonium tetrafluoroborate (1.78 g) is heated at 180° C., whereby decomposition thereof starts. The inner temperature is raised to 200° C. The product is taken out of the reaction system to give 2,3,6-trifluoro-4-methyltoluene (0.3 g), as yellow oil, b.p. 120–125° C.

$^1$H-NMR (CDCl$_3$) δ ppm: 2.17 (3H, s-like), 2.25 (3H, d, J=1.7 Hz), 6.62 (1H, ddd, J=2 Hz, 6.3 Hz, 8.3 Hz)

Reference Example 18

To 6-methyl-2,3,4,5-tetrafluorobenzoic acid (5.60 g) is added thionyl chloride (9.8 ml) and the mixture is refluxed for 1 hour. After concentrating, 6-methyl-2,3,4,5-tetrafluorobenzoyl chloride (5.20 g) is obtained as a colorless oil, b.p. 82° C./23 mmHg.

NMR (CDCl$_3$) δ ppm: 2.35 (3H, m)

Separately, two drops of carbon tetrachloride are added to a solution of metallic magnesium (0.56 g) in absolute ethanol (0.9 ml). When the reaction starts, a mixture of diethyl malonate (3.6 ml), absolute ethanol (1.6 ml) and anhydrous toluene (6 ml) is added dropwise below 60° C. After stirring at 60° C. for 1 hour, the reaction mixture is cooled to 0° C. and thereto a solution of 6-methyl-2,3,4,5-tetrafluorobenzoyl chloride (5.00 g) prepared above in toluene (5 ml) is added dropwise. After stirring for 30 minutes, a mixture of conc. sulfuric acid (0.4 ml) and water (6 ml) is added and the mixture is extracted with diethyl ether, and the extract is dried over magnesium sulfate and concentrated to give diethyl 6-methyl-2,3,4,5-tetrafluorobenzoylmalonate (8 g) as an yellow oil.

Reference Example 19

To diethyl 6-methyl-2,3,4,5-tetrafluorobenzoyl-malonate (8 g) are added water (20 ml) and p-toluenesulfonic acid (80 mg) and the mixture is refluxed for 2.5 hours. After cooling, the resultant is extracted with diethyl ether, and the extract is dried over magnesium sulfate and concentrated to give ethyl 6-methyl-2,3,4,5-tetrafluorobenzoylacetate (4.5 g).

Reference Example 20

To ethyl 6-methyl-2,3,4,5-tetrafluorobenzoylacetate (4.20 g) are added acetic anhydride (3.7 g) and ethyl orthoformate (4 ml) and the mixture is refluxed for 1 hour. After concentrating, ethyl 2-(6-methyl-2,3,4,5-tetrafluorobenzoyl)-3-ethoxyacrylate (5 g) is obtained.

Reference Example 21

Ethyl 2-(6-methyl-2,3,4,5-tetrafluorobenzoyl)-3-ethoxyacrylate (5 g) is dissolved in ethanol (25 ml) and thereto cyclopropylamine (1.0 g) is added dropwise under ice-cooling. After stirring at room temperature for 30 minutes, the mixture is concentrated and the residue is purified with column chromatography (silica-gel, dichloromethane: n-hexane =1:1) to give ethyl 2-(6-methyl-2,3,4,5-tetrafluorobenzoyl)-3-cyclopropylaminoacrylate (4.74 g), as white plates, m.p. 78°–79° C. (recrystallized from petroleum ether-n-hexane).

Reference Example 22

Ethyl 2-(6-methyl-2,3,4,5-tetrafluorobenzoyl)-3-cyclopropylaminoacrylate (4.50 g) is dissolved in anhydrous dioxane (26 ml) and thereto 60% sodium hydride (580 mg) is gradully added under ice-cooling. After stirring at room temperature for 30 minutes, the reaction mixture is poured into ice-water and extracted with dichloromethane. The extract is dried over magnesium sulfate and concentrated. The residue is added with diethyl ether and crystals are filtered, which are recrystalized from dichloromethane-n-hexane to give ethyl 1-cyclopropyl-6,7,8-trifluoro-5-methyl-1,4-dihydro-4-oxoquinoline-3-carboxylate (4.19 g), as white needles, m.p. 180°–183° C.

Reference Example 23

To ethyl 1-cyclopropyl-6,7,8-trifluoro-5-methyl-1,4-dihydro-4-oxoquinoline-3-carboxylate (4.10 g) are added 90% acetic acid—conc. hydrochloric acid (4:1, 81.25 ml) and the mixture is refluxed for 2 hours. After cooling, the precipitated crystals are isolated, washed with water, ethanol, and diethyl ether in this order to give 1-cyclopropyl-6,7,8-trifluoro-5-methyl-1,4,-dihydro-4-oxoquinoline-3-carboxylic acid (3.47 g), as white needles, m.p. 218°–220° C.

Reference Examples 24

To 2,4,5-trifluoro-3-methylniline (1 g) is added acetic anhydride (3 ml) at room temperature with stirring and the mixture is stirred for 15 minutes. The reaction mixture is poured into ice-water, extracted with dichloromethane, and the extract is washed with water and dried. The solvent is distilled off to give 2,4,5-trifluoro-3-methyl-N-acetylaniline (1.14 g), as white crystals.

$^1$H-NMR (CDCl$_3$) δ ppm: 2.21 (3H, s), 2.24 (3H, t, J=2.1 Hz), 7.2–7.5 (1H, brs), 8.10 (1H, dt, J=7.9 Hz, 12 Hz)

Reference Examples 25

To 2,4,5-trifluoro-3-methyl-N-acetylaniline (1.94 g) is added conc. sulfuric acid (19 ml) and the mixture is cooled to 0° C. Thereto potassium nitrate (2 g) is added below 20° C. and the mixture is stirred for 15 minutes. The reaction mixture is poured into ice-water, extracted with dichloromethane and the extract is dried. The solvent is distilled off under reduced pressure to give 2,4,5-trifluoro-3-methyl-6-nitro-N-acetylaniline (2.08 g), as white crystals.

$^1$H-NMR (CDCl$_3$) δ ppm: 2.21 (3H, s), 2.34 (3H, t, J=2.2 Hz), 7.3–7.5 (1H, brs)

Reference Examples 26

To 2,4,5-trifluoro-3-methyl-6-nitro-N-acetyl-aniline (2.08 g) are added ethanol (30 ml) and 10% hydrochloric acid (30 ml) and the mixture is refluxed for 3 hours. After cooling, the reaction mixture is poured into ice-water, neutralized with potassium carbonate, extracted with dichloromethane and the extract is dried. The solvent is distilled off under reduced pressure to give 2,4,5-trifluoro-3-methyl-6-nitroaniline (2.05 g), as brown crystals.

$^1$H-NMR (CDCl$_3$) δ ppm: 2.29 (3H, s), 2.29 (3H, t, J=2.1 Hz), 5.5–5.9 (2H, brs)

Reference Examples 27

To a solution of t-butyl nitrite (1.87 g) in anhydrous dimethylformamide (10.9 ml) is added dropwise a solution of 2,4,5-trifluoro-3-methyl-6-nitroaniline (2.05 g) in anhydrous dimethylformamide (16.4 ml) with stirring at 50°–52° C. and the mixture is stirred at the same temperature for 30 minutes. After cooling, the reaction mixture is poured into ice-water, extracted with diethyl ether, and the extract is washed with water and dried. The solvent is distilled off under reduced pressure and the obtained residue is purified by silica-gel column-chromatography (eluent; dichloromethane: n-hexane=1:4) to give 2,3,6-trifluoro-4-nitrotoluene (0.7 g).

$^1$H-NMR (CDCl$_3$) δ ppm: 2.35 (3H, t, J=2.1 Hz), 7.62 (1H, ddd, J=2.6 Hz, 5.7 Hz, 8.3 Hz)

Reference Examples 28

To acetic acid (10 ml) are added Pd-C (0.1 g) and 2,3,6-trifluoro-4-nitrotoluene (0.7 g) and the mixture is subjected to catalytic reduction at room temperature under atmospheric pressure. 5% Pd-C is filtered and the acetic acid is distilled off under reduced pressure. The residue is poured into ice-water, neutralized, extracted with dichloromethane, and the extract is washed with water and dried. The solvent is distilled off under reduced pressure to give 2,3,5-trifluoro-4-methylailine (0.48 g).

$^1$H-NMR (CDCl$_3$) δ ppm: 2.08 (3H, t, J=1.8 Hz), 3.6–4.0 (2H, brs), 6.26 (1H, ddd, J=2.2 Hz, 6.8 Hz, 9.0 Hz)

Reference Example 29

To conc. sulfuric acid (3 ml) is added sodium nitrite (0.3 g). The mixture is stirred at 70° C. for 10 minutes and then cooled to below 40° C. and thereto a solution of 2,3,5-trifluoro-4-methylaniline (0.48 g) in acetic acid (5 ml) is added dropwise below 40° C. After stirring for 30 minutes, the reaction mixture is added dropwise to a solution of copper (I) chloride (1.04 g) in conc. hydrochloric acid (10.4 ml) and the mixture is stirred at 80° C. for 30 minutes and then cooled. The resultant mixture is poured into ice-water, extracted with dichloromethane, and the extract is washed with water and dried. The solvent is distilled off under reduced pressure and purified by silica-gel column-chromatography (eluent; dichloromethane: n-hexane=1:4) to give 2,3,6-trifluoro-4-chlorotoluene (0.22 g).

$^1$H-NMR (CDCl$_3$) δ ppm: 2.20 (3H, t, J=2 Hz), 6.90 (1H, ddd, J=2.5 Hz, 5.8 Hz, 8.3 Hz)

Reference Examples 30

To 2,3,6-trifluoro-4-chlorotoluene (0.22 g) is added conc. sulfuric acid (3 ml) and the mixture is cooled to 0° C. Thereto potassium nitrate (0.18 g) is added and the mixture is stirred for 15 minutes under ice-cooling. The reaction mixture is poured into ice-water, extracted with dichloromethane, and the extract is washed with a saturated aqueous solution of sodium hydrogen carbonate, then with water and dried. The solvent is distilled off under reduced pressure to give 2,3,6-trifluoro-4-chloro-5-nitrotoluene (0.17 g).

$^1$H-NMR (CDCl$_3$) δ ppm: 2.33 (3H, t, J=2.2 Hz)

Reference Examples 31

To 2,3,6-trifluoro-4-chloro-5-nitrotoluene (0.17 g) are added ethanol (3.3 ml), water (0.5 ml), N-methyl-piperazine (0.45 ml) and triethylamine (0.56 ml) and the mixture is refluxed for 24 hours. After the reaction is completed, water is added to the reaction mixture and the mixture is extracted with diethyl ether, and the extract is washed with water and dried. The solvent is distilled off under reduced pressure and the residue is purified by silica-gel column-chromatography (eluent; dichloromethane: methanol =20:1) to give 2-(4-methyl-1-piperazinyl)-3,6-difluoro-4-chloro-5-nitrotoluene (0.13 g).

To the thus obtained 2-(4-methyl-1-piperazinyl)-3,6-difluoro-4-chloro-5-nitrotoluene (0.13 g) are added anhydrous dimethylformamide (2 ml), potassium fluoride (37 mg) and cyclopropylamine (0.15 ml) and the mixture is stirred at 100° C. for 3 hours. After cooling, the reaction mixture is poured into ice-water, extracted with dichloromethane and the extract is dried. The solvent is distilled off under reduced pressure and purified by silica-gel column-chromatography (eluent; dichloromethane: methanol=10:1) to give 3-(4-methyl-1-piperazinyl)-4-fluoro-5-chloro-2-methyl-6-nitro-N-cyclopropylaniline (0.14 g).

$^1$H-NMR (CDCl$_3$) δ ppm: 0.4–0.5 (2H, m), 0.6–0.8 (2H, m), 2.22 (3H, s), 2.36 (3H, s), 2.4–2.7 (4H, brs), 3.1–3.3 (4H, brs), 4.1–4.2 (1H, brs)

Reference Examples 32

Employing 3-chloro-2,4,5-trifluoro-6-methylbenzoic acid (185 mg) and thionyl chloride (600 µl), the procedure of Reference Example 18 is repeated to give 3-chloro-2,4,5-trifluoro-6-methylbenzoyl chloride (183 mg).

Reference Examples 33

Employing 3-chloro-2,4,5-trifluoro-6-methylbenzoyl chloride (183 mg), the procedure of Reference Example 18 is repeated to give diethyl 3-chloro-2,4,5-trifluoro-6-methylbenzoylmalonate (320 mg), as brown oil.

¹H-NMR (CDCl₃) δ ppm: 1.02, 1.29 and 1.38 (all 6H, each t, J=7 Hz), 2.27 (3H, d, J=1.5 Hz), 4.02, 4.21 and 4.39 (all 4H, each q, J=7 Hz), 3.36 and 13.7 (all 1H, each s)

Reference Examples 34

Employing diethyl 3-chloro-2,4,5-trifluoro-6-methylbenzoylmalonate (320 mg) and p-toluenesulfonic acid (3 mg), the procedure of Reference Example 19 is repeated to give ethyl 3-chloro-2,4,5-trifluoro-6-methylbenzoylacetate (300 mg), as brown oil.

¹H-NMR (CDCl₃) δ ppm: 1.25 and 1.35 (all 3H, each t, J=7 Hz), 2.32 (3H, m), 4.18 and 4.29 (all 2H, each q, J=7 Hz), 3.89, 5.25 and 12.35 (all 2H, each s)

Reference Example 35

Employing ethyl 3-chloro-2,4,5-trifluoro-6-methylbenzoylacetate (300 mg) and ethyl orthoformate (550 mg), the procedure of Reference Example 20 is repeated to give ethyl 2-(3-chloro-2,4,5-trifluoro-6-methylbenzoyl)-3-ethoxyacrylate (360 mg), as brown oil.

Reference Example 36

Employing ethyl 2-(3-chloro-2,4,5-trifluoro-6-methylbenzoyl)-3-ethoxyacrylate (360 mg) and cyclopropylamine (60 mg), the procedure of Reference Example 21 is repeated to give ethyl 2-(3-chloro-2,4,5-trifluoro-6-methylbenzoyl)-3-cyclopropylaminoacrylate (410 mg), as brown oil.

¹H-NMR (CDCl₃) δ ppm: 0.90 (4H, m), 1.04 (3H, t, J=7 Hz), 2.14 (3H, m), 3.01 (1H, m), 3.99 (2H, q, J=7 Hz), 8.29 (1H, d, J=14 Hz), 11.2 (1H, br)

Reference Examples 37

Employing ethyl 2-(3-chloro-2,4,5-trifluoro-6-methylbenzoyl)-3-cyclopropylaminoacrylate (410 mg) and 60% sodium hydride (35 mg), the procedure of Reference Example is repeated to give ethyl 1-cyclopropyl-6,7-difluoro-8-chloro-5-methyl-1,4-dihydro-4-oxoquinoline-3-carboxylate (70 mg), as pale yellow powder (recrystallized from dichloromethane-n-haxane), m.p. 153–154° C.

Reference Examples 38

Employing ethyl 1-cyclopropyl-6,7-difluoro-8-chloro-5-methyl-1,4-dihydro-4-oxoquinoline-3-carboxylate (70 mg) and conc. hydrochloric acid—90% acetic acid (1:4) (1 ml), the procedure of Reference Example 23 is repeated to give 1-cyclopropyl-8-chloro-6,7-difluoro-5-methyl-1,4-dihydro-4-oxoquinoline-3-carboxylate (58 mg), as white needles, m.p. 213°–215° C.

Reference Examples 39

Starting from suitable materials, the procedure of Reference Example 18 is repeated to give 2-ethyl-3,4,5,6-tetrafluorobenzoyl chloride, b.p. 78° C./14 mmHg.

¹H-NMR (CDCl₃) δ ppm: 1.24 (3H, t, J=7.5 Hz), 2.75 (2H, dq, J=2.3 Hz, 7.5 Hz)

Reference Examples 40

Starting from suitable materials, the procedure of Reference Example 18 is repeated to give diethyl 2-ethyl-3,4,5,6-tetrafluorobenzoylmalonate.

¹H-NMR (CDCl₃) δ ppm: 1.04 (3H, t, J=7.2 Hz), 1.19 (3H, t, J=7.4 Hz), 1.38 (3H, t, J=7.2 Hz), 2.5–2.8 (2H, m), 4.03 (2H, q, J=7 Hz), 4.39 (2H, q, J=7 Hz), 13.8 (1H, s)

Reference Example 41

Employing diethyl 2-ethyl-3,4,5,6-tetrafluoro-benzoylmalonate (17.2 g) and p-toluenesulfonic acid (0.25 g), the procedure of Reference Example 19 is repeated to give ethyl 2-ethyl-3,4,5,6-tetrafluorobenzoylacetate (11.09 g).

Reference Example 42

Employing ethyl 2-ethyl-3,4,5,6-tetrafluorobenzoylacetate (8 g) and ethyl orthoformate (6.1 g), the procedure of Reference Example 20 is repeated to give ethyl 2-(2-ethyl-3,4,5,6-tetrafluorobenzoyl)-3-ethoxyacrylate.

Reference Examples 43

Employing ethyl 2-(2-ethyl-3,4,5,6-tetrafluorobenzoyl)-3-ethoxyacrylate and cyclopropylamine, the procedure of Reference Example 21 is repeated to give ethyl 2-(2-ethyl-3,4,5,6-tetrafluorobenzoyl)-3-cyclopropylaminoacrylate.

Reference Examples 44

Employing ethyl 2-(2-ethyl-3,4,5,6-tetrafluorobenzoyl)-3-cyclopropylaminoacrylate (8.71 g) and 60% sodium hydride (1.09 g), the procedure of Reference Example 22 is repeated to give ethyl 1-cyclopropyl-6,7,8-trifluoro-5-ethyl-1,4-dihydro-4-oxoquinoline-3-carboxylate (5 g), as white powder, m.p. 139°14 140° C.

Reference Example 45

Employing ethyl 1-cyclopropyl-6,7,8-trifluoro-5-ethyl-1,4-dihydro-4-oxoquinoline-3-carboxylate (5 g), conc. hydrochloric acid (11 ml), water (4.4 ml) and acetic acid (44 ml), the procedure of Reference Example 23 is repeated to give 1-cyclopropyl-6,7,8-trifluoro-5-ethyl-1,4-dihydro-4-oxoquinoline-3-carboxylic acid (4.2 g), as white powder, m.p. 197°–198° C.

Reference Example 46

Employing ethyl 2-(2-methyl-3,4,5,6-tetrafluorobenzoyl)-3-ethoxyacrylate (10.0 g) and ethylamine gas, the procedure of Reference Example 21 is repeated to give ethyl 2-(2-methyl-3,4,5,6-tetrafluorobenzoyl)-3-ethylaminoacrylate (9.0 g, white crystals), which is then treated with 60% sodium hydride (1.30 g) as in Reference Example 22 to give ethyl 1-ethyl-5-methyl-6,7,8-trifluoro-1,4-dihydro-4-oxoquinoline-3-carboxylate (6.76 g), as pale yellow needles (recrystallized from dichloromethane - n-hexane), m.p. 197°–198° C.

Reference Example 47

Employing ethyl 1-ethyl-5-methyl-6,7,8-trifluoro-1,4-dihydro-4-oxoquinoline-3-caboxylate (6.51 g) and conc. hydrochloric acid: 90% acetic acid (1:4) (100 ml), the procedure of Reference Example 23 is repeated to give 1-ethyl-5-methyl-6,7,8-trifluoro-1,4-dihydro-4-oxoquinoline-3-carboxylic acid (5.53 g), as colorless needles (recrystallized from dichloromethane - n-hexane), m.p. 203°–204° C.

Reference Example 48

Employing ethyl 2-(2-methyl-3,4,5,6-tetrafluorobenzoyl)-3-ethoxyacrylate (5.0 g) and 2,4-difluoroaniline (2.02 g), the procedure of Reference Example 21 is repeated to give ethyl 2-(2-methyl-3,4,5,6-tetrafluorobenzoyl)-3-(2,4-difluorophenyl)aminoacrylate, which is then treated with 60% sodium hydride as in Reference Example 22 to give ethyl 1-(2,4-difluorophenyl)-5-methyl-6,7,8-trifluoro-1,4-dihydro-4-oxoquinoline-3-carboxylate (4.6 g), as pale yellow prisms (recrystallized from dichloromethane - n-hexane), m.p. 156°–157.5° C.

Reference Example 49

Employing ethyl 1-(2,4-difluorophenyl)-5-methyl-6,7,8-trifluoro-1,4-dihydro-4-oxoquinoline-3-caboxylate (4.3 g) and conc. hydrochloric acid: 90% acetic acid (1:4) (80 ml), the procedure of Reference Example 23 is repeated to give 1-(2,4-difluorophenyl)-5-methyl-6,7,8-trifluoro-1,4-dihydro-4-oxoquinoline-3-carboxylic acid (2.93 g), as white powder, m.p. 221°–222° C.

Reference Example 50

Employing ethyl 2-(2-methyl-3,4,5,6-tetrafluoro-benzoyl)-3-ethoxyacrylate (10.0 g) and 4-methoxyaniline (3.87 g), the procedure of Reference Example 21 is repeated to give ethyl 2-(2-methyl-3,4,5,6-tetrafluorobenzoil)-3-(4-methoxyphenyl)aminoacrylate, which is then ureated with 60% sodium hydride (1.56 g) as in Reference Example 22 to give ethyl 1-(4-methoxyphenyl)-5-methyl-6,7,8-trifluoro-1,4-dihydro-4-oxoquinoline-3-carboxylate (8.27 g), as pale yellow needles, m.p. 175°–176° C.

Reference Example 51

Employing ethyl 1-(4-methoxyphenyl)-5-6,7,8-trifluoro-1,4-dihydro-4-oxoquinoline-3-carboxylate (4.27 g) and 47% hydrobromic acid (50 ml), the procedure of Reference Example 23 is repeated to give 1-(4-hydroxyphenyl)-5-methyl-6,7,8-trifluoro-1,4-dihydro-4-oxoquinoline-3-carboxylic acid (2.82 g), as white powder, m.p. 287°–288.5° C.

Reference Example 52

Employing ethyl 2-(2-methyl-3,4,5,6-tetrafluorobenzoyl)3-ethoxyacrylate (5.0 g) and 2-aminothiophene (2.22 g), the procedure of Reference Example 21 is repeated to give ethyl 2-(2-methyl-3,4,5,6-tetrafluorobenzoyl)-3-(2-thienyl)aminoacrylate, which is then treated with 60% sodium hydride as in Reference Example 22 to give ethyl 1-(2-thienyl)-5-methyl-6,7,8-trifluoro-1,4-dihydro-4-oxoquinoline-3-carboxylate (1.05 g), as white powder (recrystallized from ethyl acetate - n-hexane), m.p. 198°–200° C.

Reference Examples 53

Employing ethyl 1-(2-thienyl)-5-methyl-6,7,8-trifluoro-1,4-dihydro-4-oxoquinoline-3-carboxylate (1.05 g), conc. hydrochloric acid (10 ml) and 90% acetic acid (40 ml), the procedure of Reference Example 23 is repeated to give 1-(2-thienyl)-5-methyl-6,7,8-trifluoro-1,4-dihydro-4-oxoquinoline-3-carboxylic acid (0.93 g), as white powder, m.p. 221°–222.5° C.

Reference Example 54

Employing ethyl 2-(2-methyl-3,4,5,6-tetrafluoro-benzoyl)-3-ethoxyacrylate (8.38 g) and 2S-2-amino-1-propanol (2.07 g), the procedure of Reference Example 21 is repeated to give ethyl 2-(2-methyl-3,4,5,6-tetrafluorobenzoyl)-3-(2S-3-hydroxy-2-propyl)aminoacrylate (9.72 g, yellow oil), which is then treated with potassium carbonate (4.25 g) as in Reference Example 22 to give ethyl 3S-9,10-difluoro-3,8-dimethyl-7-oxo-7H-pyrido[1,2,3-de][t,4]benzoxazine-6-carboxylate (1.30 g), as colorless needles (recrystallized from ethanol), m.p. 216°–217° C.

Reference Example 55

Employing ethyl 3S-9,10-difluoro-3,8-dimethyl-7-oxo-7H-pyrido[1,2,3-de][1,4]benzoxazine-6-carboxylate ( (1.25 g) and conc. hydrochloric acid: 90% acetic acid (1:4) (20 ml), the procedure of Reference Example 23 is repeated to give 3S (-) -9,10-difluoro-3,8-dimethyl-7-oxo-7H-pyrido[1,2,3-de] [1,4]benzoxazine-6-carboxylic acid (1.03 g), as white powder, m.p. 249°–251° C. (dec.).

Reference Example 56

Employing ethyl 2-(2-methyl-3,4,5,6-tetrafluorobenzoyl)-3-ethoxyacrylate (7.0 g) and ethanol amine (1.33 ml), the procedure of Reference Example 21 is repeated to give ethyl 2-(2-methyl-3,4,5,6-tetraflurobenzoyl)-3-(2-hydroxyethyl)aminoacrylate. To the product are added pyridine (70 ml) and acetic anhydride (2.57 ml) and the mixture is stirred at room temperature over-night. After concentration, the resultant is diluted with water, subjected to extraction with dichloromethane, and the extract is washed with water and then with a saturated saline solution and dried to give ethyl 2-(2-methyl-3,4,5,6-tetrafluorobenzoyl)-3-(2-acetyloxy-ethyl)aminoacrylate, which is then treated with 60% sodium hydride (1.09 g) as in Reference Example 22 to give ethyl 1-(2-acetyloxyethyl)-5-methyl-6,7,8-trifluoro-1,4-dihydro-4-oxoquinoline-3-carboxylate (6.15 g), as colorless prisms (recrystallized from ethyl acetate), m.p. 192°–193° C.

Reference Example 57

Employing ethyl 1-(2-acetyloxyethyl)-5-methyl-6,7,8-trifluoro-1,4-dihydro-4-oxoquinoline-3-carboxylate (5.80 g) and conc. hydrochloric acid: 90% acetic acid (1:4) (100 ml), the procedure of Reference Example 23 is repeated to give 1-(2-hydroxyethyl)-5-methyl-6,7,8-trifluoro-1,4-dihydro-4-oxoquinoline-3-carboxylic acid (4.04 g), as pale yellow flakes (recrystallized from ethanol), m.p. 244.5°–247° C.

Reference Example 58

To 1-(2-hydroxyethyl)-5-methyl-6,7,8-trifluoro-1,4-dihydro-4-oxoquinoline-3-carboxylic acid (4.00 g) is added thionyl chloride (20 ml) and the mixture is refluxed for 1 hour. After concentrating, the obtained residue is mixed with ethanol (50 ml) and the mixture is refluxed for 1 hour. After concentrating, the resultant is extracted with dichloromethane, and the extract is washed with water, saturated sodium hydrogen carbonate, water and saturated saline solution in this order and dried. The solvent is concentrated and the obtained residue is purified by silica-gel column-chromatography (eluent; ethyl acetate: n-hexane =1:20), followed by recrystllization from ethyl acetate-n-hexane to give ethyl 1-(2-chloroethyl)-5-methyl-6,7,8-trifluoro-1,4-dihydro-4-oxoquinoline-3-carboxylic acid (2.00 g), as colorless prisms, m.p. 161.5°–163.5° C. (dec.).

Reference Example 59

To ethyl 1-(2-chloroethyl)-5-methyl-6,7,8-trifluoro-1,4-dihydro-4-oxoquinoline-caboxylate (1.81 g) are added DBU (2.33 ml) and toluene (150 ml) and the mixture is refluxed with heating for 4 hours. After concentrating, the obtained residue is extracted with dichloroethane, and the extract is washed with dilute hydrochloric acid, water and saturated saline solution in this order and dried. The solvent is concentrated and the obtained residue is purified by silica-gel column-chromatography (eluent; ethyl acetate: n-hexane =1:20), followed by recrystallization from n-hexane-diethyl ether to give ethyl 1-vinyl-5-methyl-6,7,8-trifluoro-1,4-dihydro-4-oxoquinoline-3-caboxylate (0.72 g), as colorless needles, m.p. 134°–135.5° C.

Reference Example 60

Employing ethyl 2-(2-methyl-3,4,5,6-tetrafluorobenzoyl)-3-ethoxyacrylate (5.0 g), 2-chloroethylamine hydrochloride (1.74 g) and triethylamine (1.97 g), the procedure of Reference Example 21 is repeated to give ethyl 2-(2-methyl-3,4,5,6-tetrafluorobenzoyl)-3-(2-chloroethyl) aminoacrylate (5.52 g), which is then treated with 60% sodium hydride (0.72 g) as in Reference Example 22 to give ethyl 1-(2-chloroethyl)-5-methyl-6,7,8-trifluoro-1,4-dihydro-4-oxoquinoline-3-carboxylate (3.90 g), as colorless needles (recrystallized from ethyl acetate - n-hexane), m.p. 161.5°–163.5° C. (dec.)

Example 1

To 3-(4-methyl-1-piperazinyl)-4-fluoro-2,5-dimethyl-6-nitro-N-cyclopropylaniline (1.65 g) is added diethyl ethoxymethylenemalonate (1.45 ml) and the mixture is heated at 150° C. for 25 hours. After cooling, the reaction product is purified by silica-gel column-chromatography (dichloromethane: methanol =100:1) to give diethyl[N-cyclopropyl-N-[3-(4-methyl-11-piperazinyl)-4-fluoro-2,5-dimethyl-6-nitrophenyl]aminomethylene]malonate (1.58 g). The product is dissolved in acetic anhydride (7.9 ml) and thereto conc. sulfuric acid (3.16 ml) is added dropwise at 50°–60° C., followed by stirring for 30 minutes. The resultant mixture is poured into ice-water, neutralized, extracted with dichloromethane and the extract is dried. The solvent is distilled off under reduced pressure. Purification by silica-gel column-chromatography (dichloromethane: methanol =10:1) and recrystallization from ethanol—diethyl ether to give ethyl 7-(4-methyl-1-piperazinyl)-1-cyclopropyl-6-fluoro-5, 8-dimethyl-1,4-dihydro-4-oxoquinoline-3-carboxylate (28 mg), as yellow crystals, m.p. 146°–147° C.

$^1$H NMR (CDCl$_3$) δ0.7–0.8 (2H, m), 1.0–1.2 (2H, m), 1.39 (3H, t, J=7 Hz), 2.39 (3H, s), 2.59 (3H ,s), 2.4–2.7 (4H, br), 2.75 (3H, d, J=2.9 Hz), 3.1–3.4 (4H, br), 3.8–4.0 (1H, m), 4.38 (2H, q, J=7.1 Hz), 8.54 (1H, s)

Example 2

To ethyl 7-(4-methyl-1-piperazinyl)-1-cyclopropyl-6-fluoro-5, 8-dimethyl-1,4-dihydro-4-oxoquinoline-3-carboxylate (25 mg) are added 10% aqueous solution of sodium hydroxide (3 ml) and ethanol (3 ml), and the mixture is refluxed for 1 hour. After cooling, the reaction mixture is diluted with water and washed with dichloromethane. The aqueous layer is made acidic with acetic acid and then made weak alkaline with an aqueous sodium hydrogen carbonate. The resultant is extracted with dichloromethane and the extract is dried. The solvent is distilled off under reduced pressure and to the residue is added diethyl ether. The precipitated crystals are filtered and recrystallized from ethanol to give 7-(4-methyl-1-piperazinyl)-1-cyclopropyl-6-fluoro-5, 8-dimethyl-1,4-dihydro-4-oxoquinoline-3-carboxylic acid (14 mg), as yellow crystals, m.p. 205°–206° C.

$^1$H NMR (CDCl$_3$) δ0.7°–0.9 (2H, m), 1.1°–1.4 (2H, m), 2.39 (3H, s), 2.5–2.8 (4H, br), 2.63 (3H, s), 2.76 (3H, d, J=3 Hz), 3.2–3.5 (4H, br), 4.0–4.2 (1H, m), 8.85 (1H, s), 4.3–14.9 (1H, br)

Example 3

To 6,7-difluoro-1-cyclopropyl-5,8-dimethyl-1,4-difluoro-4-oxoquinoline-3-carboxylic acid - B(OCOCH$_3$)$_2$ chelate (1.24 g) are added 4-methyl-l-piperazine (1.0 g) and dimethylacetamide (6 ml), and the mixture is reacted at 50° C. for 20 hours. After concentrating, the obtained residue is dissolved in acetone (20 ml) and thereto conc. hydrochloric acid (5 ml) is added, followed by stirring at room temperature for 30 minutes. The solvent is distilled off and the resultant residue is treated with water and extracted with dichloromethane. The aqueous layer is neutralized with an aqueous sodium hydrogen carbonate and extracted with dichloromethane. After drying over magnesium sulfate, the residue is added with a mixture of diethyl ether and ethanol. The precipitated crystals are filtered and recrystallized from ethanol to give 7-(4-methyl-1-piperazinyl)-1-cyclopropyl-6-fluoro-5, 8-dimethyl-1,4-dihydro-4-oxoquinoline-3-carboxylic acid (0.1 g), as yellow crystals, m.p. 205°–206° C.

Example 4

To a suspension of 6,7-difluoro-1-cyclopropyl-5,8-dimethyl-1,4-dihydro-4-oxoquinoline-3-carboxylic acid (1.88 g) in N-methylpyrrolidone (5 ml) is added 4-methyl-1-piperazine (2.02 g) and the mixture is stirred at 150° C. for 3 hours. After the reaction is completed, the reaction mixture is concentrated and the obtained residue is purified by silica-gel column-chromatography (dichloromethane: methanol=3:1), followed by recrystallization from ethanol to give 7-(4-methyl-1-piperazinyl)-1-cyclopropyl-6-fluoro-5, 8-dimethyl-1,4-dihydro-4-oxoquinoline-3-carboxylic acid (0.05 g), as yellow crystals, m.p. 205°–206° C.

Example 5

Starting from suitable materials, the procedure of the above Examples 1–4 is repeated to give the following compounds.

1) 7-(1-Piprazinyl)-1-cyclopropyl-6-fluoro-5,8-dimethyl-1,4-dihydro-4-oxoquinoline-3-carboxylic acid, m.p. 185°–187° C., pale yellow needles (recrystallized from dimethylformamide)

2) 7-(3-Methyl-1-piperazinyl)-1-cyclopropyl-6-fluoro-5,-dimethyl-1, 4-dihydro-4-oxoquinoline-3-carboxylic acid, m.p. 183°–185° C. colorless powder 3) 7-(3-Amino-1-pyrrolidinyl)-1-cyclopropyl-6-fluoro-5, 8-dimethyl-1, 4-dihydro-4-oxoquinoline-3-carboxylic acid, m.p. 96°–98° C., pale yellow needles 4) 7-(1-Piperazinyl)-1-cyclopropyl-6,8-difluoro-5-methyl-1,4-dihydro-4-oxoquinoline-3-carboxylic acid, m.p. 205°–207°C., white powder (recrystallized from ethanol)

5) 7-(4-Methyl-1-piperazinyl)-1-cyclopropyl-6, 8-difluoro-5-methyl-1,4-dihydro-4-oxoquinoline-3-carboxylic acid, m.p. 229°–231° C., white needles (recrystallized from ethanol)

6) 7-(3-Methyl-1-piperazinyl)-1-cyclopropyl-6, 8-difluoro-5-methyl-1,4-dihydro-4-oxoquinoline-3-carboxylic acid, m.p. 188°–189° C., pale yellow powder (recrystallized from ethanol)

7) 7-(3-Amino-1-pyrrolidinyl)-1-cyclopropyl-6, 8-difluoro-5-methyl-1,4-dihydro-4-oxoquinoline-3-carboxylic acid, m.p. 213°–216° C., pale yellow powder (recrystallized from dimethylformamide)

8) 7-(1-Piperazinyl)-1-cyclopropyl-6-fluoro-8-chloro-5-methyl-1, 4-dihydro-4-oxoquinoline-3-carboxylic acid, m.p. 214°–217° C., pale yellow powder (recrystallized from ethanol)

9) 7-(4-Methyl-1-piperazinyl)-1-cyclopropyl-6-fluoro-8-chloro-5-methyl-1, 4-dihydro-4-oxoquinoline-3-carboxylic acid, m.p. 190°–192°C., pale yellow powder (recrystallized from dichloromethane - n-hexane)

10) 7-(3-Methyl-1-piperazinyl)-1-cyclopropyl-6-fluoro-8-chloro-5-methyl-1, 4-dihydro-4-oxoquinoline-3-carboxylic acid 11) 7-(3-Amino-1-piperazinyl)-1-cyclopropyl-6-fluoro-8-chloro-5-methyl-1, 4-dihydro-4-oxoquinoline-3-carboxylic acid 12) 7-(1-Piperazinyl)-1-cyclopropyl-5, 6-difluoro-8-methyl-1,4-dihydro-4-oxoquinoline-3-carboxylic acid 13) 7-(4-Methyl-1-piperazinyl)-1-cyclopropyl-5, 6-difluoro-8-methyl-1,4-dihydro-4-oxoquinoline-3-carboxylic acid 14) 7-(3-Methyl-1-piperazinyl)-1-cyclopropyl-5, 6-difluoro-8-methyl-1,4-dihydro-4-oxoquinoline-3-carboxylic acid 15) 7-(3-Amino-1-pyrrolidinyl)-1-cyclopropyl-5, 6-difluoro-8-methyl-1,4-dihydro-4-oxoquinoline-3-carboxylic acid 16) 7-(1-Piperazinyl )-1-cyclopropyl-5-chloro-6-fluoro-8-methyl-1,4-dihydro-4-oxoquinoline-3-carboxylic acid 17) 7-(4-Methyl-1-piperazinyl)-1-cyclopropyl-5-chloro-6-fluoro-8-methyl-1, 4-dihydro-4-oxoquinoline-3-carboxylic acid, m.p. 213°–215° C., yellow crystals 18) 7-(3-Methyl-1-piperazinyl)-1-cyclopropyl-5-chloro-6-fluoro-8-methyl-1, 4-dihydro-4-oxoquinoline-3-carboxylic acid 19) 7-(3-Amino-1-pyrrolidinyl)-1-cyclopropyl-5-chloro-6-fluoro-8-methyl-1, 4-dihydro-4-oxoquinoline-3-carboxylic acid 20) 7-(4-Benzyl-1-piperazinyl)-1-cyclopropyl-6-fluoro-5, 8-dimethyl-1,4-dihydro-4-oxoquinoline-3-carboxylic acid, m.p. 165°–166° C., pale yellow needles (recrystallized from diethyl ether - ethanol)

21) 7-(4-Benzyl-3-methyl-1-piperazinyl)-1-cyclo-propyl-6-fluoro-5, 8-dimethyl-1,4-dihydro-4-oxoquinoline-3-carboxylic acid, m.p. 176°–178° C., pale yellow powder 22) 7-(1,4-Diazabicyclo[4,3,0]nonan-4-yl)-1-cyclopropyl-6, 8-difluoro-5-methyl-1,4-dihydro-4-oxoquinoline-3-carboxylic acid, m.p. 194°–197° C., pale yellow needles (recrystallized from dichlomethane - n-hexane)

23) 7-Morpholino-1-cyclopropyl-6,8-difluoro-5-methyl-1,4-dihydro-4-oxoquinoline-3-carboxylic acid, m.p. 255°–259° C., white needles (recrystallized from ethanol)

24) 7-(4-Hydroxy-1-piperidinyl)-1-cyclopropyl-6, 8-difluoro-5-methyl-1,4-dihydro-4-oxoquinoline-3-carboxylic acid, m.p. 247°–250° C., white needles (recrystallized from ethanol)

25) 7-(4-Fluoro-1-piperidinyl)-1-cyclopropyl-6, 8-difluoro-5-methyl-1,4-dihydro-4-oxoquinoline-3-carboxylic acid, m.p. 259°–261° C., pale yellow needles (recrystallized from ethanol)

26) 7-(3-Methylamino-1-pyrrolidinyl)-1-cyclopropyl-6, 8-difluoro-5-methyl-1,4-dihydro-4-oxoquinoline-3-carboxylic acid monohydrochloride, m.p. 215°–219° C., white powder (recrystallized from ethanol)

27) 7-(3-Ethylaminomethyl-1-pyrrolidinyl)-1-cyclopropyl-6, 8-difluoro-5-methyl-1,4-dihydro-4-oxoquinoline-3-carboxylic acid monohydrochloride, m.p. 221°–223° C., white powder (recrystallized from ethanol)

28) 7-(3-Aminomethyl-1-pyrrolidinyl)-1-cyclopropyl-6, 8-difluoro-5-methyl-1,4-dihydro-4-oxoquinoline-3-carboxylic acid 29) 7-(3-Amino-4-methyl-1-pyrrolidinyl)-1-cyclopropyl-6, 8-difluoro-5-methyl-1,4-dihydro-4-oxoquinoline-3-carboxylic acid monohydrochloride (cis form), m.p. 209°–213° C., pale yellow powder (recrystallized from ethanol)

30) 7-(3-Amino-4-methyl-1-pyrrolidinyl)-1-cyclopropyl-6, 8-difluoro-5-methyl-1,4-dihydro-4-oxoquinoline-3-carboxylic acid monohydrochloride (trans form), m.p. 214°–216° C. pale yellow powder (recrystallized from ethanol)

31) 7-[4-(5-Methyl-2-oxo-1, 3-dioxolen-4-yl)-methyl-1-piperazinyl]-1-cyclopropyl-6, 8-difluoro-5-methyl-1,4-dihydro-4-oxoquinoline-3-carboxylic acid 32) 7-(4-Acetyl-1-piperazinyl)-1-cyclopropyl-6, 8-difluoro-5-methyl-1,4-dihydro-4-oxoquinoline-3-carboxylic acid, m.p. 217°–220° C., white powder (recrystallized from ethanol)

33) 7-[3-(N-t-Butoxycarbonyl-N-methylamino)-1-pyrrolidinyl]-1-cyclopropyl-6, 8-difluoro-5-methyl-1, 4-dihydro-4-oxoquinoline-3-carboxylic acid, m.p. 184°–187°C., white powder (recrystallized from ethanol)

34) 7-[3-(N-t-Butoxycarbonyl-N-ethylaminomethyl)-1-pyrrolidinyl]-1-cyclopropyl-6, 8-difluoro-5-methyl-1,4-dihydro-4-oxoquinoline-3-carboxylic acid, m.p. 147°–149° C., white powder (recrystallized from ethanol)

35) 7-[3-(N-t-Butoxycarbonylaminomethyl)-1-pyrrolidinyl]-1-cyclopropyl-6, 8-difluoro-5-methyl-1,4-dihydro-4-oxoquinoline-3-carboxylic acid 36) 7-(3-t-Butoxycarbonylamino-4-methyl-1-pyrrolidinyl)- 1-cyclopropyl-6, 8-difluoro-5-methyl-1,4-dihydro-4-oxoquinoline-3-carboxylic acid (cis form), m.p. 215°–217° C., pale yellow powder (recrystallized from ethanol)

37) 7-(3-t-Butoxycarbonylamino-4-methyl-1-pyrrolidinyl)-1-cyclopropyl-6, 8-difluoro-5-methyl-1,4-dihydro-4-oxoquinoline-3-carboxylic acid (trans form), m.p. 23°–224° C., white powder (recrystallized from ethanol)

38) 7-(3-Amino-1-pyrrolidinyl)-1-cyclopropyl-6-fluoro-8-chloro-5-methyl-1, 4-dihydro-4-oxoquinoline-3-carboxylic acid, m.p. 194°–195° C., pale yellow powder (recrystallized from ethanol)

39) 7-(1-Piperazinyl)-1-(2,4-difluorophenyl)-6, 8-difluoro-5-methyl-1,4-dihydro-4-oxoquinoline-3-carboxylic acid, m.p. 244°–246° C.(dec.), white powder (recrystallized from dimethylformamide)

40) 7-(4-Methyl-1-piperazinyl)-1-(2,4-difluoro-phenyl)-6, 8-difluoro-5-methyl-1,4-dihydroxy-4-oxoquinoline-3-carboxylic acid, m.p. 228°–230° C. (dec.), white powder (recrystallized from ethanol)

41) 7-(1-Piperazinyl)-1-(4-hydroxyphenyl)-6, 8-difluoro-5-methyl-1,4-dihydroxy-4-oxoquinoline-3-carboxylic acid, m.p. >300° C., white powder 42) 7-(4-Methyl-1-piperazinyl)-1-(4-hydroxyphenyl)-6, 8-difluoro-5-methyl-1,4-dihydro-4-oxoquinoline-3-carboxylic acid, m.p. >300° C., white powder 43) 7-(1-Piperazinyl)-1-ethyl-6, 8-difluoro-5-methyl-1,4-dihydro-4-oxoquinoline-3-carboxylic acid, m.p. 219°–220° C. (dec.), colorless needles (recrystallized from ethanol)

44) 7-(4-Methyl-1-piperazinyl)-1-ethyl-6, 8-difluoro-5-methyl-1,4-dihydro-4-oxoquinoline-3-carboxylic acid, m.p. 212.5°–215° C. (dec.), pale yellow prisms (recrystallized from ethanol)

45) 7-(3-Methyl-1-piperazinyl)-1-ethyl-6, 8-difluoro-5-methyl-1,4-dihydro-4-oxoquinoline-3-carboxylic acid, m.p. 209.5°–211° C. (dec.), white powder (recrystallized from ethanol)

46) Ethyl 7-(1-piperazinyl)-1-vinyl-6, 8-difluoro-5-methyl-1,4-dihydro-4-oxoquinoline-3-carboxylate, m.p. 181°–183° C. (dec.), pale yellow needles (recrystallized from chloroform - n-hexane)

47) Ethyl 7-(4-methyl-1-piperazinyl)-1-vinyl-6, 8-difluoro-5-methyl-1,4-difluoro-4-oxoquinoline-3-carboxylate, m.p. 165°–166° C. (dec.), pale yellow needles (recrystalized from ethyl acetate - n-hexane)

48) 7-(1-Piperazinyl)-1-vinyl-6, 8-difluoro-5-methyl-1,4-dihydro-4-oxoquinoline-3-carboxylic acid, m.p. 205°–206.5° C. (dec.), pale yellow powder 49) 7-(4-Methyl-1-piperazinyl)-1-vinyl-6, 8-difluoro-5-methyl-1,4-dihydro-4-oxoquinoline-3-carboxylic acid, m.p. 187.5°–189.5° C. (dec.), pale yellow needles (recrystallized from ethyl acetate - n-hexane)

50) 7-(1-Piperazinyl)-1-(2-thienyl)-6, 8-difluoro-5-methyl-1,4-dihydro-4-oxoquinoline-3-carboxylic acid, m.p. 239°–240.5° C. (dec.), white powder (recrystallized from ethanol)

51) 7-(1-Piperazinyl)-1-cyclopropyl-6, 8-difluoro-5-ethyl-1,4-dihydro-4-oxoquinoline-3-carboxylic acid, m.p. 161°–163° C., yellow powder (recrystallized from dimethylformamide)

52) 7-(3-Methyl-1-piperazinyl)-1-cyclopropyl-6, 8-difluoro-5-ethyl-1,4-dihydro-4-oxoquinoline-3-carboxylic acid, m.p. 146°–147° C., white powder (recrystallized from dimethylformamide-ethanol-diethyl ether)

53) 7-(4-Methyl-1-piperazinyl)-1-cyclopropyl-6, 8-difluoro-5-ethyl-1,4-dihydro-4-oxoquinoline-3-carboxylic acid, m.p. 201°–202° C., white powder (recrystallized from dimethylformamide)

54) 7-(3-Amino-1-pyrrolidinyl)-1-cyclopropyl-6, 8-difluoro-5-ethyl-1,4-dihydro-4-oxoquinoline-3-carboxylic acid, m.p. 164°–165° C., white powder (recrystallized from ethanol)

55) 3S(-)-10-(4-Methyl-1-piperazinyl)-9-fluoro-3, 8-dimethyl-7-oxo-7H-pyrido[1,2,3-de][1,4]benzoxazine-6-carboxylic acid, m.p. 235°–236.5° C. (dec.), colorless prisms (recrystallized from ethanol), $[\alpha]^{25}_D = -125.9°$ C. (C=0.21, chloroform)

Example 6

A mixture comprising 7-(3-t-butoxycarbonylamino-4-methyl-1-pyrrolidinyl)-1-cyclopropyl-6, 8-difluoro-5-methyl-1,4-dihydro-4-oxoquinoline-3-carboxylic acid (trans form) (125 mg), ethanol (4 ml) and 10% hydrochloric acid (4 ml) is refluxed for 30 minutes. After concentrating, the obtained residue is recrystallized from ethanol to give 7-(3-amino-4-methyl-1-pyrrolidinyl)-1-cyclopropyl-6, 8-difluoro-5-methyl-1,4-dihydro-4-oxoquinoline-3-carboxylic acid monohydrochloride (trans form) (63 mg), as pale yellow powder, m.p. 214°–216° C.

Starting from suitable materials, the procedure of Example 6 is repeated to give the following compounds.

1) 7-(3-Methylamino-1-pyrrolidinyl)-1-cyclopropyl-6, 8-difluoro-5-methyl-1,4-dihydro-4-oxoquinoline-3-carboxylic acid monohydrochloride, m.p. 215°–219° C., white powder (recrystallized from ethanol)

2) 7-(3-Ethylaminomethyl-1-pyrrolidinyl)-1-cyclopropyl-6, 8-difluoro-5-methyl-1,4-dihydro-4-oxoquinoline-3-carboxylic acid monohydrochloride, m.p. 221°–223° C., white powder (recrystallized from ethanol)

3) 7-(3-Aminomethyl-1-pyrrolidinyl)-1-cyclopropyl-6, 8-difluoro-5-methyl-1,4-dihydro-4-oxoquinoline-3-carboxylic acid 4) 7-(3-Amino-4-methyl-1-pyrrolidinyl)-1-cyclopropyl-6, 8-difluoro-5-methyl-1,4-dihydro-4-oxoquinoline-3-carboxylic acid monohydrochloride (cis form), m.p. 209°–213° C., pale yellow powder (recrystallized from ethanol)

5) 7-(3-Amino-1-pyrrolidinyl)-1-cyclopropyl-6, 8-difluoro-5-ethyl-1,4-dihydro-4-oxoquinoline-3-carboxylic acid, m.p. 164°–165° C., white powder (recrystallized from ethanol)

Example 7

To a solution of 7-(1-piperazinyl)-1-cyclopropyl-6, 8-difluoro-5-methyl-1,4-dihydro-4-oxoquinoline-3-carboxylic acid (42 mg) in 5% sodium hydroxide (2 ml) is added acetic anhydride (0.1 ml) at room temperature. After the mixture is made acidic with dilute hydrochloric acid, the resultant is extracted with dichloromethane and the extract is dried over magnesium sulfate. After concentrating, the obtained residue is recrystallized from ethanol to give 7-(4-acetyl-1-piperazinyl)-1-cyclopropyl-6, 8-difluoro-5-methyl-1,4-dihydro-4-oxoquinoline-3-carboxylic acid (30 mg), as white powder, m.p. 217°–220° C.

Example 8

To a solution of 7-(4-benzyl-1-piperazinyl)-1-cyclopropyl-6-fluoro-5,8-dimethyl-1, 4-dihydro-4-oxo-quinoline-3-carboxylic acid (150 mg) in ethanol (20 ml) is added 10% Pd-C (50 mg) and the catalytic reduction is carried out at 70° C. under atomospheric pressure. After filtering off the 10% Pd-C, the filtrate is concentrated. The residue is recrystalized from dimethylformamide to give 7-(1-piperazinyl)-1-cyclopropyl-6-fluoro-5,8-dimethyl-1, 4-dihydro-4-oxo-quinoline-3-carboxylic acid (64 mg), m.p. 185°–187° C., as pale yellow needles.

Starting from suitable materials, the procedure of Example 8 is repeated to give 7-(3-methyl-1-piperazinyl)-1-cyclopropyl-6-fluoro-5, 8-dimethyl-1,4-dihydro-4-oxoquinoline-3-carboxylic acid.

EXAMPLE 9

The procedures of Example 1 are repeated, via diethyl [N-cyclopropyl-N-[3-(3-ethoxycarbonylamino-1-pyrrolidinyl)-4-fluoro-2, 5-dimethyl-6-nitrophenyl]aminomethylene] malonate as an intermediate compound, to give ethyl 7-(3-ethoxycarbonylamino-1-pyrrolidinyl)-1-cyclopropyl-6-fluoro-5, 8-dimethyl-1,4-dihydro-4-oxoquinoline-3-carboxylate.

$^1$H-NMR (CDC13) δppm: 0.7–0.9 (2H, m), 1.0-1.2 (2H, m), 1.39 (3H, t, J=7.1 Hz), 1.40 (3H, t, J=7.1 Hz), 2.1–2.4 (2H, m), 2.50 (3H, s), 2.75 (3H, d, J=3 Hz), 3.4–3.7 (4H, m), 3.8–4.0 (1H, m), 4.1–4.5 (5H, m), 5.3–5.5 (1H, m), 8.54 (1H, s)

Example 10

The procedure of Example 1 is repeated, via diethyl [N-cyclopropyl-N-[3-(4-benzyl-1-piperazinyl)-4-fluoro-2, 5-dimethyl-6-nitrophenyl]aminomethylene]malonate as an intermediate compound, to give ethyl 7-(4-benzyl-1-piperazinyl)-1-cyclopropyl-6-fluoro-5,8-dimethyl-1, 4-dihydro-4-oxoquinoline-3-carboxylate.

$^1$H-NMR (CDC13) 6ppm: 0.6–0.8 (2H, m), 1.0–1.2 (2H, m), 1.39 (3H, t, J=7.1 Hz), 2.58 (3H, s),-2.4–2.7 (4H, br), 2.74 (3H, d, J=3.0 Hz), 3.1–3.4 (4H, br), 3.60 (2H, s), 3.8–4.0 (1H, m), 4.38 (2H, q, J=7.1 Hz), 7.3–7.4 (5H, m), 8.53 (1H, s)

Example 11

The procedure of Example 1 is repeated, via [N-cyclopropyl-N-[3-(4-benzyl-3-methyl-1-piperazinyl)-4-fluoro-2, 5-dimethyl-6-nitrophenyl]aminomethylene]malonate as an intermediate compound, to give ethyl 7-(4-benzyl-3-methyl-1-piperazinyl)-1-cyclopropyl-6-fluoro-5,8-dimethyl-1, 4-dihydro-4-oxoquinoline-3-carboxylate, m.p. 128°–129° C., as pale yellow powder.

Example 12

To ethyl 7-(3-ethoxycarbonylamino-1-pyrrolidinyl)-cyclopropyl-6-fluoro-5,8-dimethyl-1, 4-dihydro-4-oxoquinoline-3-carboxylate (130 mg) is added 5% aqueous potassium hydroxide solution (3.2 ml) and the mixture is refluxed for 4 hours. After cooling, the reaction mixture is made acidic with acetic acid and then made weak alkaline with potassium carbonate. The resultant is extracted with dichloroethane and the extract is dried, followed by distillating the solvent under reduced pressure. To the residue is added diethyl ether and the precipitated crystals are filtered to give 7-(3-amino-1-pyrrolidinyl)-1-cyclopropyl-6-fluoro-5, 8-dimethyl-l,4-dihydro-4-oxoquinoline-3-carboxylic acid (30 mg), m.p. 96°–98° C., as pale yellow needles.

Example 13

The procedure of Example 1 is repeated, via diethyl [N-cyclopropyl-N-[3-(4-methyl-1-piperazinyl)-4-fluoro-2-methyl-5-chloro-6-nitrophenyl]aminomethylene]-malonate as an intermediate compound, to give ethyl 7-(4-methyl-1-piperazinyl)-1-cyclopropyl-6-fluoro-5-chloro-8-methyl-1, 4-dihydro-4-oxoquinoline-3-carboxylate, m.p. 175°–177° C., as yellow crystals.

Experiment (Antimicrobial activity in vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of 1×10$^6$ cells/ml (O.D. 660 mµ, 0.07–0.16, 100 folds dilution). The results are shown in Table 1.

[Test compounds]:

1. 7-(4-Methyl-1-piperazinyl)-1-cyclopropyl-6-fluoro-5, 8-dimethyl-1,4-dihydro-4-oxoquinoline-3-carboxylic acid 2. 7-(1-Piperazinyl)-1-cyclopropyl-6-fluoro-5, 8-dimethyl-1,4-dihydro-4-oxoquinoline-3-carboxylic acid 3. 7-(3-Amino-1-pyrrolidinyl)-1-cyclopropyl-6-fluoro-5, 8-dimethyl-1,4-dihydro-4-oxoquinoline-3-carboxylic acid 4. 7-(3-Methyl-1-piperazinyl)-1-cyclopropyl-6-fluoro-5, 8-dimethyl-1,4-dihydro-4-oxoquinoline-3-carboxylic acid 5. 7-(1-Piperazinyl)-1-cyclopropyl-6,8-difluoromethyl-1, 4-dihydro-4-oxoquinoline-3-carboxylic acid 6. 7-(4-Methyl-1-piperazinyl)-1-cyclopropyl-6, 8-difluoro-5-methyl-1,4-dihydro-4-oxoquinoline-3-carboxylic acid 7. 7-(3-Methyl-l-piperazinyl)-1-cyclopropyl-6, 8-difluoro-5-methyl-1,4-dihydro-4-oxoquinoline-3-carboxylic acid 8. 7-(3-Amino-1-pyrrolidinyl)-1-cyclopropyl-6, 8-difluoro-5-methyl-1,4-dihydro-4-oxoquinoline-3-carboxylic acid 9. 7-(4-Methyl-1-piperazinyl)-1-cyclopropyl-5-chloro-6-fluoro-8-methyl-1, 4-dihydro-4-oxoquinoline-3-carboxylic acid 10. 7-(1,4-Diazabicyclo[4,3,0]nonan-4-yl)-1-cyclopropyl-6, 8-difluoro-5-methyl-1,4-dihydro-4-oxoquinoline-3-carboxylic acid.

11. 7-Morpholino-1-cyclopropyl-6, 8-difluoro-5-methyl-1,4-dihydro-4-oxoquinoline-3-carboxylic acid 12. 7-(4-Hydroxy-1-piperizinyl)-1-cyclopropyl-6, 8-difluoro-5-methyl-1,4-dihydro-4-oxoquinoline-3-carboxylic acid 13. 7-(4-Fluoro-l-piperidinyl)-1-cyclopropyl-6, 8-difluoro-5-methyl-1,4-dihydro-4-oxoquinoline-3-carboxylic acid 14. 7-(3-t-Butoxycarbonylamino-4-methyl-1-pyrrolidinyl)-1-cyclopropyl-6, 8-difluoro-5-methyl-1,4-dihydro-4-oxoquinoline-3-carboxylic acid (trans form)

15. 7-(3-Methylamino-1-pyrrolidinyl)-1-cyclopropyl-6, 8-difluoro-5-methyl-1,4-dihydro-4-oxoquinoline-3-carboxylic acid monohydrochloride 16. 7-(3-Ethylaminomethyl-1-pyrrolidinyl)-1-cyclopropyl-6, 8-difluoro-5-methyl-1,4-dihydro-4-oxoquinoline-3-carboxylic acid monohydrochloride 17. 7-(3-Amino-4-methyl-1-pyrrolidinyl)-1-cyclopropyl-6, 8-difluoro-5-methyl-1,4-dihydro-4-oxoquinoline-3-carboxylic acid monohydrochloride (trans form)

18. 7-(3-Amino-4-methyl-1-pyrrolidinyl)-1-cyclopropyl-6, 8-difluoro-5-methyl-1,4-dihydro-4-oxoquinoline-3-carboxylic acid monohydrochloride (cis form)

19. 7-(4-Acetyl-l-piperazinyl)-1-cyclopropyl-6, 8-difluoro-5-methyl-1,4-dihydro-4-oxoquinoline-3-carboxylic acid 20. 7-(4-Methyl-1-piperazinyl)-1-cyclopropyl-6-fluoro-8-chloro-5-methyl-1, 4-dihydro-4-oxoquinoline-3-carboxylic acid 21. 7-(1-Piperazinyl)-1-cyclopropyl-6-fluoro-8-chloro-5-methyl-1, 4-dihydro-4-oxoquinoline-3-carboxylic acid 22. 7-(3-Amino-1-pyrrolidinyl)-1-cyclopropyl-6-fluoro-8-chloro-5-methyl-1, 4-dihydro-4-oxoquinoline-3-carboxylic acid 23. 7-(1-piperazinyl)-1-(2,4-difluorophenyl)-6, 8-difluoro-5-methyl-1,4-dihydro-4-oxoquinoline-3-carboxylic acid 24. 7-(4-Methyl-l-piperazinyl)-1-(2,4-difluorophenyl)-6, 8-difluoro-5-methyl-1,4-dihydro-4-oxoquinoline-3-carboxylic acid 25. 7-(1-piperazinyl)-1-(4-hydroxyphenyl)-6, 8-difluoro-5-methyl-1,4-dihydro-4-oxoquinoline-3-carboxylic acid 26. 7-(4-Methyl-l-piperazinyl)-1-(4-hydroxyphenyl)-6, 8-difluoro-5-methyl-1,4-dihydro-4-oxoquinoline-3-carboxylic acid 27. 7-(1-piperazinyl)-1-ethyl-6,8-difluoro-5-methyl-1, 4-dihydro-4-oxoquinoline-3-carboxylic acid 28. 7-(1-piperazinyl)-1-vinyl-6,8-difluoro-5-methyl-1,4-dihydro-4-oxoquinoline-3-carboxylic acid 29. 3S (-)-10-(4-Methyl-1-piperazinyl)-9-fluoro-3, 8-dimethyl-7-oxo-7H-pyrido[1,2,3-de][1,4]benzoxazine-6-carboxylic acid

[Test microorganisms]:

A: Staphylococcus aureus FDA 209P

B: Staphylococcus aeruginosa E-2

TABLE 1

| Test compounds | Microorganisms | |
| | A | B |
| --- | --- | --- |
| 1 | 0.049 | 0.78 |
| 2 | 0.098 | 0.78 |
| 3 | 0.049 | 0.39 |
| 4 | 0.098 | 0.78 |
| 5 | 0.098 | 0.39 |
| 6 | 0.098 | 0.78 |
| 7 | 0.098 | 0.39 |
| 8 | 0.024 | 0.39 |
| 9 | 0.024 | — |
| 10 | 0.098 | 0.78 |
| 11 | 0.024 | — |
| 12 | 0.012 | — |
| 13 | 0.098 | — |
| 14 | 0.195 | — |
| 15 | 0.195 | 0.78 |
| 16 | 0.098 | — |
| 17 | 0.195 | 0.78 |
| 18 | 0.098 | 0.39 |
| 19 | 0.024 | — |
| 20 | 0.098 | — |
| 21 | 0.049 | 0.39 |
| 22 | 0.049 | 0.39 |
| 23 | 0.098 | 0.78 |
| 24 | 0.195 | 1.56 |
| 25 | 0.195 | 0.39 |
| 26 | 0.098 | 0.78 |
| 27 | 0.39 | 1.56 |
| 28 | 0.78 | 0.78 |
| 29 | 0.098 | 1.56 |

Preparation 1

An injection preparation is prepared from the following components.

| Components | Amount |
| --- | --- |
| 7-(4-Methyl-1-piperazinyl)-1-cyclopropyl-6-fluoro-5,8-dimethyl-1,4-dihydro-4-oxo quinoline-3-carboxylic acid | 200 mg |
| Glucose | 250 mg |
| Distilled water for injection | q.s. |
| Totally | 5 ml |

7-(4-Methyl-1-piperazinyl)-1-cyclopropyl-6-fluoro-5,8-dimethyl-1,4-dihydro-4-oxoquinoline-3-carboxylic acid and glucose are dissolved in distilled water for injection, and the solution is added to a 5 ml ampoule, which is purged with nitrogen gas and then subjected to sterilization at 1° C. for 15 minutes to give an injection preparation.

Preparation 2

Film coated tablets are prepared from the following components.

| Components | Amount |
| --- | --- |
| 7-(4-Methyl-1-piperazinyl)-1-cyclopropyl-6-fluoro-5,8-dimethyl-1,4-dihydro-4-oxo quinoline-3-carboxylic acid | 100 g |
| Avicel (tradename of microcrystalline cellulose, manufactured by Asahi Chemical Industry Co., Ltd., Japan) | 40 g |
| Corn starch | 30 g |
| Magnesium stearate | 2 g |
| TC-5 (tradename of hydroxypropyl methylcellulose, manufactured by The Shin-Etsu Chemical Co., Ltd., Japan) | 10 g |
| Polyethylene glycol 6000 | 3 g |
| Castor oil | 40 g |
| Ethanol | 40 g |

7-(4-Methyl-1-piperazinyl)-1-cyclopropyl-6-fluoro-5,8-dimethyl-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

Preparation 3

An ointment is prepared from the following components.

| Components | Amount |
| --- | --- |
| 7-(4-Methyl-1-piperazinyl)-1-cyclopropyl-6-fluoro-5,8-dimethyl-1,4-dihydro-4-oxo-quioline-3-carboxylic acid | 2 g |
| Purified lanolin | 5 g |
| Bleached beeswax | 5 g |
| White vaseline | 88 g |
| Totally | 100 g |

Bleached beeswax is made liquid by heating, and thereto are added 7-(4-methyl-1-piperazinyl)-1-cyclopropyl-6-fluoro-5, 8-dimethyl-1,4-dihydro-4-oxoquinoline-3-carboxylic acid, purified lanolin and while vaseline, and the mixture is heated until it becomes liquid. The mixture is stirred until it is solidified to give an ointment.

What is claimed is:

1. A compound of the formula:

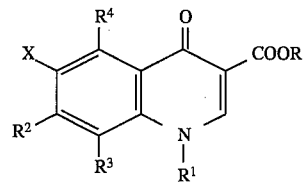

wherein $R^1$ is a cyclopropyl which may be substituted by 1 to 3 of substituents selected from the group consisting of a $C_1$–$C_6$ alkyl and a halogen atom; a phenyl which may be substituted by 1 to 3 of substituents selected from the group consisting of a $C_1$–$C_6$ alkoxy, a halogen atom and hydroxy on phenyl ring; a $C_1$–$C_6$ alkyl which may be substituted by a halogen atom, a $C_1$–$C_6$ alkanoyloxy or hydroxy; a $C_2$–$C_6$ alkenyl; or thienyl, $R^2$ is a 1-piperazinyl group which may have 1 to 3 substituents selected from the group consisting of a $C_1$–$C_6$ alkyl group, and a 2-oxo-1,3-dioxolenemethyl group which may be substituted by phenyl group or a $C_1$–$C_6$ alkyl group, $R^3$ is a $C_1$–$C_6$ alkyl, or a halogen atom, $R^4$ is a $C_1$–$C_6$ alkyl, R is hydrogen atom or a $C_1$–$C_6$ alkyl, and X is a halogan atom, or a pharmaceutically acceptable salt thereof.

2. The compound according to claim 1, wherein $R^1$ is a phenyl which may have 1 to 3 substituents selected from the group consisting of a $C_1$–$C_6$ alkoxy group, a halogen atom and hydroxy group, or a $C_1$–$C_6$ alkyl group which may by substituted by a halogen atom, a $C_2$–$C_6$ alkanoyloxy group or hydroxy group, R is hydrogen atom, and X is fluorine atom, or a pharmaceutically acceptable salt thereof.

3. The compound according to claim 1, wherein $R^1$ is a $C_2$–$C_6$ alkenyl group or thienyl group, R is hydrogen atom, and X is fluorine atom, or a pharmaceutically acceptable salt thereof.

4. The compound according to claim 1, wherein $R^1$ is unsubstituted cyclopropyl, R is hydrogen atom, X is fluorine atom, $R^3$ is a halogen atom, and $R^4$ is a $C_1$–$C_6$ alkyl group, or a pharmaceutically acceptable salt thereof.

5. The compound according to claim 1, wherein $R^1$ is unsubstituted cyclopropyl, R is hydrogen atom, X is fluorine atom, $R^3$ and $R^4$ are each a $C_1$–$C_6$ alkyl group, or a pharmaceutically acceptable salt thereof.

6. The compound according to claim 4, wherein $R^2$ is a group of the formula:

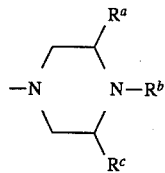

wherein $R^a$ is hydrogen atom or a $C_1$–$C_6$ alkyl group, $R^b$ is hydrogen atom, a $C_1$–$C_6$ alkyl group, a $C_1$–$C_6$ alkanoyl group, a phenyl($C_1$–$C_6$)alkyl group, or a 2-oxo-1,3-dioxolenemethyl group which is substituted by a $C_1$–$C_6$ alkyl group, $R^c$ is hydrogen atom or a $C_1$–$C_6$ alkyl group, or a pharmaceutically acceptable salt thereof.

7. The compound according to claim 6, wherein $R^a$ is hydrogen atom or a $C_1$–$C_6$ alkyl group, $R^b$ is hydrogen atom or a $C_1$–$C_6$ alkyl group, $R^c$ is hydrogen atom, $R^3$ is fluorine or chlorine atom, and $R^4$ is methyl group, or a pharmaceutically acceptable salt thereof.

8. The compound according to claim 6, wherein $R^a$ is hydrogen atom or a $C_1$–$C_6$ alkyl group, $R^b$ is hydrogen atom or a $C_1$–$C_6$ alkyl group, $R^c$ is hydrogen atom, $R^3$ is fluorine or chlorine atom, and $R^4$ is ethyl group, or a pharmaceutically acceptable salt thereof.

9. The compound according to claim 7, wherein $R^3$ is fluorine atom, or a pharmaceutically acceptable salt thereof.

10. The compound according to claim 8, wherein $R^3$ is fluorine atom, or a pharmaceutically acceptable salt thereof.

11. 7-(1-piperazinyl)-1-cyclopropyl-6, 8-difluoro-5-methyl-1,4-dihydro-4-oxoquinoline-3-carboxylic acid.

12. 7-(3-Methyl-1-piperazinyl)-1-cyclopropyl-6, 8-difluoro-5-methyl-1,4-dihydro-4-oxoquinoline-3-carboxylic acid.

13. An antimicrobial composition which comprises as an essential active ingredient an effective amount of a compound as set forth in claim 1 in admixture with a pharmaceutically acceptable carrier or diluent.

14. The composition according to claim 13, wherein the active compound is 7-(1-piperazinyl)-1-cyclopropyl-6, 8-difluoro-5-methyl-1,4-dihydro-4-oxoquinoline-3-carboxylic acid.

15. The composition according to claim 13, wherein the active compound is 7-(3-methyl-1-piperazinyl)-1-cyclopropyl-6, 8-difluoro-5-methyl-1,4-dihydro-4-oxoquinoline-3-carboxylic acid.

16. A compound of the formula:

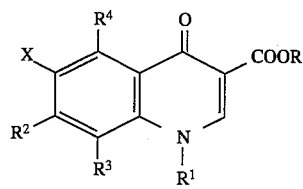

wherein $R^1$ is cyclopropyl which may be substituted by 1 to 3 substituents selected from the group consisting of lower alkyl and a halogen atom; phenyl which may be substituted by 1 to 3 substituents selected from the group consisting of lower alkoxy, a halogen atom and hydroxy; lower alkyl which may be substituted by a halogen atom, lower alkanoyloxy or hydroxy; lower alkenyl; or thienyl; $R^2$ is a 5-to 9-membered saturated or unsaturated heterocyclic ring which may be substituted, $R^3$ is lower alkyl or a halogen atom, $R^4$ is lower alkyl, R is a hydrogen atm or lower alkyl, X is a halogen atom, or a pharmaceutically acceptable salt thereof.

17. A compound of the formula:

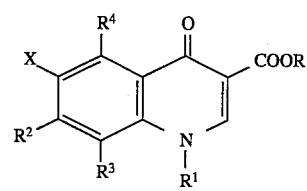

wherein $R^1$ is a cyclopropyl which may be substituted by 1 to 3 substituents selected from the group consisting of lower alkyl and a halogen atom; $R^2$ is a 5- to 9-membered saturated or unsaturated heterocyclic ring which may be substituted, $R^3$ is lower alkyl or a halogen atom, $R^4$ is lower alkyl, R is a hydrogen atom or lower alkyl, X is a halogen atom, or a pharmaceutically acceptable salt thereof.

18. 7-(3-Amino-1-pyrrolidinyl)-1-cyclopropyl-6,8-difluoro-5-methyl- 1, 4-dihydro-4-oxoquinoline-3-carboxylic acid.

19. A compound of the formula:

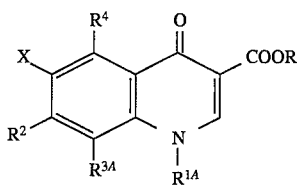

wherein R is a hydrogen atom or a $C_1$–$C_6$ alkyl group; $R^{1A}$ is a cyclopropyl which may be substituted by 1 to 3 of substituents selected from the group consisting of a $C_1$–$C_6$ alkyl and a halogen atom; a phenyl which may be substituted by 1 to 3 of substituents selected from the group consisting of a $C_1$–$C_6$ alkoxy, a halogen atom and hydroxy on the phenyl ring; a $C_1$–$C_6$ alkyl which may be substituted by a halogen atom, a $C_1$–$C_6$ alkanoyloxy or hydroxy; a $C_2$–$C_6$ alkenyl; or thienyl;

$R^2$ is a 1-pynolidinyl group which may have 1 to 3 substituents selected from the group consisting of an amino group which may have 1 to 2 substituents selected from a $C_1$–$C_6$ alkyl group and a ($C_1$–$D_6$)alkoxy-carbonyl group, an amino($C_1$–$C_6$)alkyl group which may have 1 to 2 substituents selected from a $C_1$–$C_6$ alkyl group and a ($C_1C_6$)alkoxy-carbonyl group on the amino moiety, and a $C_1$–$C_6$ alkyl group; or a morpholino group which may have 1 to 3 substituents of $C_1$–$C_6$ alkyl groups; or a 1-piperidinyl group which may have 1 to 3 substituents selected from the group consisting of a $C_1$–$C_6$ alkyl group, hydroxy, a halogen atom, and oxo group; or 1,4-diazabicyclo[4.3.0]nonan-4-yl group;

$R^{3A}$ is a $C_1$–$C_6$ alkyl group, or a halogen atom;

$R^4$ is a $C_1$–$C_6$ alkyl group; and

X is a halogen atom, or a pharmaceutically acceptable salt thereof.

20. The compound according to claim 19, wherein $R^{1A}$ is a $C_2$–$C_6$ alkenyl group or a thienyl group, R is a hydrogen atom, and X is a fluorine atom, or a pharmaceutically acceptable salt thereof.

21. The compound according to claim 19, wherein $R^{1A}$ is unsubstituted cyclopropyl, R is a hydrogen atom, X is a fluorine atom, $R^{3A}$ is a halogen atom, and $R^4$ is a $C_1$–$C_6$ alkyl group, or a pharmaceutically acceptable salt thereof.

22. The compound according to claim 19, wherein $R^{1A}$ is a phenyl which may be substituted by 1 to 3 substituents selected from the group consisting of a $C_1$–$C_6$ alkoxy, a halogen atom and hydroxy on the phenyl ring, or $R^{1A}$ is a $C_1$–$C_6$ alkyl group which may be substituted by a halogen atom, a $C_2$–$C_6$ alkanoyloxy or hydroxy; R is a hydrogen atom; and X is a fluorine atom, or a pharmaceutically acceptable salt thereof.

23. The compound according to claim 19, wherein $R^{1A}$ is unsubstituted cyclopropyl, R is a hydrogen atom, X is a fluorine atom, $R^{3A}$ and $R^4$ are each a $C_1$–$C_6$ alkyl group, or a pharmaceutically acceptable salt thereof.

24. The compound according to claim 19, wherein $R^{1A}$ is unsubstituted cyclopropyl, R is a hydrogen atom, X is a fluorine atom, $R^{3A}$ is a halogen atom, and $R^4$ is a $C_1$–$C_6$ alkyl group, and $R_2$ is a 1-pyrrolidinyl group which may have 1 to 3 substituents selected from the group consisting of an amino group which may have 1 to 2 substituents selected from a $C_1$–$C_6$ alkyl group and a ($C_1$–$C_6$)alkoxy-carbonyl group, an amino-($C_1$–$C_6$)alkyl group which may have 1 to 2 substituents selected from a $C_1$–$C_6$ alkyl group and a ($C_1$–$C_6$)alkoxy-carbonyl group on the amino moiety, and a $C_1$–$C_6$ alkyl group, or a pharmaceutically acceptable salt thereof.

25. The compound according to claim 24, wherein $R^2$ is a group of the

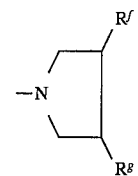

wherein $R^f$ is an amino which may have 1 to 2 substituents selected from a $C_1$–$C_6$ alkyl group and a ($C_1$–$C_6$)alkoxy-carbonyl group, or an amino ($C_1$–$C_6$)alkyl group which may have 1 to 2 substituents selected from a $C_1$–$C_6$ alkyl group and a ($C_1$–$C_6$)alkoxy-carbonyl group on the amino moiety, $R^g$ is a hydrogen atom or a $C_1$–$C_6$ alkyl group; $R^{3A}$ is a fluorine or chlorine atom; and $R^4$ is a methyl or ethyl group; or a pharmaceutically acceptable salt thereof.

26. The compound according to claim 25, wherein $R^{3A}$ is a fluorine atom, and $R^4$ is a methyl group, or a pharmaceutically acceptable salt thereof.

27. The compound according to claim 19, wherein $R^{1A}$ is unsubstituted cyclopropyl, R is a hydrogen atom, X is a fluorine atom, $R^{3A}$ is a halogen atom, and $R^4$ is a $C_1$–$C_6$ alkyl group, and $R^2$ is a morpholino group which may have 1 to 3 substituents of $C_1$–$C_6$ alkyl groups, or a pharmaceutically acceptable salt thereof.

28. The compound according to claim 27, wherein $R^2$ is a group of the formula:

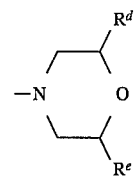

wherein $R^d$ is a hydrogen atom or a $C_1$–$C_6$ alkyl group, $R^e$ is a hydrogen atom or a $C_1$–$C_6$ alkyl group, $R^{3A}$ is a fluorine or chlorine atom; $R^4$ is a methyl or ethyl group, or a pharmaceutically acceptable salt thereof.

29. The compound according to claim 28, wherein $R^{3A}$ is a fluorine atom, and $R^4$ is a methyl group, or a pharmaceutically acceptable salt thereof.

30. The compound according to claim 19, wherein $R^{1A}$ is unsubstituted cyclopropyl, R is a hydrogen atom, X is a fluorine atom, $R^{3A}$ is a halogen atom, and $R^4$ is a $C_1$–$C_6$ alkyl group, and $R^2$ is a 1-piperidinyl group which may have 1 to 3 substituents selected from the group consisting of a $C_1$–$C_6$ alkyl group, hydroxy, a halogen atom, and oxo group, or a pharmaceutically acceptable salt thereof.

31. The compound according to claim 30, wherein $R^2$ is a group of the formula:

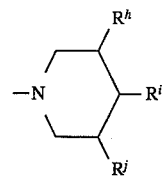

wherein $R^h$ is a hydrogen atom or a $C_1$–$C_6$ alkyl group, $R^i$ is a hydrogen atom, hydroxy, a halogen atom or oxo group, $R^j$ is a hydrogen atom or a $C_1$–$C_6$ alkyl group; $R^{3A}$ is a fluorine or chlorine atom; $R^4$ is a methyl or ethyl group; or a pharmaceutically acceptable salt thereof.

32. The compound according to claim 31, wherein $R^{3A}$ is a fluorine atom and $R^4$ is a methyl group, or a pharmaceutically acceptable salt thereof.

33. The compound according to claim 19, wherein $R^{1A}$ is unsubstituted cyclopropyl, R is a hydrogen atom, X is a fluorine atom, $R^{3A}$ is a halogen atom, and $R^4$ is a $C_1$–$C_6$ alkyl group, and $R^2$ is 1,4-diazomcyclo[4.3.0]nonan-4-yl 4-yl group, or pharmaceutically acceptable salt thereof.

34. The compound according to claim 33, wherein $R^{3A}$ is a fluorine or chlorine atom and $R^4$ is a methyl or ethyl group, or a pharmaceutically acceptable salt thereof.

35. The compound according to claim 34, wherein $R^{3A}$ is a fluorine atom and $R^4$ is a methyl group, or a pharmaceutically acceptable salt thereof.

36. An antimicrobial composition which comprises as an active ingredient an effective amount of a compound as set forth in claim 18 in admixture with a pharmaceutically acceptable carrier or diluent.

37. An antimicrobial composition which comprises as an active ingredient an effective amount of a compound as set forth in claim 19 in admixture with a pharmaceutically acceptable carrier or diluent.

* * * * *

UNITED STATES PATENT AND TRADEMARK OFFICE
CERTIFICATE OF CORRECTION

PATENT NO.: 5,591,744

DATED: January 7, 1997

INVENTOR(S): Hiraki UEDA et al.

It is certified that an error appears in the above-identified patent and that said Letters Patent is hereby corrected as shown below:

On title page of the patent, left column, under [*] Notice, change "April 8, 2008" to read --October 8, 2013--.

Signed and Sealed this

Seventeenth Day of June, 1997

*Attest:*

BRUCE LEHMAN

*Attesting Officer*         *Commissioner of Patents and Trademarks*